(12) United States Patent
Nishimura et al.

(10) Patent No.: US 7,953,261 B2
(45) Date of Patent: May 31, 2011

(54) IMAGE PROCESSING APPARATUS AND IMAGE PROCESSING METHOD

(75) Inventors: Hirokazu Nishimura, Hachioji (JP); Tetsuo Nonami, Hino (JP)

(73) Assignee: Olympus Medical Systems Corporation, Tokyo (JP)

( * ) Notice: Subject to any disclaimer, the term of this patent is extended or adjusted under 35 U.S.C. 154(b) by 1065 days.

(21) Appl. No.: 11/666,556

(22) PCT Filed: Mar. 14, 2006

(86) PCT No.: PCT/JP2006/305022
§ 371 (c)(1),
(2), (4) Date: Apr. 30, 2007

(87) PCT Pub. No.: WO2006/112227
PCT Pub. Date: Oct. 26, 2006

(65) Prior Publication Data
US 2007/0292011 A1 Dec. 20, 2007

(30) Foreign Application Priority Data

Apr. 13, 2005 (JP) .................................. 2005-115960
Apr. 13, 2005 (JP) .................................. 2005-115961

(51) Int. Cl.
*G06K 9/00* (2006.01)
*A61B 6/00* (2006.01)
(52) U.S. Cl. ........................................ 382/128; 600/476
(58) Field of Classification Search .................. 382/128, 382/129, 130, 131, 132, 133, 134, 171–173, 382/164, 179; 600/407, 410, 425, 427, 476; 128/915, 920, 922
See application file for complete search history.

(56) References Cited

U.S. PATENT DOCUMENTS

| 4,670,468 | A * | 6/1987 | Hollander et al. | 514/560 |
| 5,754,676 | A * | 5/1998 | Komiya et al. | 382/132 |
| 7,236,623 | B2 * | 6/2007 | Chapoulaud et al. | 382/133 |
| 2003/0001104 | A1 | 1/2003 | Sendai et al. | |
| 2004/0225223 | A1 | 11/2004 | Honda et al. | |
| 2004/0249291 | A1* | 12/2004 | Honda et al. | 600/476 |

FOREIGN PATENT DOCUMENTS

| EP | 1 535 568 A1 | 6/2005 |
| EP | 1 535 569 A1 | 6/2005 |

(Continued)

OTHER PUBLICATIONS

Yuqing, Mao et al., The Researching and Implementation of Morphological Recognition in the System of Diagnosing the Early Stage Lung Cancers, Computer Engineering, Aug. 1999, pp. 21-23, vol. 25, No. 8, with English abstract.

*Primary Examiner* — Abolfazl Tabatabai
(74) *Attorney, Agent, or Firm* — Scully, Scott, Murphy & Presser, P.C.

(57) ABSTRACT

An image processing apparatus and an image processing method which can improve efficiency of observation by a user are provided. The image processing apparatus of the present invention includes an image inputting unit configured to input a medical image including a plurality of color signals; a determining unit configured to determine whether the biological mucosa is sufficiently captured in the inputted medical image or not; and a controlling unit configured to control at least either of display or storage of the medical image based on the determination result in the determining unit.

59 Claims, 35 Drawing Sheets

FOREIGN PATENT DOCUMENTS

| | | |
|---|---|---|
| JP | 11-104072 | 4/1999 |
| JP | 2002-336193 | 11/2002 |
| JP | 2003-079568 | 3/2003 |
| JP | 2004-154176 | 6/2004 |
| JP | 2004-321603 | 11/2004 |
| JP | 2004-337596 | 12/2004 |
| JP | 2005-192880 | 7/2005 |
| JP | 2006-122502 | 5/2006 |
| WO | 2004/096025 | 11/2004 |
| WO | 2004/096027 | 11/2004 |

* cited by examiner

DIRECTION 5

DIRECTION 6

DIRECTION 7

DIRECTION 8

○ : OUTERMOST AREA Hkl

□ : CENTER AREA Hk

○ : OUTERMOST AREA Hkl

□ : CENTER AREA Hk

IMAGE PROCESSING APPARATUS AND IMAGE PROCESSING METHOD

TECHNICAL FIELD

The present invention relates to an image processing apparatus and an image processing method, more specifically to an image processing apparatus and an image processing method which can exclude an image in which appearances of a surface of a biological mucosa are not satisfactory captured.

BACKGROUND ART

In the medical field, observation with an image capture device such as X-ray, CT, MRT, and ultrasonic observational equipment, an endoscope apparatus and the like has been widely performed. Among such image capture devices, the endoscope apparatus has a function and a configuration in which, for example, with an elongated inserting unit inserted in a body cavity of a living body, an image of a view inside the body cavity imaged by an objective optical system laid out on the tip of the inserting unit is captured by a solid-state image sensing device or the like, the image is outputted as an image-captured signal, and the image of the view inside the body cavity is displayed on a monitor or the like based on the image-captured signal. The user observes organs or the like in a body cavity, for example, based on the image of the view inside the body cavity displayed on the monitor or the like. The endoscope apparatus can directly capture an appearance of an alimentary canal mucosa membrane. Thus, the user can integrally observe various findings such as a color of the mucous membrane, a lesion shape, minute structures of a surface of the mucosa membrane and the like, for example.

A capsule endoscope apparatus, for example, has been proposed as an image capture device that can be expected to provide almost the same availability as that of the abovementioned endoscope apparatus. Generally, the capsule endoscope apparatus includes a capsule endoscope which is placed inside the body cavity as it is swallowed by the subject for sending a captured view inside the body cavity to outside as a captured image signal; a receiver which receives that captured image signal sent outside the body cavity and then accumulates the captured image signal received; and an observation device for observing the image of the view inside the body cavity based on the captured image signal accumulated in the receiver.

As a capsule endoscope forming a capsule endoscope apparatus proceeds by peristalsis of alimentary canal, it generally takes several hours or so for the capsule endoscope to be eliminated from an anal after taken into the body cavity from the mouth. Then, as the capsule endoscope keeps on almost always outputting the captured image signal to the receiver after taken into the body cavity until eliminated from the body cavity, the number of still images as frame images accumulated in the receiver is enormous in a dynamic image for several hours, for example. In terms of streamlining observation by a user, a proposal is desired to be done such as to reduce the amount of data of an image as an image processing method for detecting a predetermined image that includes a lesion site such as a bleeding site or the like from the accumulated images performed and then a process for neither displaying nor saving an image other than the predetermined image is performed.

That described in PCT WO 02/073507 A2, for example, is known as such an abovementioned image processing method. A method for detecting abnormality in calorimetric analysis in vivo described in the patent reference is an image processing method including a method for detecting a bleeding site for each divided area of an image based on a distance from each average value in a characteristic space with a color being set as a feature value focusing on a difference between colors of normal mucosa and bleeding site, i.e., a method for detecting a predetermined image that includes a bleeding site as a lesion area.

However, the image processing method described in PCT WO 02/073507 A2 has a problem described below.

Generally speaking, in an alimentary canal, image capturing is not always performed only on the image of the surface of mucosa membrane of a living body, but image capturing is performed in a state where both of the image of foreign bodies such as stool, bubbles, mucosal fluid, food debris, or the like, and the image of the surface of mucosa membrane of a living body exist. Therefore, in the image processing method described in PCT WO 02/073507 A2 which does not take the existence of foreign bodies into consideration, there are possibilities of erroneously detecting a normal mucosa membrane as a bleeding site due to the foreign bodies, and of detecting an image in which an image of the foreign bodies occupies the most part of the whole image. As a result, in a case where an observation using the image processing method described in PCT WO 02/073507 A2 is performed, there is a problem of deterioration in observation efficiency attributed to deterioration in accuracy of detecting a lesion area.

The present invention is conceived in view of the above-described points, and an object of the present invention is to provide an image processing apparatus and an image processing method capable of improving observation efficiency by a user.

DISCLOSURE OF INVENTION

Means for Solving the Problem

A first image processing apparatus of the present invention includes an image inputting unit configured to input a medical image having a plurality of color signals; a determining unit configured to determine whether a biological mucosa is sufficiently captured in the inputted medical image or not; and a controlling unit configured to control at least either displaying or storing of the medical image based on the determination result in the determining unit.

A second image processing apparatus of the present invention is provided as the first image processing apparatus, further includes: an image dividing unit configured to divide the medical image into a plurality of areas; a feature value calculating unit configured to calculate one or more feature values in each of the plurality of areas of the medical image; an area classifying unit configured to identify which class of the plurality of classes each of the plurality of areas belongs to based on the feature value and classify each of the plurality of areas by the identification result; a classification determining value calculating unit configured to calculate a proportion of a group of areas classified in a predetermined class among the plurality of classes in the plurality of areas based on the classification result by the area classifying unit; and an image classifying unit configured to classify the image having the group of areas classified in the predetermined classes based on the proportion calculated by the classification determining value calculating unit and a predetermined threshold relating to the proportion; wherein the determining unit determines that the medical image is an image in which a biological mucosa is not sufficiently captured if the proportion is a predetermined threshold or less based on the classification result by the image classifying unit, and determines that the medical image is an image in which a biological mucosa is sufficiently captured if the proportion is larger than the predetermined threshold.

A third image processing apparatus of the present invention is provided as the second image processing apparatus, wherein the controlling unit controls not to display the medical image which is determined that the biological mucosa is not sufficiently captured by the determining unit.

A fourth image processing apparatus of the present invention is provided as the second image processing apparatus, wherein the controlling unit controls not to store the medical image which is determined that the biological mucosa is not sufficiently captured by the determining unit.

A fifth image processing apparatus of the present invention is provided as the third image processing apparatus, wherein the controlling unit controls not to store the medical image which is determined that the biological mucosa is not sufficiently captured by the determining unit.

A sixth image processing apparatus of the present invention is provided as the second image processing apparatus, further includes an image deleting unit configured to delete the medical image which is determined that the biological mucosa is not sufficiently captured by the determining unit.

A seventh image processing apparatus of the present invention is provided as the third image processing apparatus, further includes an image deleting unit configured to delete the medical image which is determined that the biological mucosa is not sufficiently captured by the determining unit.

A eighth image processing apparatus of the present invention is provided as the fourth image processing apparatus, further includes an image deleting unit configured to delete the medical image which is determined that the biological mucosa is not sufficiently captured by the determining unit.

A ninth image processing apparatus of the present invention is provided as the fifth image processing apparatus, further includes an image deleting unit configured to delete the medical image which is determined that the biological mucosa is not sufficiently captured by the determining unit.

A tenth image processing apparatus of the present invention is provided as the second image processing apparatus, wherein the feature value has at least either the feature value relating to a color or the feature value relating to a texture.

An eleventh image processing apparatus of the present invention includes: an image inputting unit configured to input a plurality of medical images including a plurality of color signals; an area setting unit configured to set a plurality of areas for the inputted medical images; a detecting unit configured to detect an area which is suspected to have a lesion from the plurality of areas; an area determining unit configured to determine whether the plurality of areas set by the area setting unit are areas in each of which a biological mucosa is captured or not; and a detection result determining unit configured to determine whether a detection result by the detecting unit is right or wrong based on the determination result in the area determining unit.

A twelfth image processing apparatus of the present invention is provided as the eleventh image processing apparatus, further includes a feature value calculating unit configured to calculate one or more feature values in each of the plurality of areas of the medical image, an area classifying unit configured to classify the plurality of areas into any of a plurality of classes including a class relating to a biological mucosa and a class relating to a non-biological mucosa based on the feature value, an edge detecting unit configured to detect an area having an edge in the plurality of areas based on a density value of a green component of the medical image, a bleeding site determining unit configured to determine whether an area having the edge is an area including a bleeding site or not based on a density value of a red component of the image, and a classification result determining unit configured to determine whether the classification result of the area classifying unit is right or wrong based on the determination result of the bleeding site determining unit, wherein the detecting unit detects an area including the bleeding site as an area which is suspected to have a lesion.

A thirteenth image processing apparatus of the present invention is provided as the twelfth image processing apparatus, wherein the area determining unit determines, if one area is classified into a class relating to a biological mucosa, that the one area is an area in which a biological mucosa is captured based on the classification result of the area classifying unit.

A fourteenth image processing apparatus of the present invention is provided as the thirteenth image processing apparatus, wherein the detection result determining unit determines that the detection result of the detection unit is correct, if the area which is suspected to have a lesion is the area in which a biological mucosa is captured based on the detection result of the detecting unit and the determination result of the area determining unit.

A fifteenth image processing apparatus of the present invention is provided as the twelfth image processing apparatus, wherein the feature value has at least either a feature value relating to a color or a feature value relating to a texture.

A sixteenth image processing apparatus of the present invention includes: an image inputting unit configured to input a plurality of medical images captured serially in time order; an area setting unit configured to set a plurality of areas in the medical image; a determining unit configured to determine an object of image capturing in the plurality of areas set by the area setting unit; an identifying unit configured to identify an organ whose image is captured in the medical image based on a determination result of the determining unit; and an identification result displaying unit configured to display an identification result by the identifying unit.

A seventeenth image processing apparatus of the present invention is provided as the sixteenth image processing apparatus, further includes: an image dividing unit configured to divide the medical image into a plurality of areas; a feature value calculating unit configured to calculate one or more feature values in each of the plurality of areas of the medical image; an area classifying unit configured to identify which class of a plurality of classes each of the plurality of areas belongs to based on the feature value and classify each of the plurality of areas by the identification result; a classification determination value calculating unit configured to calculate a proportion of a group of areas classified in a predetermined class among the plurality of classes in the plurality of areas based on the classification result by the area classifying unit; and an image classifying unit configured to classify the image having the group of areas classified into the predetermined class based on the proportion calculated by the classification determination value calculating unit and the predetermined threshold relating to the proportion; wherein the identifying unit identifies an organ whose image is captured in the medical image based on the classification result of the image classifying unit.

An eighteenth image processing apparatus is provided as the seventeenth image processing apparatus, wherein the plurality of classes has at least a gastric mucosa class, a villi class, and a feces class.

A nineteenth image processing apparatus is provided as the eighteenth image processing apparatus, wherein, if the predetermined class is the gastric mucosa class, the identifying unit determines that the organ whose image is captured in the medical image is a the gaster.

A twentieth image processing apparatus of the present invention is provided as the eighteenth image processing apparatus, wherein, if the predetermined class is the villi class, the identifying unit determines that the organ whose image is captured in the medical image is the small intestine.

A twenty-first image processing apparatus of the present invention is provided as the eighteenth image processing apparatus, wherein, if the predetermined class is the feces class, the identifying unit determines that the organ whose image is captured in the medical image is the large intestine.

A twenty-second image processing apparatus of the present invention is provided as the seventeenth image processing apparatus, wherein the feature value has at least either the feature value relating to a color or the feature value relating to a texture.

A twenty-third image processing apparatus of the present invention includes: an image signal inputting unit configured to input an image signal based on an image captured by a medical appliance having an image capturing function; an image dividing unit configured to divide an image captured by the medical appliance into a plurality of areas based on the image signals inputted by the image signal inputting unit; a feature value calculating unit configured to calculate one or more feature values in each of the plurality of areas divided by the image dividing unit; a first area classifying unit configured to classify the plurality of areas into any of the plurality of classes based on the feature value calculated by the feature value calculating unit and a predetermined first classifying criterion; a classifying criterion setting unit configured to set a second classifying criterion based on the feature value and the classification result by the first area classifying unit; and a second area classifying unit configured to classify the plurality of areas into any of the plurality of classes based on the feature value and the second classifying criterion.

A twenty-fourth image processing apparatus is provided as the twenty-third image processing apparatus, wherein the feature value has at least either the feature value relating to a color or the feature value relating to a texture.

A twenty-fifth image processing apparatus is provided as the twenty-third image processing apparatus, wherein the first area classifying unit classifies each of the plurality of areas into any of the plurality of classes by using a statistical discriminator which uses a parameter for determining the first classifying criterion, and the second area classifying unit classifies each of the plurality of areas into any of the plurality of classes by using a statistical discriminator which uses a parameter for determining the second classifying criterion.

A twenty-sixth image processing apparatus includes: an image signal inputting unit configured to input an image signal based on an image captured by a medical appliance having an image capturing function; an image dividing unit configured to divide an image captured by the medical appliance into a plurality of areas based on the image signal inputted by the image signal inputting unit; a feature value calculating unit configured to calculate one or more feature values in each of the plurality of areas divided by the image dividing unit; a first area classifying unit configured to classify the plurality of areas into any of the plurality of classes based on the feature value calculated by the feature value calculating unit and a predetermined first classifying criterion, an evaluated value calculating unit configured to evaluate the classification result by the first area classifying unit of one area among the plurality of areas by calculating an evaluated value based on the classification result by the first area classifying unit of the area placed near the one area; and a second area classifying unit configured to classify the one area into any of the plurality of classes based on the evaluated value in the evaluated value calculating unit.

A twenty-seventh image processing apparatus is provided as the twenty-sixth image processing apparatus, wherein the feature value has at least either the feature value relating to a color or the feature value relating to a texture.

A twenty-eighth image processing apparatus includes: an image signal inputting unit configured to input an image signal based on an image captured by a medical appliance having an image capturing function; an image dividing unit configured to divide an image captured by the medical appliance into a plurality of areas based on the image signal inputted by the image signal inputting unit; a feature value calculating unit configured to calculate one or more feature values in each of the plurality of areas divided by the image dividing unit; a notice area setting unit configured to set one area among the plurality of areas as a notice area; a close circumference area detecting unit configured to detect a close circumference area which is an area at a predetermined distance from the notice area; an approximately round shape detecting unit configured to detect the presence of at least a part of a contour part of the approximately round shape based on the feature value in the close circumference area; and an area extracting unit configured to extract the notice area, if the approximately round shape is detected by the approximately round shape detecting unit.

A twenty-ninth image processing apparatus is provided as the twenty-eighth image processing apparatus, wherein the feature value has at least either the feature value relating to a color or the feature value relating to a texture.

A thirtieth image processing apparatus is provided as the twenty-eighth image processing apparatus, wherein the approximately round shape detecting unit detects an approximately round shape if it is determined that a proportion of an area in which at least a part of the contour part of the approximately round shape is a predetermined threshold or more in the close circumference area, and the area extracting unit extracts the notice area as an area in which a center part of the approximately round shape is present.

A thirty-first image processing apparatus is provided as the twenty-ninth image processing apparatus, wherein the approximately round shape is a bubble.

A thirty-second image processing apparatus is provided as the thirtieth image processing apparatus, wherein the approximately round shape is a bubble.

A thirty-third image processing apparatus of the present invention includes: an image signal inputting unit configured to input an image signal based on an image captured by a medical appliance having an image capturing function; an image dividing unit configured to divide an image captured by the medical appliance into a plurality of areas based on the image signal inputted by the image signal inputting unit; a feature value calculating unit configured to calculate one or more feature values in each of the plurality of areas divided by the image dividing unit; an area classifying unit configured to classify the plurality of areas into any of a plurality of classes based on the feature value calculated in the feature value calculating unit and a predetermined classifying criterion; an area detecting unit configured to detect an area classified into a predetermined class previously set as a class having a structurally definite feature among the plurality of classes from the plurality of areas; and a classifying criterion setting unit configured to set the predetermined classifying criterion in the area classifying unit based on the feature value of the area detected in the area detecting unit.

A thirty-fourth image processing apparatus of the present invention is provided as the thirty-third image processing apparatus, wherein the predetermined class is at least either a bubble class or a villi class.

A thirty-fifth image processing apparatus is provided as the thirty-third image processing apparatus, wherein the feature value has at least either the feature value relating to a color or the feature value relating to a texture.

A first image processing method of the present invention includes: an image inputting step for inputting an image captured by a medical appliance having an image capturing function; an area dividing step for dividing the image into a plurality of areas; a feature value calculating step for calculating one or more feature values from each of the plurality of areas; and an area classifying step for classifying each of the plurality of areas into either an area in which a surface of a biological mucosa is captured or an area in which a non-biological mucosa is captured based on the feature value.

A second image processing method of the present invention includes: an image inputting step for inputting an image captured by a medical appliance having an image capturing function; an area dividing step for dividing the image into a plurality of areas; a feature value calculating step for calculating one or more feature values from each of the plurality of areas; and an area classifying step for classifying each area of the plurality of areas into any of a plurality of different classes based on the feature value, wherein the area classifying step classifies each area of the plurality of areas into any of an area in which a surface of a biological mucosa is captured, an area in which a non-biological mucosa is captured, and an area which is neither the surface of the biological mucosa nor the non-biological mucosa.

A third image processing method of the present invention includes: an image inputting step for inputting an image captured by a medical appliance having an image capturing function; an area dividing step for dividing the image into a plurality of areas; a feature value calculating step for calculating one or more feature values from each of the plurality of areas; an area classifying step for classifying each area of the plurality of areas into any one class among a plurality of different classes based on the feature value; an excluded class setting step for setting combinations of excluded classes which are not permitted to be mixed on the image in the plurality of different classes; and a preferential class setting step for setting which class is to be preferred among the combinations of the excluded classes, wherein if an area classified into any class of the combinations of the excluded class set at the excluded class setting step is present, the area classifying step classifies the area into a class set at the preferential class setting.

A fourth image processing method of the present invention is provided as the third image processing method, further includes a classification determining value calculating step for calculating a proportion of a group of areas classified in a class among the classes included in the combinations of the excluded classes in the plurality of areas based on the classification result at the area classifying step, wherein the preferential class setting sets which class among the combinations of excluded classes is to be preferred by comparing the proportion calculated at the classification determining value calculating step and a predetermined threshold relating to the proportion.

A fifth image processing method of the present invention is provided as the first image processing method, wherein the feature value has at least either the feature value relating to a color or the feature value relating to a texture.

A sixth image processing method of the present invention is provided as the second image processing method, wherein the feature value has at least either the feature value relating to a color or the feature value relating to a texture.

A seventh image processing method of the present invention is provided as the third image processing method, wherein the feature value has at least either the feature value relating to a color or the feature value relating to a texture.

An eighth image processing method of the present invention is provided as the first image processing method, further includes a determining step for determining whether a surface of a biological mucosa is captured in the image or not based on the classification result of each of the plurality of areas at the area classifying step.

A ninth image processing method of the present invention is provided as the second image processing method, further includes a determining step for determining whether a surface of a biological mucosa is captured in the image or not based on the classification result of each of the plurality of areas at the area classifying step.

A tenth image processing method of the present invention is provided as the fourth image processing method, further includes a determining step for determining whether a surface of a biological mucosa is captured in the image or not based on the classification result of each of the plurality of areas at the area classifying step.

An eleventh image processing method of the present invention is provided as the eighth image processing method, further includes: a classification determining value calculating step for calculating a proportion of a group of areas classified in a predetermined class among the plurality of different classes in the plurality of areas based on the classified result at the area classifying step; and an image classifying step for classifying the image having the group of areas classified into the predetermined class based on the proportion calculated at the classification determining value calculating step and a predetermined threshold relating to the proportion; wherein the determining step determines that the image is an image in which a biological mucosa is insufficiently captured if the proportion is a predetermined threshold or less, and determines that the image is an image in which a biological mucosa is sufficiently captured in the image if the proportion is more than the predetermined threshold based on the classification result at the image classifying step.

A twelfth image processing method of the present invention is provided as the ninth image processing method, further includes: a classification determining value calculating step for calculating a proportion of a group of areas classified in a predetermined class among the plurality of different classes in the plurality of areas based on classification result at the area classifying step; and an image classifying step for classifying the image having the group of areas classified into the predetermined class based on the proportion calculated at the classification determining value calculating step and a predetermined threshold relating to the proportion; wherein the determining step determines that the image is an image in which a biological mucosa is insufficiently captured if the proportion is a predetermined threshold or less based on the classification result at the image classifying step, and determines that the image is an image in which a biological mucosa is sufficiently captured if the proportion is more than the predetermined threshold.

A thirtieth image processing method of the present invention is provided as the tenth image processing method, further includes: a classification determining value calculating step for calculating a proportion of a group of areas classified in a predetermined class among the plurality of different classes in the plurality of areas based on classification result at the area classifying step; and an image classifying step for classifying the image having the group of areas classified into the predetermined class based on the proportion calculated at the classification determining value calculating step and a predetermined threshold relating to the proportion; wherein the determining step determines that the image is an image in which a biological mucosa is insufficiently captured if the proportion is a predetermined threshold or less based on the classification result at the image classifying step, and determines that the image is an image in which a biological mucosa is sufficiently captured if the proportion is more than the predetermined threshold.

A fourteenth image processing method of the present invention includes: an image inputting step for inputting an image captured by a medical appliance having an image capturing function; an area dividing step for dividing the image into a plurality of areas; a feature value calculating step for calculating one or more feature values in each of the plurality of areas; an area classifying step for identifying which class of a plurality of classes each of the plurality of areas belongs to based on the feature value and classifying each of the plurality of areas by the identification result; and an image-captured organ estimating step for estimating an organ whose image is captured by the medical appliance based on the classification result at the area classifying step.

A fifteenth image processing method of the present invention is provided as the fourteenth image processing method, further includes: a classification determining value calculating step for calculating a proportion of a group of areas classified in a predetermined class among the plurality of classes in the plurality of areas based on the classification result at the area classifying step; an image classifying step for classifying the image having the group of areas classified into the predetermined class based on the proportion calculated at the classification determining value calculating step and a predetermined threshold relating to the proportion; wherein the image-captured organ estimating step identifies the organ captured in the image based on the classification result at the image classifying step.

A sixteenth image processing method is provided as the fifteenth image processing method, wherein the plurality of classes has at least a gastric mucosa class, a villi class, and a feces class.

A seventeenth image processing method is provided as the sixteenth image processing method, wherein, if the predetermined class is the gastric mucosa class, the identifying unit determines that the organ whose image is captured in the image is the gaster.

An eighteenth image processing method of the present invention is provided as the sixteenth image processing method, wherein, if the predetermined class is the villi class, the identifying unit determines that the organ whose image is captured in the image is the small intestine.

A nineteenth image processing method of the present invention is provided as the sixteenth image processing method, wherein, if the predetermined class is the feces class, the identifying unit determines that the organ whose image is captured in the image is the large intestine.

A twentieth image processing method of the present invention is provided as the fourteenth image processing method, wherein the feature value has at least either the feature value relating to a color or the feature value relating to a texture.

A twenty-first image processing method of the present invention includes: an image dividing step for dividing the image captured by the medical appliance into a plurality of areas based on the image signal inputted at the image signals inputting unit configured to input an image signal according to an image captured by the medical appliance having an image capturing function; a feature value calculating step for calculating one or more feature values in each of a plurality of areas divided at the image dividing step; a first area classifying step for classifying each of the plurality of areas into any of a plurality of classes based on the feature value calculated at the feature value calculating step and a predetermined first classifying criterion; a classifying criterion setting step for setting a second classifying criterion based on the feature value and the classification result at the first area classifying step; and a second area classifying step for classifying each of the plurality of areas into any of the plurality of classes based on the feature value and the second classifying criterion.

A twenty-second image processing method of the present invention is provided as the twenty-first image processing method, wherein the feature value has at least either the feature value relating to a color or the feature value relating to a texture.

A twenty-third image processing method of the present invention is provided as the twenty-first image processing method, wherein the first area classifying step classifies each of the plurality of areas into any of the plurality of classes by using a statistical discriminator which uses a parameter for determining the first classifying criterion, and the second area classifying step classifies each of the plurality of areas into any of the plurality of classes by using a statistical discriminator which uses a parameter for determining the second classifying criterion.

A twenty-fourth image processing method of the present invention includes: an image dividing step for dividing the image captured by the medical appliance into a plurality of areas based on the image signal inputted by the image signal inputting unit configured to input an image signal according to an image captured by the medical appliance having an image capturing function; a feature value calculating step for calculating one or more feature values in each of a plurality of areas divided at the image dividing step; a first area classifying step for classifying each of the plurality of areas into any of a plurality of classes based on the feature value calculated at the feature value calculating step and a predetermined first classifying criterion; an evaluated value calculating step for evaluating the classification result at the first area classifying step of one area among the plurality of areas by calculating an evaluated value based on the classification result at the first area classifying step of the area placed near the one area; and a second area classifying step for classifying the one area into any of the plurality of classes based on the evaluated value at the evaluated value calculating step.

A twenty-fifth image processing method of the present invention is provided as the twenty-fourth image processing method, wherein the feature value has at least either the feature value relating to a color or the feature value relating to a texture.

A twenty-sixth image processing method of the present invention includes: an image dividing step for dividing the image captured by the medical appliance into a plurality of areas based on the image signal inputted at the image signals inputting unit configured to input an image signal according to an image captured by the medical appliance having an image capturing function; a feature value calculating step for calculating one or more feature values in each of the plurality of areas divided at the image dividing step; a notice area setting step for setting one area among the plurality of areas as a notice area; a close circumference area detecting step for detecting a close circumference area which is an area at a predetermined distance from the notice area; an approximately round shape detecting step for detecting the presence of at least a part of a contour part of the approximately round shape based on the feature value in the close circumference area; and an area extracting step for extracting the notice area, if the approximately round shape is detected at the approximately round shape detecting step.

A twenty-seventh image processing method is provided as the twenty-sixth image processing method, wherein the feature value has at least either the feature value relating to a color or the feature value relating to a texture.

A twenty-eighth image processing method of the present invention is provided as the twenty-sixth image processing method, wherein the approximately round shape detecting step detects an approximately round shape if it is determined that a proportion of an area in which at least a part of the contour part of the approximately round shape is a predetermined threshold or more in the close circumference area, and the area extracting step extracts the notice area as an area in which a center part of the approximately round shape exists.

A twenty-ninth image processing method is provided as the twenty-sixth image processing method, wherein the approximately round shape is a bubble.

A thirtieth image processing method of the present invention is provided as the twenty-eighth image processing method, wherein the approximately round shape is a bubble.

A thirty-first image processing method of the present invention includes: an image dividing step for dividing the image captured by the medical appliance into a plurality of areas based on the image signal inputted by the image signal inputting unit configured to input an image signal according to an image captured by the medical appliance having an image capturing function; a feature value calculating step for calculating one or more feature values in each of the plurality of areas divided at the image dividing step; an area classifying step for classifying each of the plurality of areas into each of a plurality of classes based on the feature value calculated at the feature value calculating step and a predetermined classifying criterion; an area detecting step for detecting an area classified into a predetermined class previously set as a class having a structurally definite feature among the plurality of classes from the plurality of areas; and a classifying criterion setting step for setting the predetermined classifying criterion at the area classifying step based on the feature value of the area detected at the area detecting step.

A thirty-second image processing method of the present invention is provided as the thirty-first image processing method, wherein the feature value has at least either the feature value relating to a color or the feature value relating to a texture.

A thirty-third image processing method is provided as the thirty-first image processing method, wherein the predetermined class is at least either a bubble class or a villi class.

A thirty-fourth image processing method of the present invention includes: inputting an image captured by a medical appliance; dividing the image into a plurality of areas; calculating one or more feature values from each of the plurality of areas; and classifying each of the plurality of areas into either an area in which a surface of a biological mucosa is captured or an area in which a non-biological mucosa is captured based on the feature value.

A thirty-fifth image processing method of the present invention includes: inputting an image captured by a medical appliance; dividing the image into a plurality of areas; calculating one or more feature values from each of the plurality of areas; and classifying each area of the plurality of areas into any one class among a plurality of different classes based on the feature value and classifying each area of the plurality of areas into any of an area in which a surface of a biological mucosa is captured, an area in which a non-biological mucosa is captured, and an area which is neither the surface of the biological mucosa nor the non-biological mucosa.

A thirty-sixth image processing method of the present invention includes: inputting an image captured by a medical appliance; dividing the image into a plurality of areas; calculating one or more feature values from each of the plurality of areas; classifying each area of the plurality of areas into any one class among a plurality of different classes based on the feature value; setting combinations of excluded classes which are not permitted to be mixed on the image in the plurality of different classes; setting one class to be preferentially classified among the combinations of the excluded classes; and classifying the area into the one class, if an area classified into any class of the combinations of the excluded classes is present.

A thirty-seventh image processing method of the present invention includes: inputting an image captured by a medical appliance; dividing the image into a plurality of areas; calculating one or more feature values in each of the plurality of areas; identifying which class of a plurality of classes each of the plurality of areas belongs to based on the feature value and classifying each of the plurality of areas by the identification result; and estimating an organ whose image is captured by the medical appliance based on the classification result.

A thirty-eighth image processing method of the present invention includes: dividing the image captured by the medical appliance into a plurality of areas based on the image signal inputted at an image signals inputting unit configured to input an image signal according to an image captured by a medical appliance; calculating one or more feature values in each of a plurality of areas; classifying each of the plurality of areas into any of a plurality of classes based on the feature value and a predetermined first classifying criterion; setting a second classifying criterion based on the feature value and the classification result; and classifying each of the plurality of areas into any of the plurality of classes based on the feature value and the second classifying criterion.

A thirty-ninth image processing method of the present invention includes: inputting an image signal according to an image captured by a medical appliance and dividing the image captured by the medical appliance into a plurality of areas based on the image signal; calculating one or more feature values in each of a plurality of areas; classifying each of the plurality of areas into any of a plurality of classes based on the feature value and a predetermined first classifying criterion; evaluating the classification result of one area among the plurality of areas by calculating an evaluated value based on the classification result of the area placed near the one area; and classifying the one area into any of the plurality of classes based on the evaluated value.

A fortieth image processing method of the present invention includes: inputting an image signal according to an image captured by a medical appliance and dividing the image captured by the medical appliance into a plurality of areas based on the image signal; calculating one or more feature values in each of the plurality of areas; setting an area among the plurality of areas as a notice area; detecting a close circumference area which is an area at a predetermined distance from the notice area; detecting a presence of at least a part of a contour part of the approximately round shape based on the feature value in the close circumference area; and extracting the notice area, if the approximately round shape is detected.

A forty-first image processing method of the present invention includes: inputting an image signal according to an image captured by a medical appliance and dividing the image captured by the medical appliance into a plurality of areas based on the image signal; calculating one or more feature values in each of the plurality of areas; classifying each of the plurality of areas into any of a plurality of classes based on the feature value and a predetermined classifying criterion; detecting an area group classified into a predetermined class previously set as a class having a structurally definite feature among the plurality of classes from the plurality of areas; and setting the predetermined classifying criterion based on the feature value of the area group.

BEST MODE FOR CARRYING OUT THE INVENTION

Embodiments of the present invention will be described with reference to drawings.

First Embodiment

Figure 1:
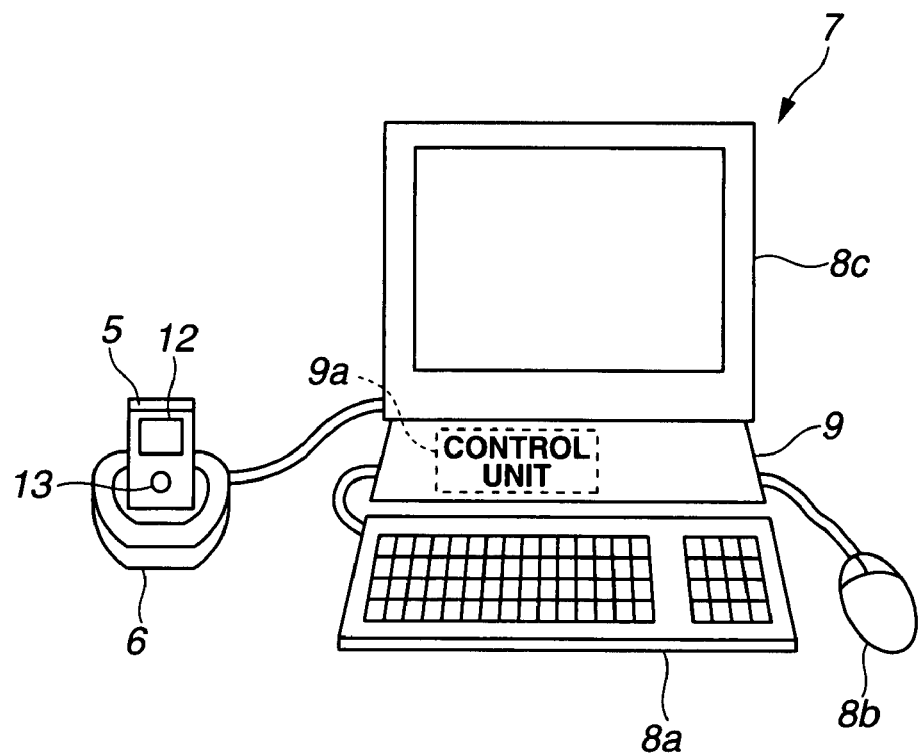
FIG. 1 is a front view of an appearance showing an appearance of an image processing apparatus and a peripheral appliance in which an image processing operation of a first embodiment is performed.
Figure 2:
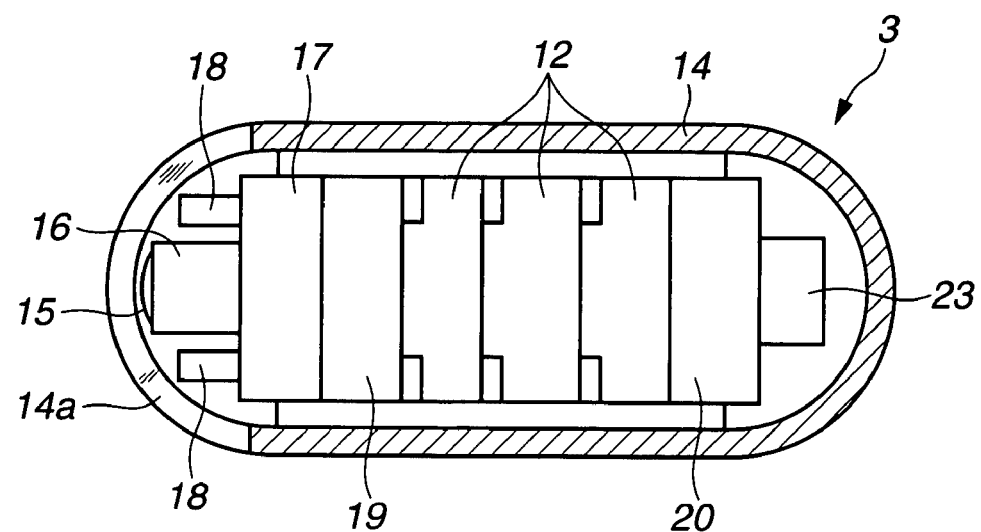
FIG. 2 is a magnification of a substantial part showing a part of a capsule endoscope for generating predetermined image information processed in the image processing apparatus of the first embodiment.
Figure 3:
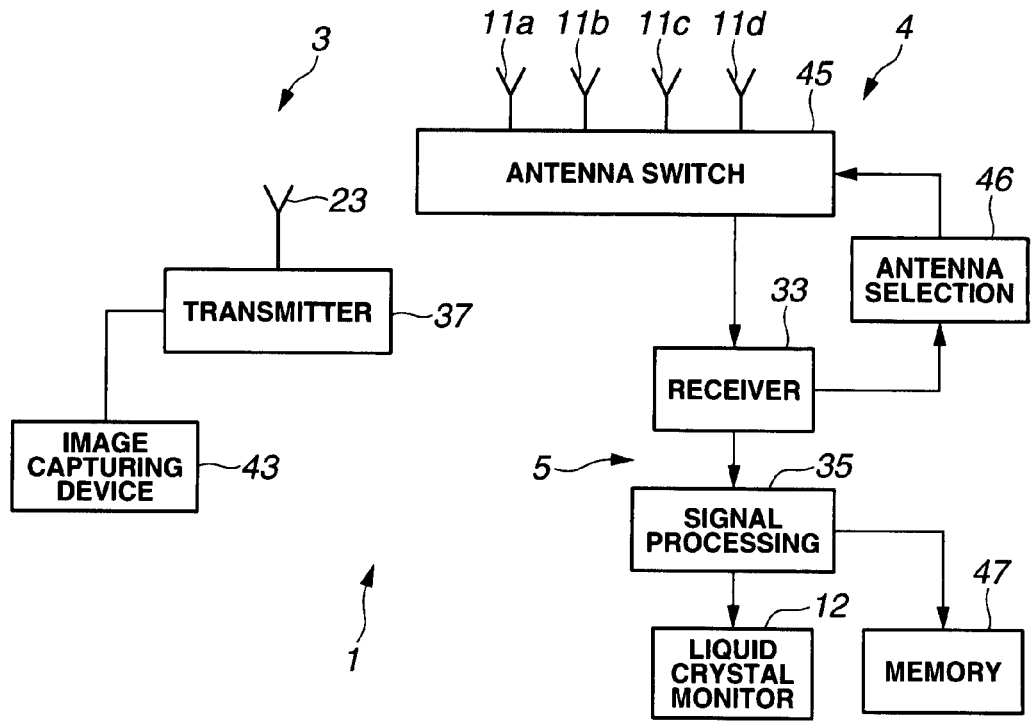
FIG. 3 is a block diagram showing an outlined inside configuration of a capsule endoscope apparatus, which supplies predetermined image information for an image processing apparatus of the first embodiment.
Figure 4:
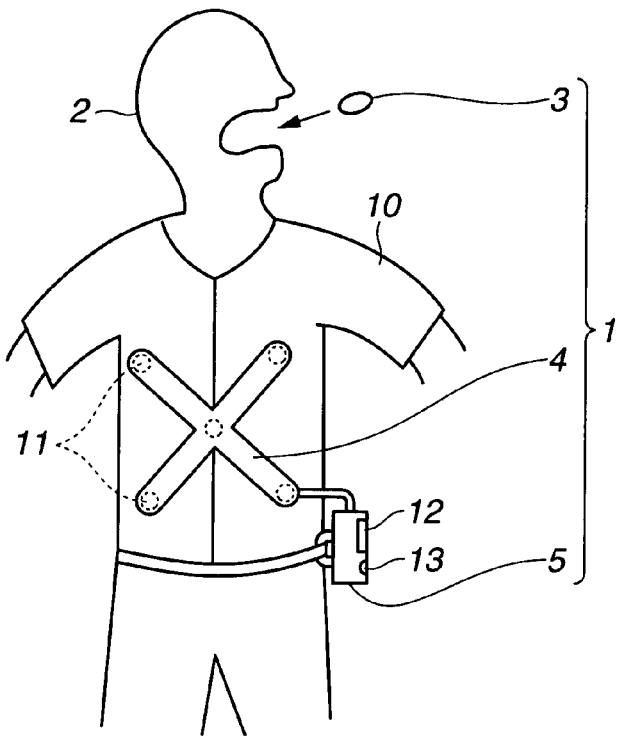
FIG. 4 is a diagram showing an example of how a capsule endoscope apparatus, which supplies predetermined image information for an image processing apparatus of the first embodiment, is used.
Figure 5:
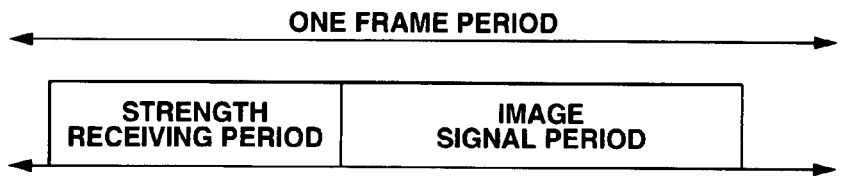
FIG. 5 is a timing chart showing an example of a signal outputted from a capsule endoscope apparatus shown in FIG. 2.
Figure 6:
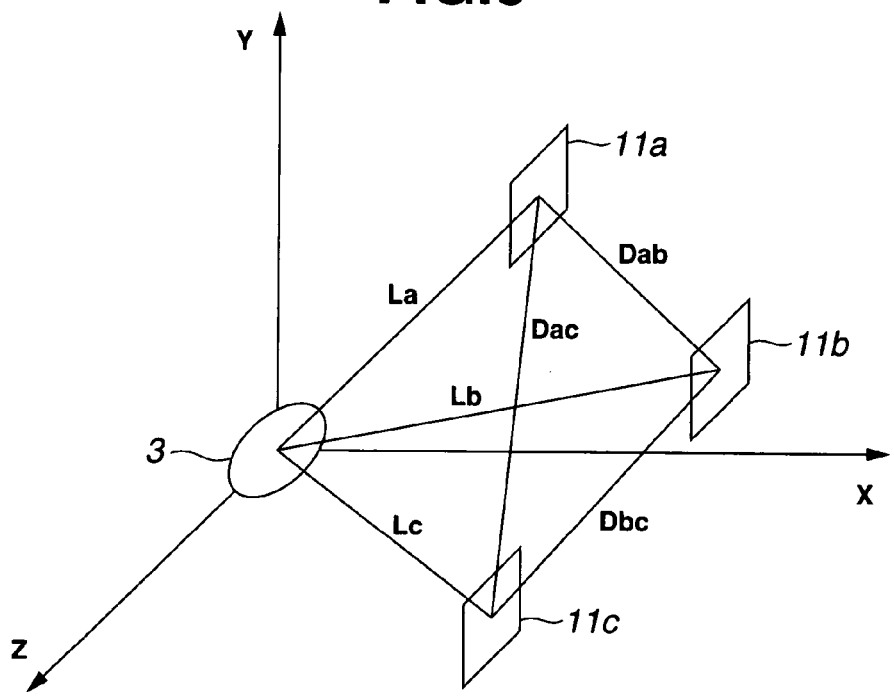
FIG. 6 is an illustration for explaining detection of the position of the capsule endoscope shown in FIG. 2.
Figure 7:
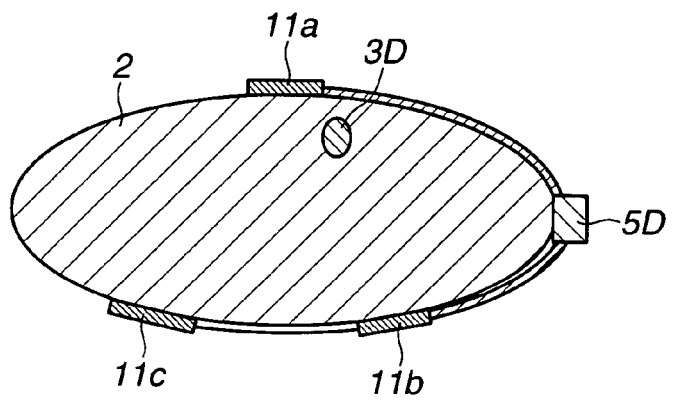
FIG. 7 is a magnification of a substantial part showing an antenna unit when the capsule endoscope apparatus shown in FIG. 3 is used.
Figure 8:
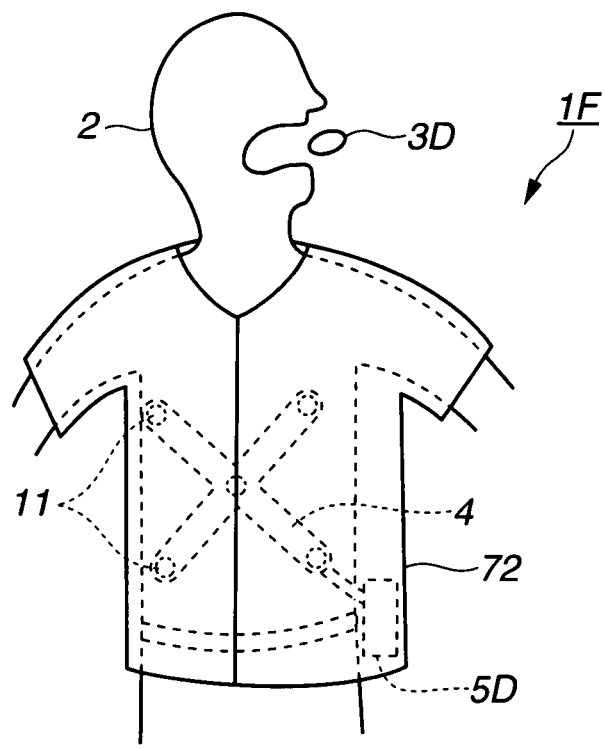
FIG. 8 is an illustration for explaining the shield jacket when the capsule endoscope apparatus shown in FIG. 3 is used.
Figure 9:
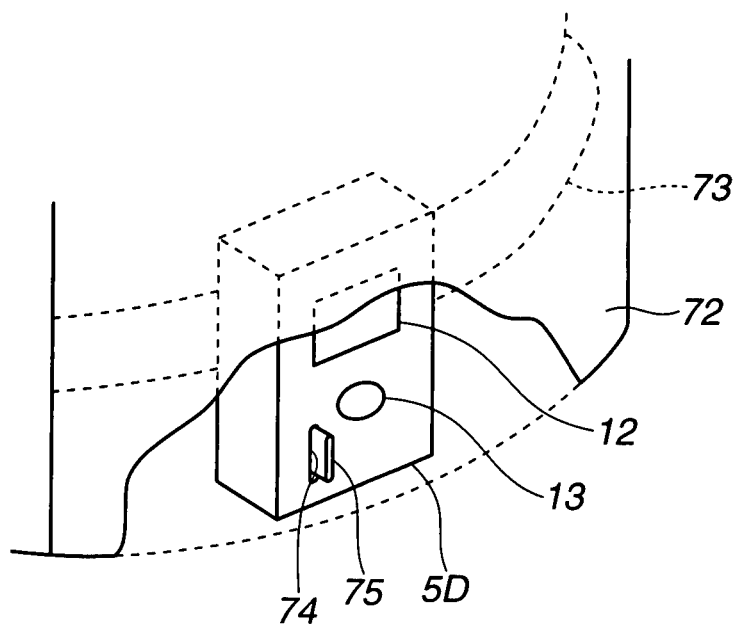
FIG. 9 is an illustration for explaining the state in which the external apparatus of the capsule endoscope apparatus shown in FIG. 3 is attached to the object.
Figure 10:
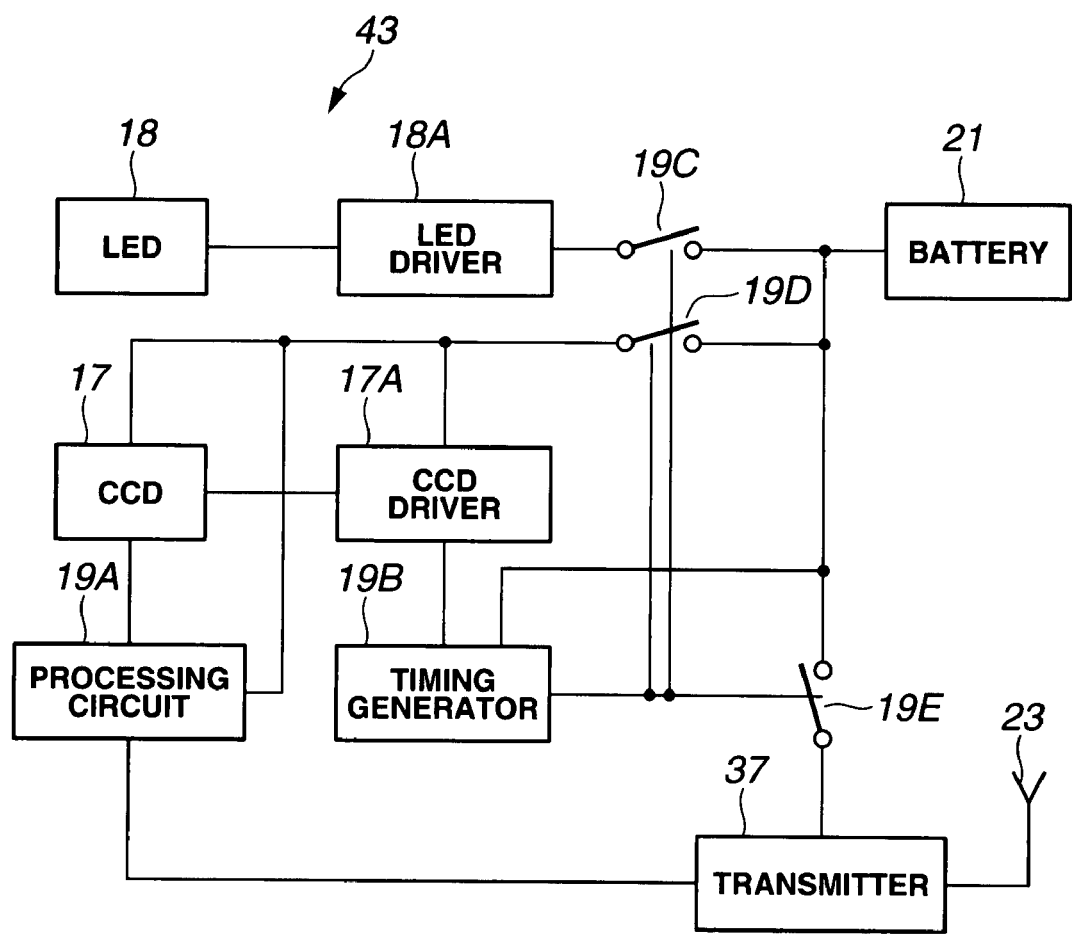
FIG. 10 is a block diagram showing an electric configuration of the capsule endoscope shown in FIG. 2.
Figure 11:
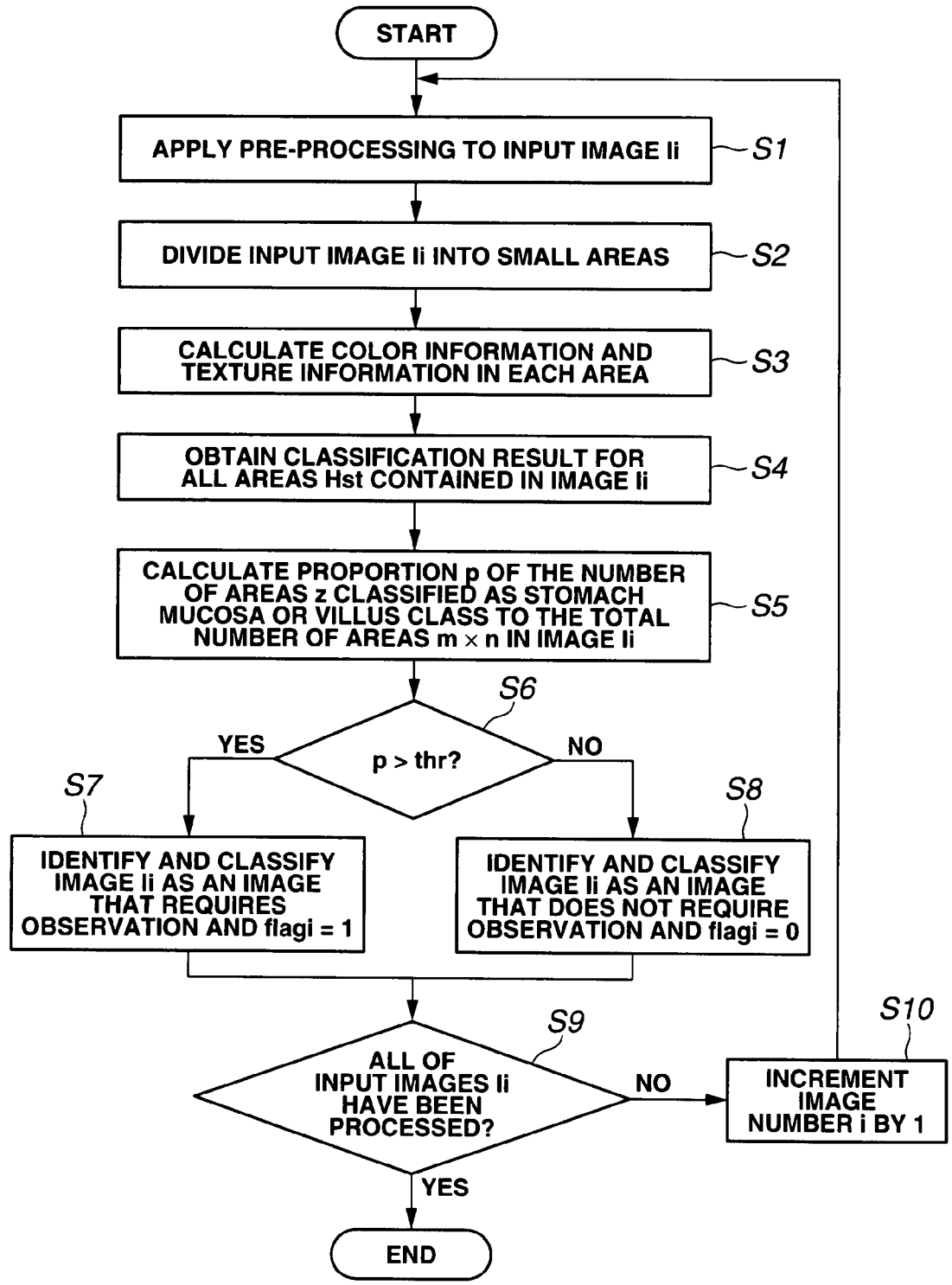
FIG. 11 is a flowchart showing an image processing operation according to the first embodiment.
Figure 12:
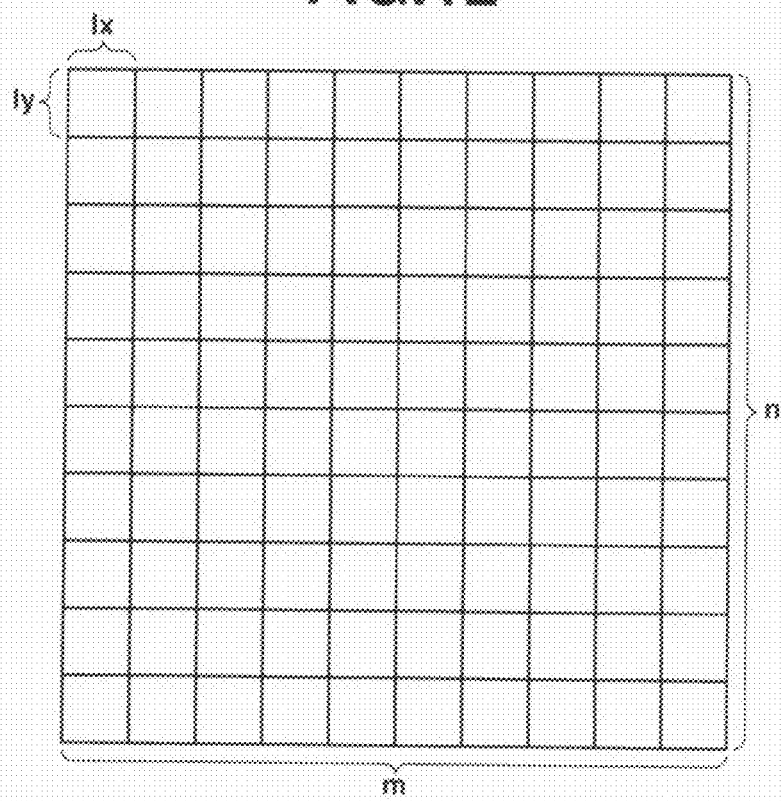
FIG. 12 is a diagram showing an example when an inputted image is divided into (m×n) areas in the image processing operation according to the first embodiment.
Figure 13:
FIG. 13 is a diagram showing an example of a gastric mucosa in a plurality of images comprising training data.
Figure 14:
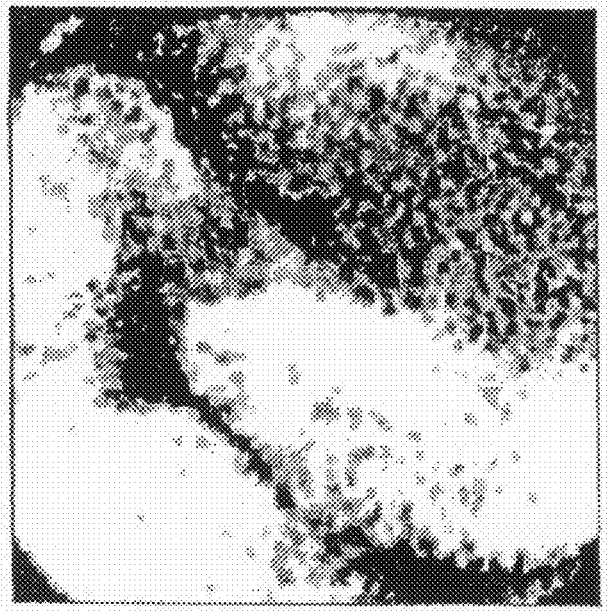
FIG. 14 is a diagram showing an image of villi in a plurality of images comprising training data.
Figure 15:
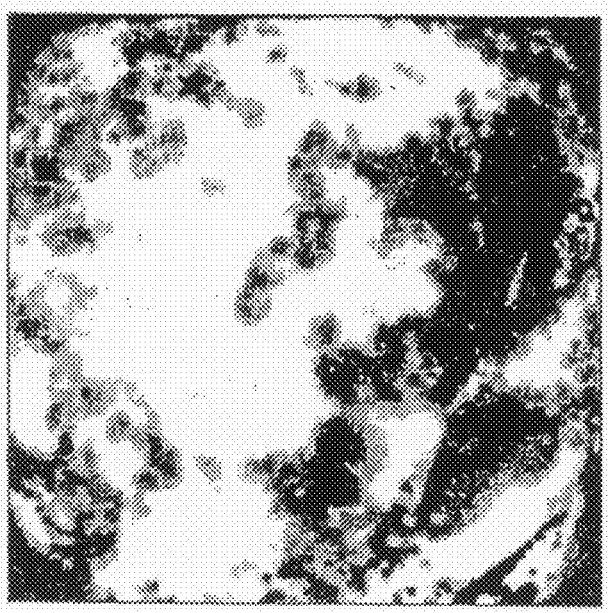
FIG. 15 is a diagram showing an example of feces in a plurality of images comprising training data.
Figure 16:
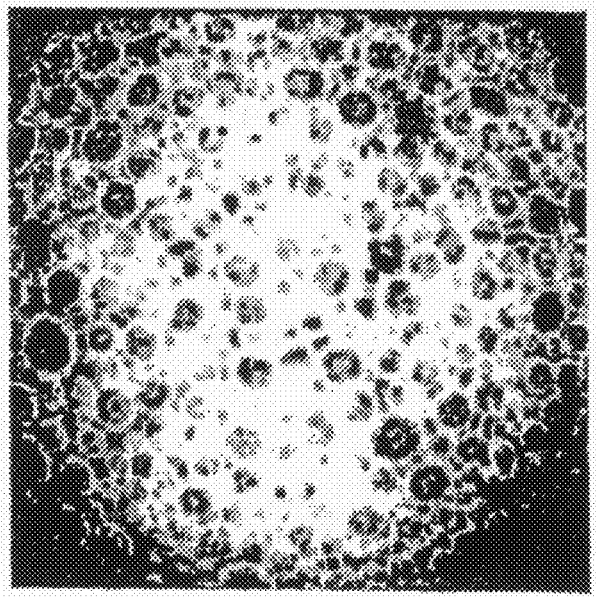
FIG. 16 is a diagram showing an example of an image of bubbles in a plurality of images comprising training data.
Figure 17:
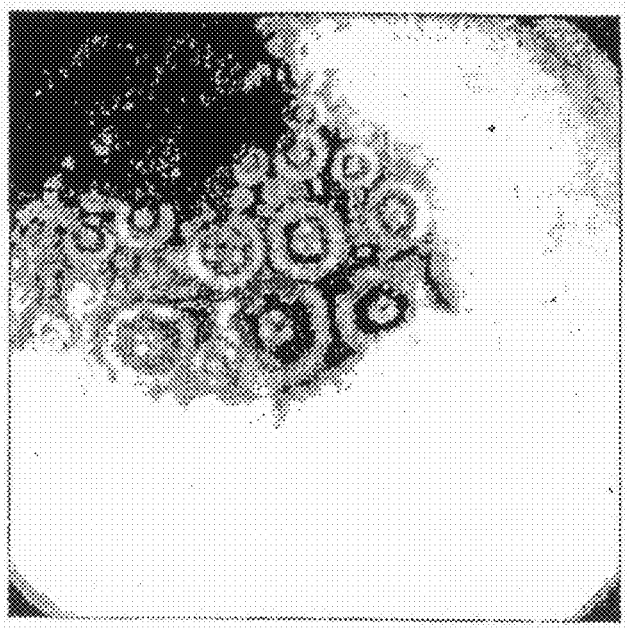
FIG. 17 is a schematic diagram showing an example of an image in a body cavity whose image is captured by the capsule endoscope.
Figure 18:
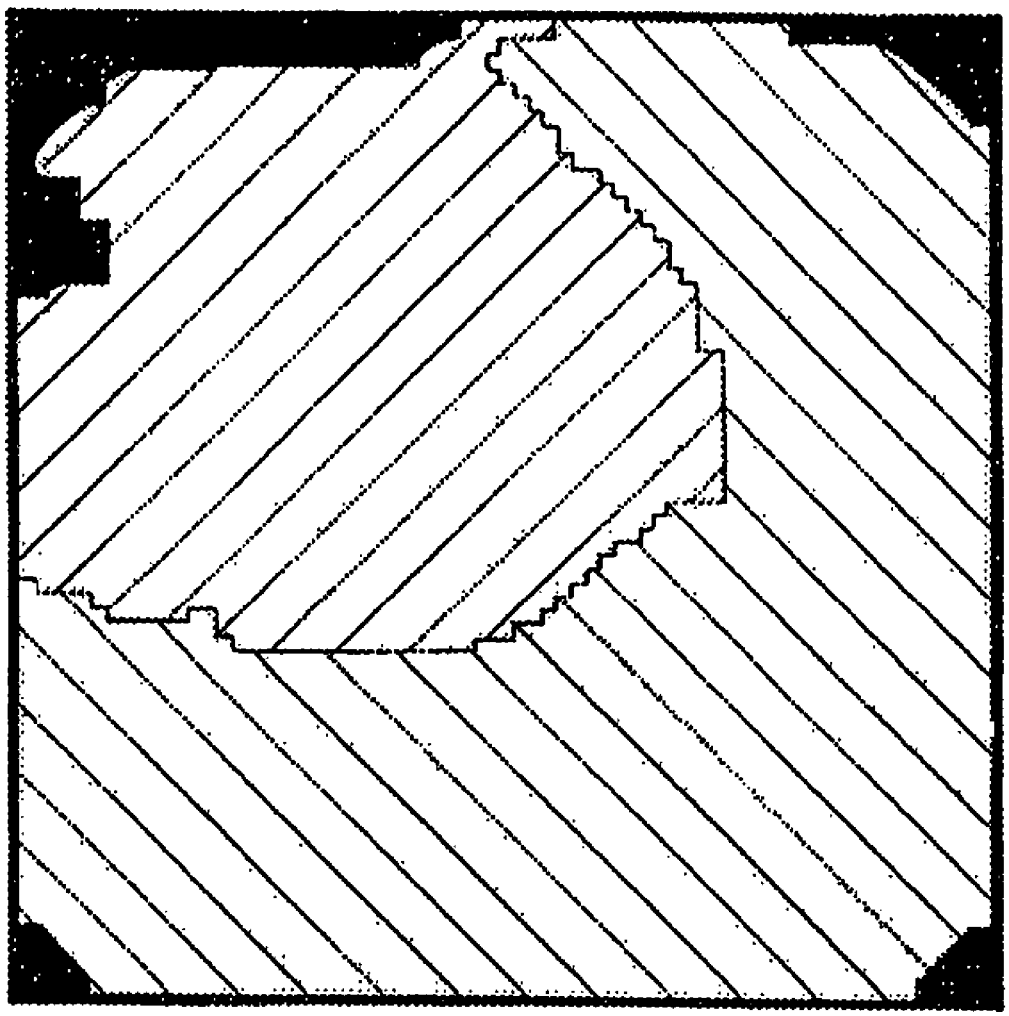
FIG. 18 is a diagram showing an example of a classification result of the image shown in FIG. 17.
Figure 19:
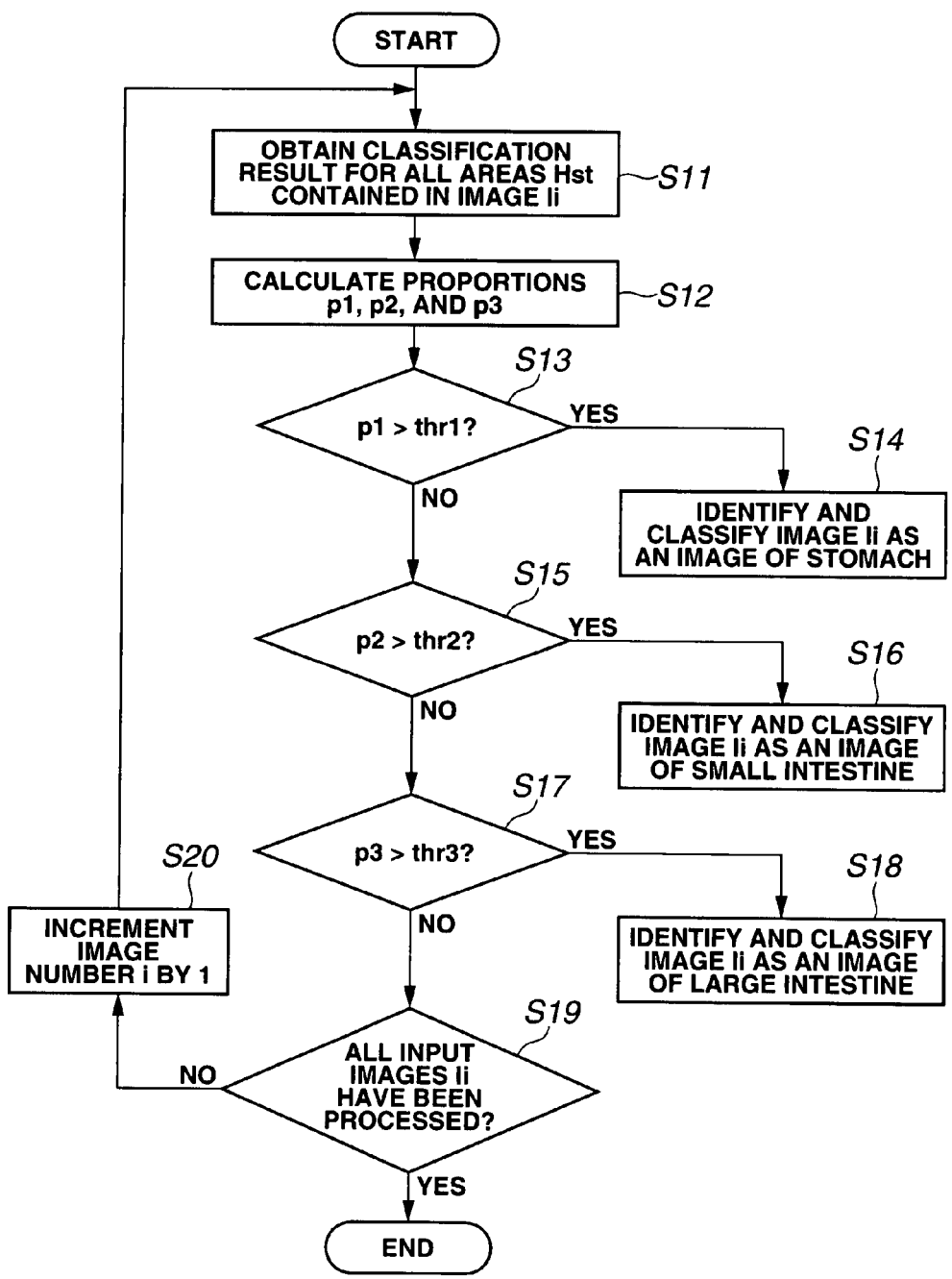
FIG. 19 is a flowchart showing an image processing operation different from that of FIG. 11 in the image processing operation according to the first embodiment.
Figure 20:
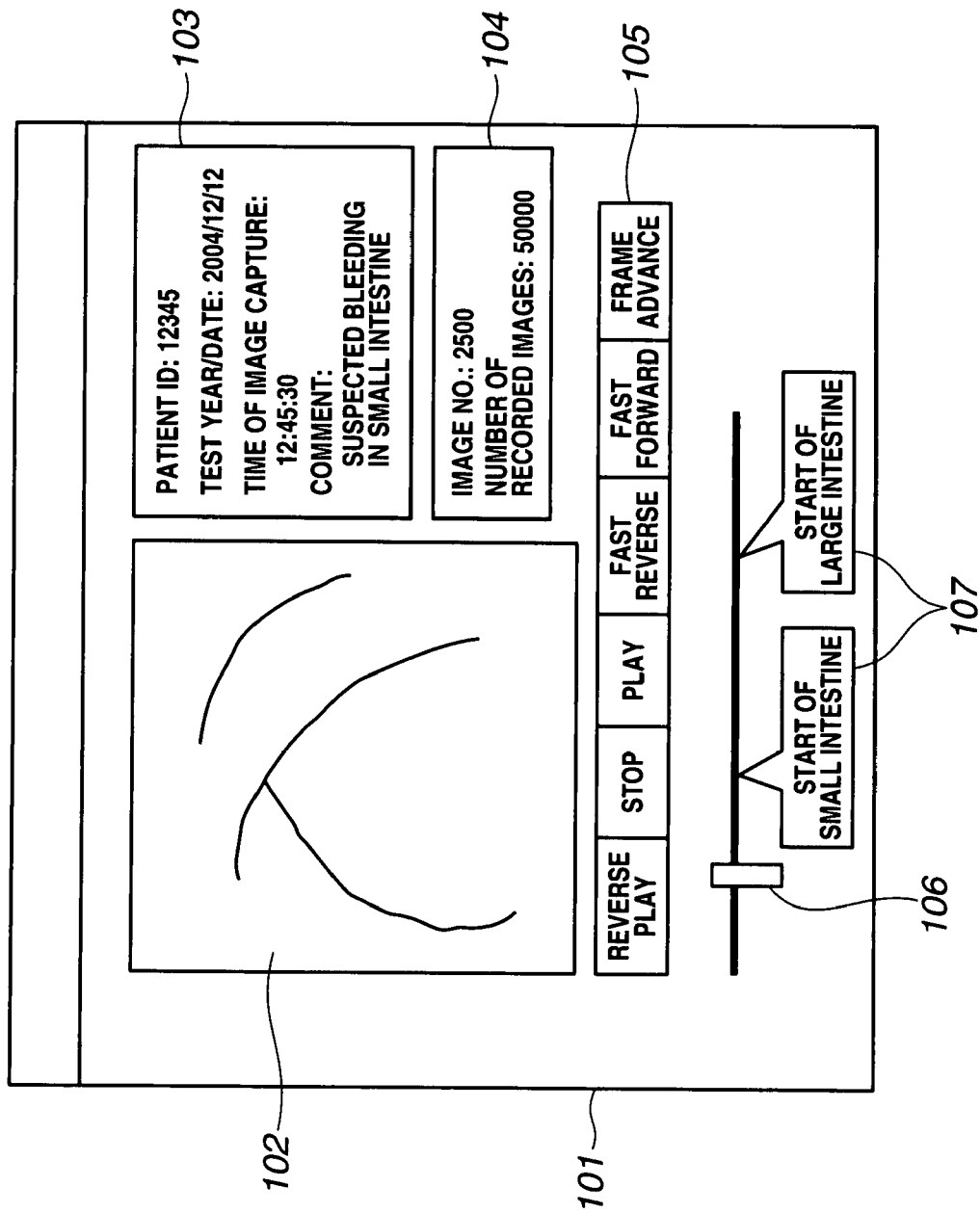
FIG. 20 is a diagram showing an example of a main menu screen in an image of a viewer displayed on the display.

FIGS. 1 through 20 are according to a first embodiment of the invention. FIG. 1 shows an external front view that shows the appearance of an image processing apparatus and peripheral devices for it on which image processing operations according to the first embodiment of the invention are performed. FIG. 2 is an enlarged cross-sectional view that shows primary components by cutting away a portion of a capsule endoscope that generates predetermined image information to be processed by the image processing apparatus of the embodiment. FIG. 3 is a block diagram that shows the general internal configuration of a capsule endoscope device that supplies the image processing apparatus of the embodiment with predetermined image information. FIG. 4 shows an example of usage of the capsule endoscope device that supplies the image processing apparatus of the embodiment with predetermined image information. FIG. 5 illustrates a timing chart that shows an example of a signal output by the capsule endoscope shown in FIG. 2. FIG. 6 illustrates detection of the position of the capsule endoscope shown in FIG. 2. FIG. 7 is an enlarged cross-sectional view of primary components that shows an antenna unit as when the capsule endoscope device shown in FIG. 3 is used. FIG. 8 illustrates a shielding jacket as when the capsule endoscope device shown in FIG. 3 is used. FIG. 9 illustrates an external device of the capsule endoscope device shown in FIG. 3 as being attached on a subject. FIG. 10 is a block diagram showing the electrical configuration of the capsule endoscope shown in FIG. 2. FIG. 11 is a flowchart showing an image processing operation according to the embodiment. FIG. 12 shows an example of division of an input image into (m×n) an image processing operation of the embodiment. FIG. 13 shows an example of an image of gastric mucosa among a plurality of images that constitute training data. FIG. 14 shows an example of an image of villi among a plurality of images constituting training data. FIG. 15 shows an example of an image of feces among a plurality of images that constitute training data. FIG. 16 shows an example of an image of bubbles among a plurality of images that constitute training data. FIG. 17 schematically shows an example of an image of inside of a body cavity that is taken by the capsule endoscope. FIG. 18 shows an example of classification of the image shown in FIG. 17. FIG. 19 is a flowchart showing an image processing operation that is different from the one shown in FIG. 11 in the course of image processing operations of the embodiment. FIG. 20 shows an example of a main menu screen among viewer images shown on a display.

A capsule endoscope device 1 that supplies predetermined image information to the image processing apparatus as the first embodiment of the invention primarily includes a capsule endoscope 3, an antenna unit 4, and an external device 5, as shown in FIG. 3.

As will be described in detail later, the capsule endoscope 3 as a medical device is designed to be swallowed from the mouth of a patient 2 as subject to be positioned in his body cavity, then move through the digestive tract with peristalsis, and has internal functions of capturing images of inside of the body cavity and generating captured image information and of transmitting the captured image information to outside the patient's body. The antenna unit 4 has a plurality of receiving antennas 11 that are positioned on the patient's body and receive the captured image information transmitted by the capsule endoscope 3, as will be described in more detail below. The external device 5 has an outer form of a box, having functions of processing the captured image information received by the antenna unit 4 in various manners, storing the captured image information, and displaying captured images based on the captured image information, as will be described in more detail below. On the outer surface of the external device 5, a liquid crystal monitor 12 for displaying the captured images and an operation unit 13 configured to give operation instructions for various functions.

The external device 5 also has on its outer surface an LED for indicating an alert on remaining charge of a battery for driving power supply and the operation unit 13 configured to include switches such as a power switch. The capsule endoscope 3 internally contains an operation execution unit configured to use a CPU and memory, in which operation execution unit an image processing method of the invention, which will be described later, may be executed for the captured image information that has been received and stored.

The external device 5 is attached on the body of the patient 2 in a detachable manner, and, as shown in FIG. 1, can be mounted on a cradle 6 to be removably connected to the image processing apparatus (hereinafter denoted as a "terminal apparatus") 7 of the first embodiment of the invention. The terminal apparatus 7 may be a personal computer, for example, and it includes a terminal main body 9 that is capable of processing and storing various data, a keyboard 8a and a mouse 8b for inputting various operations, and a display 8c that serves as a display unit configured to display various processing results. As its basic functions, the terminal apparatus 7 is capable of retrieve the captured image information stored in the external device 5 via the cradle 6, writing the information to a rewritable memory built in the terminal main body 9 or a rewritable portable memory such as a semiconductor memory that can be attached to the terminal main body 9, and carrying out image processing for displaying the stored captured image information on the display 8c. The captured image information stored in the external device 5 may also be taken into the terminal device 7 through a USB cable instead of the cradle 6.

Image processing performed by the terminal apparatus 7 may include selection of an image to be displayed in accordance with elapsed time from pieces of captured image information that have been retrieved from the external device 5 and stored in a memory not shown that serves as a storage unit, and processing based on the image processing method of the invention to be discussed below, and they are performed at a control unit 9a included in the terminal main body 9. The control unit 9a may be a CPU and the like, and it can temporarily save results of processing in a register not shown when such processing is carried out.

The appearance and internal structure of the capsule endoscope 3 will be now described with FIG. 2. The capsule endoscope 3 includes an exterior member 14 that has a U-shaped cross section and a cover member 14a that has an approximately hemispherical shape and is formed of a transparent material water tightly attached on the open end of the exterior member 14 with adhesive. Thus, the external appearance of the capsule endoscope 3 is designed to be watertight and have a capsule shape when the exterior member 14 and the cover member 14a are connected to each other.

In an internal hollow unit with the capsule shape formed by the exterior member 14 and the cover member 14a that represents approximately the center of the hemisphere of the cover member 14a, there is positioned an objective lens 15 for collecting an image of an observed site that light is incident through the cover member 14a being accommodated in a lens case 16. At the image-forming position of the objective lens 15, a charge coupled element (hereinafter abbreviated as "CCD") 17 as an imaging element is positioned. Around the lens case 16 containing the objective lens 15, four white LEDs 18 for emitting illumination light are positioned on the same plane (only two LEDs are shown in the figure). Within the internal hollow unit of the exterior member 14 and behind the CCD 17, there are arranged a processing circuit 19 that performs image-capture processing for generation of image capturing signals that have been photoelectric-converted through controlling the driving of the CCD 17, and generation of captured image signals by applying predetermined signal processing to the image capturing signal, and driving of the LEDs 18 for controlling their ON/OFF; a communication processing circuit 20 for converting captured image signals that are generated through the image-capture processing at the processing circuit 19 into radio signals and transmitting the same; a transmission antenna 23 for transmitting the radio signals from the communication processing circuit 20 externally; and a plurality of button batteries 21 for supplying power for driving the processing circuit 19 and the communication processing circuit 20.

The CCD 17, the LED 18, the processing circuit 19, the communication processing circuit 20, and the transmission antenna 23 are arranged on substrates not shown and those substrates are connected to each other by flexible substrates not shown. The processing circuit 19 has an operation circuit not shown for performing image processing to be discussed below. That is, the capsule endoscope 3 includes an image capturing device 43 that has the CCD 17, the LED 18 and processing circuit 19; a transmitter 37 that has the communication processing circuit 20; and the transmission antenna 23.

The specific configuration of the image capturing device 43 of the capsule endoscope 3 will be described with respect to FIG. 10. The image capturing device 43 includes an LED driver 18A for controlling ON/OFF of the LED 18; a CCD driver 17A for controlling the driving of CCD 17 to transfer electric charge that has been photoelectric-converted; a processing circuit 19A for generating image capturing signals using the electric charge transferred from the CCD 17 and applying predetermined signal processing to the image capturing signals to generate captured image signals; a switch unit configured to supply driving power from the batteries 21 to the LED driver 18A, the CCD driver 17A, the processing circuit 19A, and the transmitter 37; and a timing generator 19B for supplying timing signals to the switch unit and CCD driver 17A. The switch unit includes a switch 19C for switching power supply from the batteries 21 to the LED driver 18A, a switch 19D for switching power supply to the CCD 17, the CCD driver 17A and the processing circuit 19A, and a switch 19E for switching power supply to the transmitter 37. To the timing generator 19B, driving power is continuously supplied from the batteries 21.

In the image capturing device 43 of the capsule endoscope 3 having the configuration described above, when the switches 19C, 19D and 19E are off, components except the timing generator 19B are inactive. When a timing signal is output from the timing generator 19B, the switch 19D is turned on, which causes the CCD 17, the CCD driver 17A, and the processing circuit 19 to become active with power supplied from the batteries 21.

After operating the electronic shutter of the CCD 17 to eliminate unnecessary dark current in an early stage of driving of the CCD 17, the timing generator 19B turns the switch 19C on to drive the LED driver 18A, thereby turns on the LED 18 to expose the CCD 17 to light. The LED 18 is turned on for a predetermined time required for exposure of the CCD 17 and then turned off when the switch 19C is turned off for the purpose of reducing power consumption.

Electric charge accumulated during the predetermined time period in which the CCD 17 is exposed to light is transferred to the processing circuit 19A through control of the CCD driver 17A. The processing circuit 19A generates an image capturing signal based on the electric charge transferred from the CCD 17 and applies predetermined signal processing to the image capturing signal to generate an endoscope image signal. When a signal transmitted by the transmitter 37 is of an analog radio system, the processing circuit 19A generates an analog imaging signal that is superimposition of composite synchronizing signal on a CDS output signal and then outputs the analog image capturing signal to the transmitter 37 as endoscope image signal. Or when the signal transmitted by the transmitter 37 is of a digital radio system, the processing circuit 19A further applies encoding such as scrambling to a serial digital signal generated by an analog/digital converter to generate a digital image capturing image signal and outputs the digital imaging signal to the transmitter 37 as endoscope image signal.

The transmitter 37 applies modulation to an analog captured image signal or digital captured image signal, which is an endoscope image signal supplied from the processing circuit 19A, and wirelessly transmits it from the transmission antenna 23 to the outside. Here, the switch 19E is turned on/off by the timing generator 19B so that driving power is supplied to the transmitter 37 only when a captured image signal is output by the processing circuit 19A.

The switch 19E may also be controlled so that driving power is supplied to the transmitter 37 after a predetermined time period has elapsed since a captured image signal is output from the processing circuit 19A. The switch 19E may also be configured to supply power to the transmitter 37 when the endoscope 3 is inserted into the body cavity of the patient 2 as a subject, in response to a signal output by the timing generator 19B based on detection of a predetermined pH value by a pH sensor not shown provided in the capsule endoscope 3, detection of a humidity above a predetermined value by a humidity sensor not shown, detection of a pressure or acceleration above a predetermined value by a pressure or acceleration sensor not shown.

Although the image capturing device 43 of the capsule endoscope 3 normally takes two images per second (2 frames per second=2 fps), when testing an esophagus, for example, it is enabled to take 15 to 30 images per second (15 to 30 fps). To be specific, a timer circuit not shown is provided in the capsule endoscope 3, and by means of the timer circuit, driving of the image capturing device 43 is controlled so that high-speed image capturing that takes many images per second is carried out until the timer reaches a predetermined count and low-speed image capturing for taking less images per second is carried out after elapse of the predetermined time period. Alternatively, the timer circuit may be activated upon power-up of the capsule endoscope 3, and the timer circuit can control driving of the image capturing device 43 to perform high-speed image capturing for the time period immediately after the patient swallowing the capsule endoscope 3 to the endoscope 3 passing through the esophagus, for example. Furthermore, a capsule endoscope for low-speed image capturing and one for high-speed image capturing may be separately provided and selectively used according to which site is observed.

Hereinafter, the antenna unit 4 that is placed on the patient 2's body will be described. As shown in FIG. 4, when an endoscope test is carried out by the patient swallowing the capsule endoscope 3, the patient 2 wears a jacket 10 on which the antenna unit 4 including the receiving antennas 11 is attached. The antenna unit 4 positions the receiving antennas 11 which are unidirectional like a patch antenna used for GPS such that their directionality is oriented inward the body of the patient 2, as shown in FIG. 7. That is, since a capsule main body 3D of the capsule endoscope 3 is left within the body, the antennas 11 are positioned surrounding the capsule main body 3D in the body. By using the antennas 11 of high directionality, the antennas are made less susceptible to effect of interference caused by radio wave not originating from the capsule main body 3D in the body.

As shown in FIG. 8, the jacket 10 includes the antenna unit 4 to be attached on the body of the patient 2 and a shielding jacket 72 formed of an electromagnetic shielding fabric that covers a main body unit 5D of the external device 5 which is attached on the waist of the patient 2 with a belt. The electromagnetic shielding fabric forming the shielding jacket 72 may be a metallic, metal-chemical or copper sulfide-containing fabric. The shielding jacket 72 is not limited to the form of a jacket: it may be formed as a vest or dress.

The external device 5 may be attached on the shielding jacket 72 by providing a keyhole 74 on the external main body 5D of the external device 5 and inserting a key 75 provided on the shielding jacket 72 into the keyhole 74 so as to mount it removably on the belt 73 as shown in FIG. 9. Alternatively, a pocket not shown may be simply provided on the shielding jacket 72 and the external main body 5D may be put in it, or pieces of magic tape (a registered trademark) may be attached on the external main body 5D of the external device 5 and the shielding jacket 72, and the external device 5 may be fixed with the magic tape (a registered trademark).

In short, by covering the body on which the antenna unit 4 is attached with the shielding jacket 72, external radio wave to the antenna unit 4 is shielded so as to make the antenna unit 4 further less susceptible to effect of interference caused by external radio wave.

In the following, the configuration of the antenna unit 4 and the external device 5 will be described with reference to FIG. 3. The antenna unit 4 includes receiving antennas 11a to 11d for receiving radio signals transmitted by the transmission antenna 23 of the capsule endoscope 3 and an antenna selector switch 45 for switching among the antennas 11a to 11d. The external device 5 includes a reception circuit 33 for reception processing such as conversion of radio signals from the antenna selector switch 45 into captured image signals and amplification; a signal processing circuit 35 for applying predetermined signal processing to the captured image signals supplied from the reception circuit 33 to generate display signals and captured image data for a captured image; a liquid crystal monitor 12 for displaying a captured image based on the captured image display signal generated by the signal processing circuit 35; a memory 47 for storing the captured image data generated at the signal processing circuit 35; and an antenna selection circuit 46 for controlling the antenna selector switch 45 according to the magnitude of a radio signal received by the reception circuit 33.

The receiving antennas 11 indicated as the receiving antennas 11a to 11d of the antenna unit 4 in the figure receive radio signals that are transmitted at a predetermined radio wave strength from the transmission antenna 23 of the capsule endoscope 3. A receiving antenna for receiving the radio signals is switched among the receiving antennas 11a to 11d through control of the antenna selector switch 45 with an antenna selection signal from the antenna selection circuit 46 of the external device 5. That is, radio signals received by each of the receiving antennas 11a to 11d that are switched by the antenna selector switch 45 sequentially are output to the receiver 33. The receiver 33 detects the reception strength of radio signals for each of the receiving antennas 11a to 11d to calculate the positional relationship between the receiving antennas 11a to 11d and the capsule endoscope 3, and also demodulates the radio signals and outputs captured image signals to the signal processing circuit 35. The antenna selection circuit 46 is controlled with output from the receiver 33.

The operation of the antenna selector switch 45 by the antenna selection circuit 46 will be described. It is assumed that radio signals transmitted by the capsule endoscope 3 alternately includes a strength receiving period in which reception strength signals indicating the reception strength of radio signals are transmitted and a picture signal period in which captured image signals are transmitted, within a period in which one frame of captured image signals is transmitted, as shown in FIG. 5.

The antenna selection circuit 46 is supplied with the reception strength of a reception strength signal received by each of the receiving antennas 11a to 11d via the reception circuit 33. The antenna selection circuit 46 compares strength of reception strength signals from each of the antennas 11a to 11d supplied by the receiver 33 with each other to determine an optimal receiving antenna for receiving captured image signals in the picture signal period, that is, an antenna 11i (i=a to d) that has the strongest reception strength signal, and generates and outputs a control signal for switching the antenna selector circuit 45 to that antenna 11i. Consequently, when reception strength of a reception strength signal from another antenna is higher than that from the antenna currently receiving image signals, the receiving antenna for use in the picture signal period will be changed from the next frame.

In this manner, reception strength of a captured image signal or a reception strength signal is compared every time a radio signal from the capsule endoscope 3 is received, and based on the comparison, the antenna selection circuit 46 specifies the antenna 11i that has the largest reception strength as an antenna for receiving image signals. Consequently, even when the capsule endoscope 3 moves within the body of the patient 2, it is possible to receive image signals gained by an antenna 11 that is able to detect signals of the largest reception strength at the current position. Since the capsule endoscope 3 moves within the body either at a very low speed or a high speed, a single switching of antenna is not necessarily performed in one image capturing operation; the antenna switching operation may be performed once in a number of image capturing operations when in high-speed image capturing mode and the like.

Since the capsule endoscope 3 moves within the body of the patient 2, the external device 5 may send a detection result signal which represents a result of radio wave strength detection to the capsule endoscope 3 at certain intervals, and the capsule endoscope 3 may update its output power in transmission based on the signal. This makes it possible to set an appropriate transmission output even when the capsule endoscope 3 moves in the body of the patient 2, to prevent unnecessary consumption of the energy of the batteries 21, and to maintain condition of signal transmission/reception in an appropriate condition.

The following description will illustrate with FIG. 6 how to obtain information that indicates the positional relationship between the receiving antennas 11 and the capsule endoscope 3. The description will refer to a case where the capsule endoscope 3 is set at the origin of three-dimensional coordinates X, Y and Z in FIG. 6. For the sake of brevity, three receiving antennas 11a, 11b and 11c are used out of the receiving antennas 11a to 11d, and the distance between the receiving antennas 11a and 11b is represented as Dab, the distance between the receiving antennas 11b and 11c as Dbc, and the distance between the receiving antennas 11a and 11c as Dac. In addition, the receiving antennas 11a to 11c and the capsule endoscope 3 have a predetermined distance relation between them.

Reception strength of a radio signal having a certain transmission strength transmitted by the capsule endoscope 3 as received by each of the receiving antennas 11j (j=a, b, c) is a function of distance Li (i=a, b, c) from the capsule endoscope 3 (i.e., the transmission antenna 23 of the capsule endoscope 3). More specifically, the reception strength is dependent on the distance Li with a radio wave attenuation amount involved. Accordingly, the distance Li between the capsule endoscope 3 and each of the receiving antennas 11j is calculated from the reception strength of a radio signal transmitted from the capsule endoscope 3 as received by the receiving antenna 11j. To determine the distance Li, relevant data such as attenuation amount of radio wave as a function of the distance between the capsule endoscope 3 and the receiving antenna 11j is preset in the antenna selection circuit 46. Calculated distance data indicating the positional relationship between the capsule endoscope 3 and each receiving antenna 11j is stored in the memory 47 as position information of the capsule endoscope 3. Captured image information and position information for the capsule endoscope 3 stored in the memory 47 are useful for setting the position of observation with the endoscope in an image information processing method, which will be discussed later, that is implemented by the terminal apparatus 7.

In the following, image processing operations on the image processing apparatus of the present invention will be described.

This embodiment assumes that an image of inside of a body cavity image-captured by the capsule endoscope 3 has a size of ISX×ISY (values that meet $1 \leq ISX$, $1 \leq ISY$, e.g., ISX=300 and ISY=300), and an image includes three planes of RGB and one pixel in each plane is 8 bits, that is, a pixel assumes a value between 0 and 255. It is also assumed in this embodiment that the ith image of N images ($1 \leq N$) that are image-captured temporally successively is denoted as Ii ($1 \leq i \leq N$) and its RGB planes are denoted as Ri, Gi, and Bi, respectively. In addition, in this embodiment, the kth pixel in each plane ($1 \leq k \leq ISX \times ISY$) is denoted as rik, gik and bik, respectively.

Image processing operations in the image processing apparatus of the embodiment are carried out as processing at the control unit 9a contained in the terminal main body 9 of the terminal apparatus 7 described above.

The control unit 9a, which serves as an image signal input unit and an image inputting unit, first inputs an image signal that is based on an image of inside of a body cavity captured by the capsule endoscope 3, applies noise removal by way of media filtering and inverse γ correction, for example, as pre-processing to each of Ri, Gi, and Bi planes that constitute the inputted ith image Ii, and also detects halation pixels and dark pixels through processing based on threshold values in order to exclude them from subsequent processing (step S1 in FIG. 11). The processing based on the threshold values may determine that a pixel is a dark pixel if density values of rik, gik and bik are all below 10 and is a halation pixel if all of density values of rik, gik and bik are above 230, for example.

The control unit 9a, which serves as an image division unit and an area definition unit, subsequently divides each of the planes Ri, Gi, and Bi into small areas (step S2 in FIG. 11). In this embodiment, as shown in FIG. 12, the control unit 9a divides each of Ri, Gi, and Bi planes into rectangle areas each of which contains lx pixels in an x-axis direction×ly pixels in a y-axis direction ($1 \leq lx$, $1 \leq ly$), and there are (m×n) areas (m=ISX/lx and n=ISY/ly). When m or n cannot be an integer, the control unit 9a handles an outermost area that has a size of a decimal fraction as an area that has a decimal fraction number of pixels or excludes it from subsequent processing.

The control unit 9a, which serves as a feature value calculation unit, calculates as feature values color information that reflects difference in color on an image of the object and texture information that reflects difference in structure on the image of the object in the divided areas (step S3 in FIG. 11). In the following description, one of the areas divided by the control unit 9a will be denoted as Hst ($1 \leq s \leq m$, $1 \leq t \leq n$).

The color information calculated by the control unit 9a in this embodiment is values represented as two feature values including the average value of gik/rik (hereinafter denoted as µgst) and the average value of bik/rik (hereinafter "µbst") that are based on ratio of RGB values of each pixel contained in one area Hst. The values µgst and µbst assume a value between 0 and 1. The values µgst and µbst similarly assume small values in an area that exhibits a relatively reddish color such as gastric mucosa, for example. On the other hand, the values µgst and µbst assume large values close to each other in an area that exhibits relatively a whitish color such as small intestine, for example. The values µgst and µbst assume values of the relation µgst>µbst in an area that exhibits a relatively yellow color such as feces, for example.

The texture information calculated by the control unit 9a in this embodiment reflects difference in structure in an image of an object as mentioned above. Structures in an image of the object are represented as a minute structure of villi on mucosa surface as well as an irregular pattern of feces, for example. Specifically, the texture information calculated by the control unit 9a is coefficients of variation for RGB values represented as three feature values, CVrst, CVgst, and CVbst, which are standard deviations of RGB value σrst, σgst, and σbst for each pixel contained in one area Hst divided by average values of RGB values mrst, mgst, and mbst for each pixel contained in one area Hst. Formulas for calculating the coefficients of variation CVrst, CVgst, and CVbst are represented as Formulas (1), (2), and (3) below:

$$CVrst = \sigma rst/mrst \quad (1)$$

$$Cvgst = \sigma gst/mgst \quad (2)$$

$$CVbst = \sigma bst/mbst \quad (3)$$

The coefficients of variation CVrst, CVgst, and CVbst calculated with the Formulas (1), (2) and (3) make it possible to numerically represent degree of pixel variation due to a texture structure without being effected by variation in amount of illumination light supplied to the object. In an area that has a relatively flat structure in an image, such as gastric mucosa, image-captured during normal observation in which enlarged observation is not carried out, the values CVrst, CVgst, and CVbst similarly assume small values because such an area does not have a distinct texture structure. On the other hand, in an area that contains relatively many edges on an image such as villi of small intestine, for example, the values CVrst, CVgst, and CVbst similarly assume large values.

Although subsequent processing carried out by the control unit 9a of the embodiment uses the five feature values including the color information and the texture information, values constituting the feature values may be changed or added according to the user's application. For example, the control unit 9a may use ratios among rik, gik, and bik in one pixel of one area that are represented as chromaticity, that is, values of rik/(rik+gik+bik), gik/(rik+gik+bik), and bik/(rik+gik+bik), to conduct subsequent processing, instead of the values µgst and µbst as the color information.

The control unit 9a then calculates the five feature values that include the color and texture information, i.e., µgst, µbst, CVrst, CVgst, and CVbst, in each of (m×n) areas Hst based on RGB values of each pixel excluding halation pixels and dark pixels. In this embodiment, if the proportion of the total number of halation pixels and dark pixels exceeds 50%, for example, of (lx×ly) pixels contained in one area Hst, control for excluding the area Hst from subsequent processing may be provided.

Then, the control unit 9a, which serves as an area division unit, identifies the image-captured object of each area by executing identification and classification based on the five feature values calculated for each area Hst, and classifies each area Hst based on the identification.

Specifically, based on images such as ones shown in FIGS. 13, 14, 15 and 16 that are prepared as images constituting training data for four classes including gastric mucosa, villus, feces, and bubble, the control unit 9a first calculates the five feature values that are determined for each area of the image and then creates a linear discriminant function for each of the four classes. The control unit 9a uses the linear discriminant function as a classifier calculated in the above-described manner to identify one of the four classes, i.e., gastric mucosa, villus, feces, and bubble, to which the area Hst belongs and classifies the area Hst according to the identification. By performing such identification and classification to all areas Hst contained in the image Ii, the control unit 9a obtains a classification result such as shown in FIG. 18 which separates the image into villus and bubbles when an image shown in FIG. 17 is input (step S4 in FIG. 11).

Identification and classification made by the control unit 9a of this embodiment for each area of an image using the classifier is not limited to by means of the linear discriminant function, but they may be performed by means of quadratic discriminant function or neural network, for example. Although the control unit 9a identifies and classifies each area of an input image into one of the four classes, i.e., gastric mucosa, villus, feces, and bubble, in this embodiment, the number and kinds of classes for classification can be changed or added as appropriate for the user's application and the like. The control unit 9a may also classify areas into esophagus or large intestine mucosa class in addition to the four classes illustrated above, or may perform classification handling duodenum and villus as independent classes.

The control unit 9a, which also serves as a division determination value calculation unit, calculates a value p which represents the proportion of the total number of areas z which have been classified as a biological mucosa surface, that is, as gastric mucosa or villus, to the total number of areas (m×n) in the image Ii based on the classification result according to Formula (4) below (step S5 in FIG. 11):

$$p = z/(m \times n) \quad (4)$$

Then, the control unit 9a, which serves as an image classification unit, compares the proportion value p determined with Formula (4) with a threshold value thr in order to determine whether the image Ii captures the biological mucosa surface adequately. If the control unit 9a determines that the proportion value p in the image Ii is greater than the threshold value thr (step S6 in FIG. 11), it determines that the image Ii captures the biological mucosa surface adequately, that is, it identifies and classifies it as an image that requires observation, and sets a flag value flagi as a reference value to 1 (step S7 in FIG. 11). In this embodiment, the value of threshold thr may be 0.5, for example.

If the control unit 9a detects that the proportion value p in the image Ii is below the threshold thr (step S6 in FIG. 11), it determines that the image Ii is an image that does not image-capture the biological mucosa surface adequately due to the presence of feces and bubbles, that is, it identifies and classifies the image as an image that does not require observation, and sets the flag value flagi to 0 (step S8 in FIG. 11).

Subsequently, if the processing described above has not been completed for all of input images Ii (step S9 in FIG. 11), the control unit 9a increments the image number i by 1 (step S10 in FIG. 11), and continues to perform the processes shown at steps S1 to S9 of FIG. 11 to the next image.

By performing such processing described above, the control unit 9a, which serves as an image display control unit, is able to display only images with the flag value flagi of 1 that require observation on the display 8c and not display images having the flag value flagi of 0 that do not require observation on the display 8c based on the flag value of flagi when the user observes images of the object. The control unit 9a which also serves as an image deletion unit may also delete images that the have the flagi value of 0 and thus do not require observation so as to reduce the size of image data to be stored.

In the processing shown at step S5 in FIG. 11, the control unit 9a calculates the proportion p from the total number of areas z that have been classified as gastric mucosa or villus. However, the processing performed by the control unit 9a is not limited thereto; the control unit 9a may also handle the number of areas z1 that are classified as gastric mucosa and the number of areas z2 that are classified as villus separately as will be mentioned below.

In that case, the control unit 9a calculates the value of proportion p of the total number of areas that have been classified as gastric mucosa or villus (z1+z2) to the total number of areas in the image Ii (m×n) according to Formula (5) below at step S5 in FIG. 11:

$$p=(z1+z2)/(m\times n) \qquad (5)$$

The control unit 9a may also calculate the proportion of the number of such areas to the total number of areas in the images Ii (m×n) for each class separately based on the number of areas classified into each class.

The control unit 9a first performs the processing from steps S1 to S4 of FIG. 11 to obtain classification results for all areas Hst contained in the image Ii (step S11 of FIG. 19). Denoting the number of areas classified as gastric mucosa as z1, the number of areas classified as villus as z2, and the number of areas classified as feces as z3, the control unit 9a calculates a proportion p1 of the number of areas z1 classified as gastric mucosa to the total number of areas (m×n) in the image Ii, a proportion p2 of the number of areas z2 classified as villus to the total number of areas (m×n) in the image Ii, and a proportion p3 of the number of areas z3 classified as feces to the total number of areas (m×n) in the image Ii according to Formula (4) (step S12 in FIG. 19)

The control unit 9a then compares the value of proportion p1 with a threshold value thr1. If it determines that the proportion p1 in the image Ii is greater than the threshold value thr1 (step S13 of FIG. 19), the control unit 9a, which serves as an image classification unit, identifies and classifies the image Ii as an image of stomach as an object (step S14 of FIG. 19). In this embodiment, the threshold value thr1 may be 0.8, for example.

Further, if it detects that the value of proportion p1 in the image Ii is equal or below the threshold value thr1 (step S13 in FIG. 11), the control unit 9a then compares the proportion p2 with a threshold value thr2. If it determines that the proportion p2 in the image Ii is greater than the threshold value thr2 (step S15 in FIG. 19), the control unit 9a, which serves as an image classification unit, identifies and classifies the image Ii as an image of (villi of) small intestine as an object (step S16 in FIG. 19). In this embodiment, the threshold value thr2 may be 0.8, for example.

If it determines that the proportion p2 in the image Ii is equal or below the threshold value thr2 (step S15 in FIG. 11), the control unit 9a then compares the proportion p3 with a threshold value thr3. If it determines that the value of proportion p3 in the image Ii is greater than the threshold value thr3 (step S17 in FIG. 19), the control unit 9a, which serves as an image classification unit, identifies and classifies the image Ii as an image of large intestine as an object because feces has a large proportion in the image Ii (step S18 in FIG. 19). In this embodiment, the threshold value thr3 may be 0.8, for example.

Thereafter, the control unit 9a suspends identification and classification of images that have not been identified and classified as an image of gastric mucosa, villus, or feces in the previous processing. If the processing described above has not been completed for all of input images Ii (step S9 in FIG. 19), the control unit 9a increments the image number i by 1 (step S20 in FIG. 19) and continues to perform the processing shown at steps S11 to S19 of FIG. 19 to the next image.

Through execution of the processing from steps S11 to S19 in FIG. 19, the control unit 9a identifies the images that have been identified and classified as images of small intestine and ones of large intestine. In other words, the control unit 9a can determine whether an organ image-captured as an object is the stomach, small intestine, or large intestine by performing the processing from steps S11 to S19 of FIG. 19 described above.

When the user observes images of objects, a viewer having a GUI such as one shown in FIG. 20 appears on the display 8c of the terminal apparatus 7. A main screen 101 of the viewer shown in FIG. 20 includes an image display unit 102 in which an image of an object is displayed, a patient/test information display unit 103 in which information on a patient and a test is displayed, an image information display unit 104 in which the number of images and the like is indicated, an image display control unit 105 configured to control display in the image display unit 102, and a slider 106.

The slider 106 is capable of displaying a desired image in the image display unit 102 based on an instruction given by using a mouse cursor not shown. The slider 106 also has guide indicators 107 which indicate starting points of the images of small intestine and ones of large intestine. Thus, the user can easily observe a desired site within a body cavity, e.g., to observe the small intestine first and efficiently in a case of suspected bleeding from the small intestine, for example. On the main screen 101 of the viewer shown in FIG. 20, a button indicated as "small intestine" not shown may be provided. In that case, the user can directly display and observe the image of small intestine by clicking on the button with the mouse cursor not shown.

Although the control unit 9a of the terminal apparatus 7 divides the image Ii into rectangle areas each of which includes lx pixels in the x-axis direction×ly pixels in the y-axis direction in the image processing method of the embodiment, it may perform similar processing with an area having a size of lx/2 pixels in the x-axis direction and ly/2 pixels in the y-axis direction overlapped on the rectangle area. In that case, it is possible to reduce misclassification that can occur when a border between the classes for classification is included in the rectangle area.

As mentioned above, the control unit 9a of the terminal apparatus 7 performs identification and classification handling gastric mucosa and villus as independent classes using the image processing method of the embodiment. However, the control unit 9a may also identify and classify gastric mucosa and villus as one class of "biological mucosa surface" and subsequently re-identify and classify the areas Hst classified as "biological mucosa surface" into two classes of gastric mucosa and villus.

The capsule endoscope 3 moves from the stomach to the small intestine in sequence after being placed in a body. Thus, the control unit 9a of the terminal apparatus 7 may stop classification into the gastric mucosa class at the point in which the proportion of areas classified as villus to the total number of areas has exceeded 0.7 based on the classification results obtained.

The image processing method of the embodiment may also be employed for the purpose of realizing a classifier that is based on the difference in color and pattern of a mucosa surface by setting an esophagus class and a large intestine class, for example. Furthermore, the image processing method of the embodiment may also be employed to identify areas as the large intestine when areas classified as feces has a large proportion to the total number of areas and areas classified as villus has a small proportion to the total number of areas.

As has been thus described, according to the image processing method of the embodiment, it is possible to identify and classify images of gastric mucosa and villus as a biological mucosa surface and images of feces and bubbles as foreign matters or non-biological mucosa that are different from a biological mucosa surface on a per-image basis, and display only images that require observation on the display 8c. Consequently, the user can observe inside of body cavities excluding images that do not image-capture biological mucosa surfaces well, which can improve efficiency of observation using the capsule endoscope device 1.

The image processing method of the embodiment can determine whether a result of lesion site detection has been obtained from a biological mucosa surface or not when used in combination of an image processing method for detecting a lesion site such as bleeding or redness, which can improve accuracy of legion site detection. Specifically, the control unit 9a of the terminal apparatus 7 can enhance accuracy of lesion site detection by using an image processing method for detecting a lesion site such as bleeding and redness, making reference to the classification result of area Hst that has been extracted as an area having a suspected lesion, and handling it as a misdetection if the area is classified as an image of non-biological mucosa surface such as feces and bubbles.

In addition, according to the embodiment, by further using an image processing method for classifying images into ones of normal mucosa and ones of lesion sites based on feature values of each area, for example, for each area classified as an image of biological mucosa surface, it is possible to improve accuracy of lesion site detection.

Second Embodiment

Figure 21:
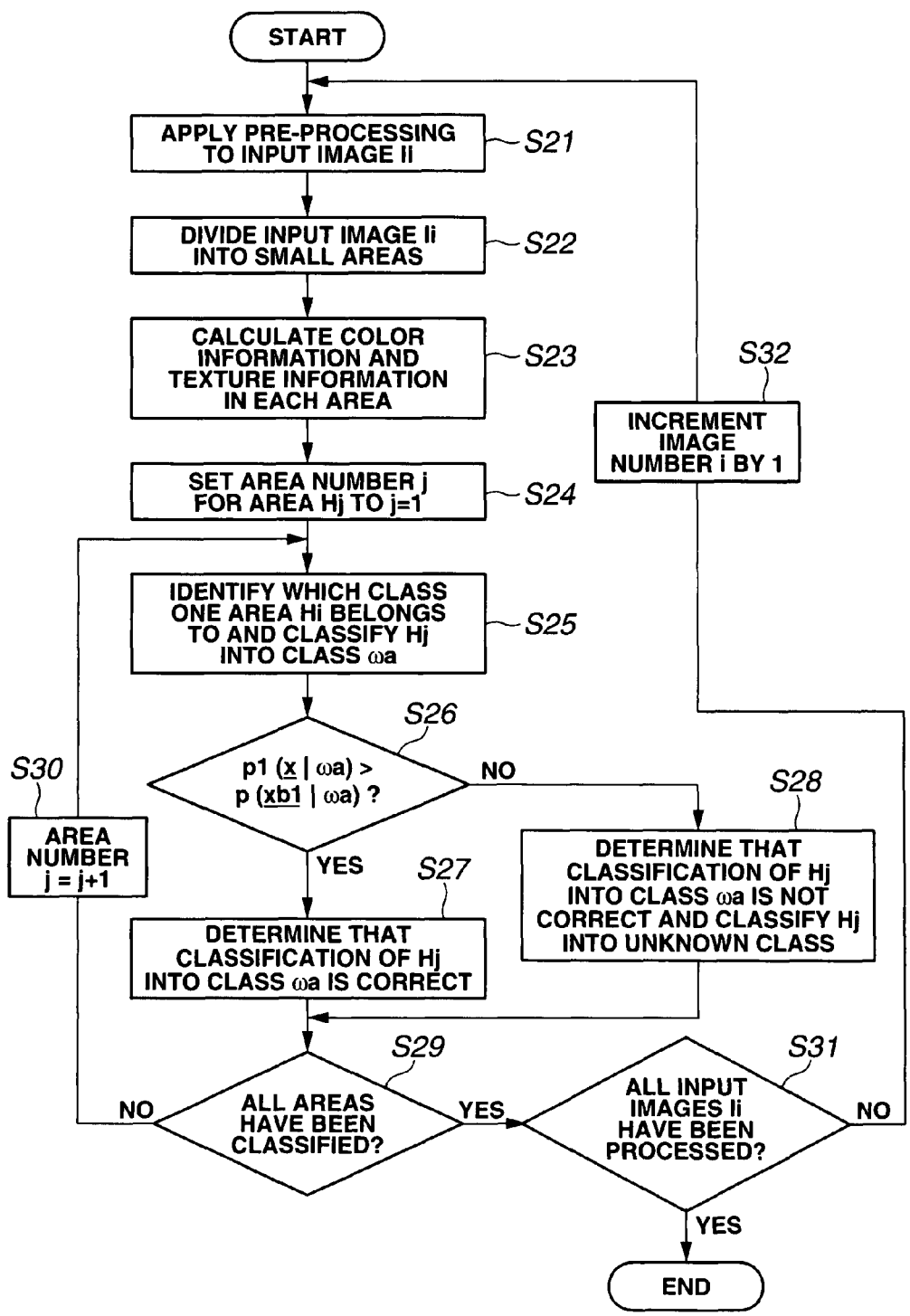
FIG. 21 is a flowchart showing an image processing operation according to a second embodiment.

FIG. 21 is according to a second embodiment of the invention. Detailed description will be omitted for components that have a similar configuration as in the first embodiment. The same reference numerals are used to indicate components similar to those of the first embodiment and description on them are omitted. A capsule endoscope device 1 of the present embodiment has a similar configuration to the first embodiment and an image processing method of the embodiment is also realized as a program that is executed on a personal computer, for example, as a terminal apparatus 7. The image processing method of the embodiment is implemented as processing at a control unit 9a of the terminal main body 9.

FIG. 21 is a flowchart illustrating image processing operations of the embodiment.

The control unit 9a first inputs an image signal that is based on an image of inside of a body cavity captured by a capsule endoscope 3, and applies noise removal by means of median filtering and inverse γ correction, for example, as preprocessing to each of Ri, Gi, and Bi planes that constitute the input ith image Ii and also detects halation and dark pixels through processing based on the threshold values in order to exclude them from subsequent processing (step S21 in FIG. 21). The processing based on the threshold values may determine that a pixel is a dark pixel if all of density values of rik, gik, and bik are below 10 and is a halation pixel if all of density values of rik, gik, and bik are above 230, for example.

Then, the control unit 9a divides each of Ri, Gi and Bi planes into small areas (step S22 in FIG. 21). In this embodiment, as with the method implemented in the first embodiment, the control unit 9a divides each of Ri, Gi, and Bi planes into rectangle areas each of which contains lx pixels in an x-axis direction×ly pixels in a y-axis direction ($1 \leq lx$, $1 \leq ly$) and there are (m×n) areas (m=ISX/lx, n=ISY/ly). When m or n cannot be an integer, the control unit 9a handles an outermost area that has a size of a decimal fraction as an area that has a decimal fraction number of pixels or excludes it from subsequent processing.

In each of the divided areas, the control unit 9a calculates color information that reflects difference in color in an image of an object and texture information that reflects difference in structure in the image of the object as feature values (step S23 in FIG. 21). In the image processing method of this embodiment, one of areas divided by the control unit 9a is denoted as Hj($1 \leq j \leq m \times n$).

In this embodiment, the color information calculated by the control unit 9a is values represented as two feature values that include the average of gik/rik (hereinafter denoted "μgj") and the average of bik/rik (hereinafter "μbj") that are based on a ratio of RGB values of each pixel contained in one area Hj. Each of the values μgj and μbj assume a value between 0 and 1. Each of the values μgj and μbj similarly assume a small value in an area that exhibits a relatively reddish color such as gastric mucosa, for example. On the other hand, the values μgj and μbj similarly assume large values in an area that exhibits a relatively whitish color such as small intestine, for example. The values μgj and μbj assume values of the relation μgj>μbj in an area that exhibits a relatively yellowish color such as feces.

In this embodiment, the texture information calculated by the control unit 9a reflects difference in structure in an image of an object as mentioned above. Structures in an image of an object are represented as minute structures such as villi on mucosa surface and as irregular patterns of feces. More specifically, the texture information calculated by the control unit 9a is coefficients of variation for RGB values, CVrj, CVgj, and CVbj, that are represented as three feature values that are obtained by dividing standard deviations σrj, σgj, and σbj of RGB values of each pixel contained in an area Hj by average values, mrj, mgj, and mbj of RGB values of each pixel contained in that area Hj. Formulas for calculating the coefficients of variation CVrj, CVgj, and CVbj are represented as Formulas (6), (7), and (8) below:

$$CVrj = \sigma rj/mrj \quad (6)$$

$$CVgj = \sigma gj/mgj \quad (7)$$

$$CVbj = \sigma bj/mbj \quad (8)$$

With the coefficients of variation CVrj, CVgj, and CVbj calculated with the Formulas (6), (7) and (8), it is possible to numerically represent degree of pixel variation due to a texture structure without being effected by difference in amount of illumination light supplied to the object. The CVrj, CVgj, and CVbj similarly assume small values in an area that has a relatively flat structure in an image of such as gastric mucosa captured during normal observation in which enlarged observation is not performed, for example, because such an area does not have obvious texture structures. On the other hand, CVrj, CVgj, and CVbj similarly assume large values in an area that contains relatively many edges in the structure of an image such as villi of small intestine, for example.

The control unit 9a then calculates five feature values that includes the color and the texture information, that is, µgj, µbj, CVrj, CVgj, and CVbj, in each of (m×n) areas Hj based on RGB values of each pixel except halation and dark pixels. In this embodiment, if the proportion of the total number of halation pixels and dark pixels exceeds 50% of (lx×ly) pixels contained in one area Hj, for example, control for excluding the area Hj from subsequent processing may be provided.

Then, the control unit 9a sets the area number j for the area Hj to j=1 in order to implement processing described below (step S24 in FIG. 21). The control unit 9a uses a statistical classifier based on Bayes' theorem to identify one of the four classes, i.e., gastric mucosa, villus, feces, and bubbles, to which the area Hj belongs, and classifies the area Hj based on the identification.

Specifically, denoting a prior probability that one class ωa (a=1, 2, ..., C, C representing the number of classes) occurs in identification and classification into the four classes as P(ωa); feature vector that is determined from the five feature values in one area Hj as x; a probability density function based on the occurrence probability of the feature vector x from all the classes as p(x); and a conditional probability density (multivariate normal probability density) function based on the occurrence probability of the feature vector x from one class ωa as p(x|ωa), a formula for calculating posterior probability P(ωa|x) that the feature vector x that has occurred belongs to one class ωa is represented as Formula (9) below:

$$P(\omega a|x) = p(x|\omega a)P(\omega a)/p(x) \quad (9)$$

The conditional probability density function p(x|ωa) and the probability density function p(x) are represented as Formulas (10) and (11) below:

$$p(x|\omega a) = (1/((2\pi)^{d/2}|\Sigma a|^{1/2}))\exp[(-\tfrac{1}{2})(x-\mu a)^t \Sigma a^{-1}(x-\mu a)] \quad (10)$$

$$p(\underline{x}) = \sum_{a=1}^{C} p(\underline{x}|\omega a)P(\omega a) \quad (11)$$

In Formulas (10) and (11), d represents the number of dimensions that is equal to the number of feature values of x, and µa and Σa represent the average vector of feature vector x in the class ωa and a variance-covariance matrix in one glass ωa, respectively. $(x-\mu a)^t$ represents the transposed matrix of (x-µa), |Σa| represents the determinant of Σa, and $\Sigma a^{-1}$ represents the inverse matrix of Σa. For the sake of brevity, it is also assumed that the prior probability P(ωa) assumes the same value in all classes and that the probability density function p(x) is represented by Formula (11) as a function that is common in all classes.

The average vector µa and the variance-covariance matrix Σa as references of classification are factors that constitute the population parameter in one class ωa, and they are calculated for each class from the feature vector x that is determined for each area of an image based on a plurality of images that constitute training data for the four classes including gastric mucosa, villus, feces, and bubble classes, e.g., images such as ones shown in FIGS. 13, 14, 15 and 16, at a stage prior to input of the first image Ii to the terminal apparatus 7, and then stored in the terminal apparatus 7 as initial values.

The average vector µa is a vector that is formed of average values of the five feature values of the feature vector x and that has the same number of dimensions as the feature vector x. That is, denoting the feature vector x as x=(x1, x2, x3, x4, x5), the average vector µa is represented as µa=(µx1, µx2, µx3, µx4, µx5) using µx1, µx2, µx3, µx4, and µx5 that are average values of the five feature values of the feature vector x. The variance-covariance matrix Σa is a matrix that indicates variation and spread of distribution of the feature vector x that belongs to one class ωa, being represented as a d×d matrix for number of dimensions d that is equal to the number of feature values of the feature vector x.

The control unit 9a calculates a posterior probability P(ω1|x) that the feature vector x that has occurred belongs to a class ω1, posterior probability P(ω2|x) that the feature vector x that has occurred belongs to a class ω2, a posterior probability P(ω3|x) that the feature vector x that has occurred belongs to a class ω3, and a posterior probability P(ω4|x) that the feature vector x that has occurred belongs to a class ω4, according to Formulas (9) to (11) that are based on Bayes' theorem. The control unit 9a then identifies that the feature vector x belongs to the class ωa that gives the largest posterior probability P1(ωa|x) among the four posterior probabilities and classifies the area Hj in which the feature vector x has occurred to the class ωa based on the identification (step S25 in FIG. 21). And the control unit 9a also calculates the value of probability density function p1(x|ωa) that gives the greatest posterior probability P1(ωa|x).

Then, in order to determine whether classification of the area Hj into the class ωa in the preceding processing is correct or not, the control unit 9a performs processing that is based on the distance from an average value, that is, a threshold for the value of probability density function p1(x|ωa) that gives the largest posterior probability P1(ωa|x).

Specifically, the control unit 9a first determines a threshold vector xb1 that contains the sum of average value µx1 of a feature value x1, for example, among the average values of the five feature values of the average vector µa, and the product of standard deviation σx1 of the feature value x1 and multiplication coefficient α as a predetermined constant. This threshold vector xb1 can be represented as Formula (12) below, for example, and the multiplication coefficient α is 1.5 in this embodiment.

$$xb1 = (\mu x1 + \alpha \times \sigma x1, \mu x2, \mu x3, \mu x4, \mu x5) \quad (12)$$

Once the threshold vector xb1 is determined with Formula (12), the control unit 9a substitutes the threshold vector xb1 into x in Formulas (9), (10) and (11) to calculate the value of probability density function p(xb1|ωa) as the threshold value for the class ωa.

If it detects that p1(x|ωa) is larger than p(xb1|ωa) (step S26 in FIG. 21), the control unit 9a determines that classification of area Hj into the class ωa at step S25 in FIG. 21 is correct (step S27 in FIG. 21).

If it detects that p1(x|ωa) is equal to or below p(xb1|ωa) (step S26 in FIG. 21), the control unit 9a determines that classification of area Hj into the class ωa at step S25 in FIG. 21 is not correct and classifies the area Hj into unknown class (step S28 of FIG. 21).

If not all of the (m×n) areas have been classified (step S29 in FIG. 21), the control unit 9a increments the area number j by 1 (step S30 in FIG. 21), and performs the processing shown at steps S25 to S29 in FIG. 21 to the next area.

If the processing described above has not been completed for all the input images Ii (step S31 in FIG. 21), the control unit 9a increments the image number i by 1 (step S32 in FIG.

21) and continues to perform the processing from steps S21 through S31 of FIG. 21 to the next image.

The description above referred to a case that defines a five-dimensional multivariate normal probability density that uses all the five feature values based on the color information and the texture information at a time to determine the feature vector x. However, the image processing method of the embodiment can classify images more accurately by using the feature values for the color information and the texture information separately to determine two kinds of feature vectors xc and xt, and defining two multivariate normal probability densities per class.

Specifically, the control unit $9a$ first calculates a conditional probability density function pc(xc|ωa) for two feature values $\mu gj$ and $\mu bj$ that constitute the color information and a conditional probability density function pt (xt|ωa) for three feature values, CVrj, CVgj, and CVbj, that constitute the texture information. xc is a two-dimensional vector represented as xc=($\mu gj$, $\mu bj$) and xt is a three-dimensional vector represented as xt=(CVrj, CVgj, CVbj).

The control unit $9a$ uses the two conditional probability density functions pc(xc|ωa) and pt(xt|ωa) to calculate posterior probabilities Pc(ωa|xc) and Pt(ωa|xt) according to Formula (10), then calculates final posterior probability P(ωa|x) using Formula (13) below:

$$P(\omega a|x)=Pc(\omega a|xc) \times Pt(\omega a|xt) \quad (13)$$

Threshold values for determining correctness of classification into the class ωa are set asp(xcb|ωa) and p(xtb|ωa), for example, based on average vectors µc and µt of each feature value of the color information and the texture information as well as standard deviations σc1 and σt1. If p1(xc|ωa)>p(xcb|ωa) and p1(xt|ωa)>p(xtb|ωa), the control unit $9a$ determines that the classification is correct so that it classifies one area Hj which has feature vectors xc and xt into one of gastric mucosa, villus, feces, and bubble classes, otherwise, into unknown class.

While the description above assumes that prior probability P(ωa) is equal in all the classes, this is not limitation. The prior probability P(ωa) may be set to a value appropriate for various applications, e.g., it may be set to be high for a villus or feces class based on allocation of time taken for image-capturing various sites by the capsule endoscope 3, or may be set higher for the gastric mucosa and villus classes than the feces and bubble classes that do not require observation on the basis of risk of misclassifying an area captured by the capsule endoscope 3.

As has been thus described, according to the image processing method of the embodiment, it is possible to identify and classify images of gastric mucosa and villus as a biological mucosa surface and images of feces and bubbles as foreign matters or non-biological mucosa for each small area of an image. Thus, the user can easily exclude an image that does not image-capture a biological mucosa surface well like an image many of whose small areas are occupied by foreign matters as an image that does not require observation, which can improve efficiency of observation with the capsule endoscope device 1.

Furthermore, according to the image processing method of the embodiment, when there is an image that is difficult to classify reliably for a reason such as its feature value falling at a distribution boundary or in distribution overlapping range of classes for classification, the image can be classified into unknown class. The control unit $9a$ of the terminal apparatus 7 thus can obtain an image classification result of high reliability by implementing the processing using the image processing method of the embodiment.

Third Embodiment

Figure 22:
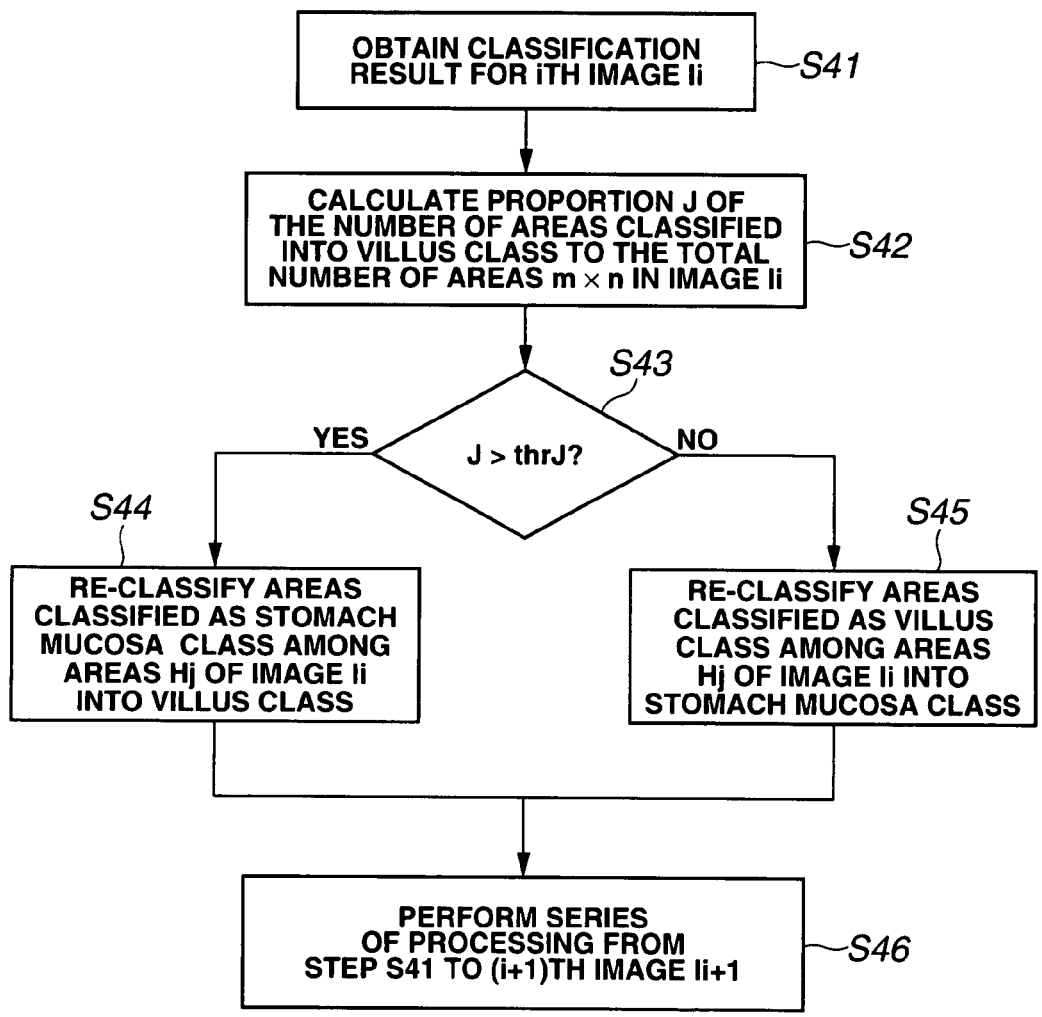
FIG. 22 is a flowchart showing an image processing operation according to a third embodiment.

FIG. 22 is according to a third embodiment of the present invention. Description on components that have similar configurations to the first and second embodiments will be omitted. The same reference numerals are used to indicate components similar to those in the first and second embodiments and description on them is omitted. In addition, a capsule endoscope device 1 of the embodiment has a similar configuration to those of the first and second embodiments and an image processing method of the embodiment is also realized as a program that is executed on a personal computer, for example, as a terminal apparatus 7. And the image processing method of the embodiment is implemented as processing at a control unit $9a$ of a terminal main body 9.

FIG. 22 is a flowchart illustrating image processing operations according to the embodiment.

Before performing the image processing method of the embodiment, the control unit $9a$ first carries out the processing from steps S21 through S30 of FIG. 21, which has been described in the second embodiment, for the inputted ith image Ii to obtain a classification result for the image Ii (step S41 of FIG. 22). In this embodiment, the classification result obtained by the control unit $9a$ through processing shown at step S41 of FIG. 22 is classification of each area of an image into any one of five classes including gastric mucosa, villus, feces, bubble and unknown classes.

Then, the control unit $9a$, which serves as a classification determination value calculation unit, calculates a proportion J of the number of areas classified into the villus class to the total number of areas in the image Ii (m×n) based on the classification result for the image Ii (step S42 of FIG. 22). Specifically, the proportion J is a value calculated by substituting J for p and substituting za, the number of areas classified into the villus class, for z of Formula (4).

The control unit $9a$ then compares the proportion J with a threshold value thrJ. If it detects that the proportion P in the image Ii is larger than the threshold value thrJ (step S43 in FIG. 22), the control unit $9a$, which serves as an area classification unit, re-classifies the areas that have been classified to the gastric class in each area Hj of the image Ii into the villus class (step S44 of FIG. 22). In this embodiment, the threshold value thrJ is 0.5, for example.

If it detects that a proportion p in the image Ii is at or below the threshold value thrJ (step S43 in FIG. 22), the control unit $9a$ which serves as an area division unit re-classifies the areas that have been classified to the villus class in each area Hj of the image Ii into the gastric mucosa class (step S45 in FIG. 22).

When it completes re-classification by way of the processing mentioned above with respect to the image Ii, the control unit $9a$ performs the series of processing from step S41 of FIG. 22 for the (i+1)th image Ii+1 (step S46 in FIG. 22).

As has been described, when the processing that uses the image processing method of the embodiment is carried out by the control unit $9a$, the user can be provided with an effect of improved efficiency of observation that is performed using the capsule endoscope device 1, as in the second embodiment.

In addition, when the image processing method of the embodiment is used, the control unit $9a$ of the terminal apparatus 7 further exclusively substitutes and re-classifies the areas Hj that have been classified into the gastric mucosa and villus classes among images for which it has obtained classification results. Thus, by performing the processing using the image processing method of the embodiment, the control unit $9a$ of the terminal apparatus 7 can eliminate misclassification when it classifies images of gastric mucosa and ones of villi (of small intestine) that cannot be present in a single image together, so that it can obtain classification results of high precision.

Fourth Embodiment

Figure 23:
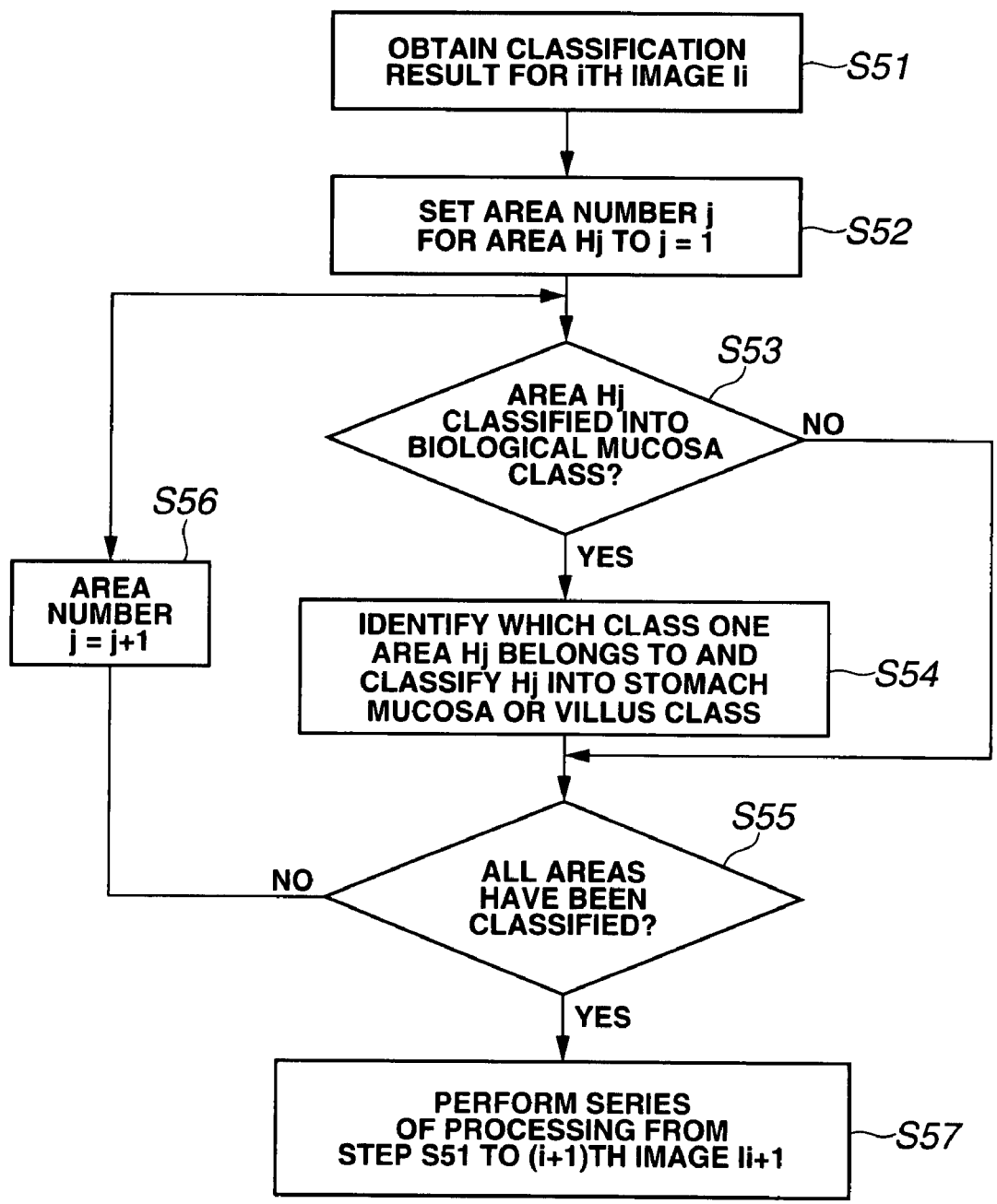
FIG. 23 is a flowchart showing an image processing operation according to a fourth embodiment.

FIG. 23 is according to a fourth embodiment of the invention. Detailed description of components that have similar configurations to the first to third embodiments will be omitted. The same reference numerals are used to indicate components similar to the first to third embodiments and description on them is omitted. Furthermore, a capsule endoscope device 1 of the embodiment has a similar configuration to those of the first to third embodiments, and an image processing method of the embodiment is also realized as a program that is executed on a personal computer, for example, as a terminal apparatus 7. And the image processing method of the embodiment is implemented as processing at a control unit 9a of a terminal main body 9.

FIG. 23 is a flowchart illustrating image processing operations of the embodiment.

Before performing the image processing method of the embodiment, the control unit 9a first inputs an image signal that is based on an image of inside of a body cavity captured by a capsule endoscope 3 and performs the processing from step S21 to step S30, which has been described above in the second embodiment and shown in FIG. 21, to the ith image Ii inputted to obtain classification results for the image Ii (step S51 in FIG. 23). The classification results obtained by the control unit 9a in this embodiment through the processing shown at step S51 of FIG. 23 is classification of each area of the image into any one of four classes including feces, bubble, unknown, and biological mucosa classes.

Thereafter, the control unit 9a sets the area number j for one area Hj to j=1 in order to perform processing to be discussed below (step S52 in FIG. 23). The control unit 9a then determines whether the area Hj has been classified into the biological mucosa class from the classification result for the image Ii (step S53 in FIG. 23).

If it determines that the area Hj has been classified into the biological mucosa class, the control unit 9a calculates posterior probability $P(\omega 1|x)$ that a feature vector x that has occurred in the area Hj belongs to the gastric mucosa class (a=1) and a posterior probability $P(\omega 2|x)$ that the feature vector x that has occurred belongs to the villus class (a=2), using Formulas (9) to (11) into which an average vector $\mu a$ and variance-covariance matrix $\Sigma a$ that are calculated based on feature values contained in images of gastric mucosa and villi that constitute training data are substituted. The control unit 9a then identifies that the feature vector x belongs to a class that gives the largest posterior probability $P2(\omega a|x)$ out of the two posterior probabilities, and classifies the area Hj in which the feature vector x has occurred into either the gastric mucosa or villus class based on the identification (step S54 in FIG. 23).

If not all of (m×n) areas have been classified (step S55 in FIG. 23), the control unit 9a increments the area number j by 1 (step S56 in FIG. 23) and performs the processing shown from steps S53 to S55 in FIG. 23 to the next area.

When it has completed classification by such processing mentioned above for the image Ii, the control unit 9a then performs the series of processing starting from step S51 of FIG. 23 for the (i+1)th image Ii+1 (step S57 in FIG. 23).

As has been described, when the processing using the image processing method of the embodiment is performed by the control unit 9a, the user can be provided with an effect of improved efficiency of observation that uses the capsule endoscope device 1 as in the second embodiment.

In addition, when performing the processing using the image processing method of the embodiment, the control unit 9a of the terminal apparatus 7 further re-classifies the areas Hj that have been classified to the biological mucosa class into the gastric mucosa or villus class among images for which it has obtained classification results. Thus, the control unit 9a of the terminal apparatus 7 can classify images of gastric mucosa and ones of villi (of small intestine) with high precision through processing using the image processing method of the embodiment. Furthermore, the control unit 9a of the terminal apparatus 7 can obtain a classification result that classifies images of gastric mucosa and ones of villi (of small intestine) more accurately by using the image processing method of the present embodiment in combination with the image processing method of the third embodiment.

The image processing method described in the first to fourth embodiments of the invention is not limited to application to images captured by the capsule endoscope 3 of the capsule endoscope device 1, but the method may also be used to images captured by an endoscope device that has an endoscope equipped with imaging devices and an optical systems at the end of its inserting portion, for example.

Fifth Embodiment

Figure 24:
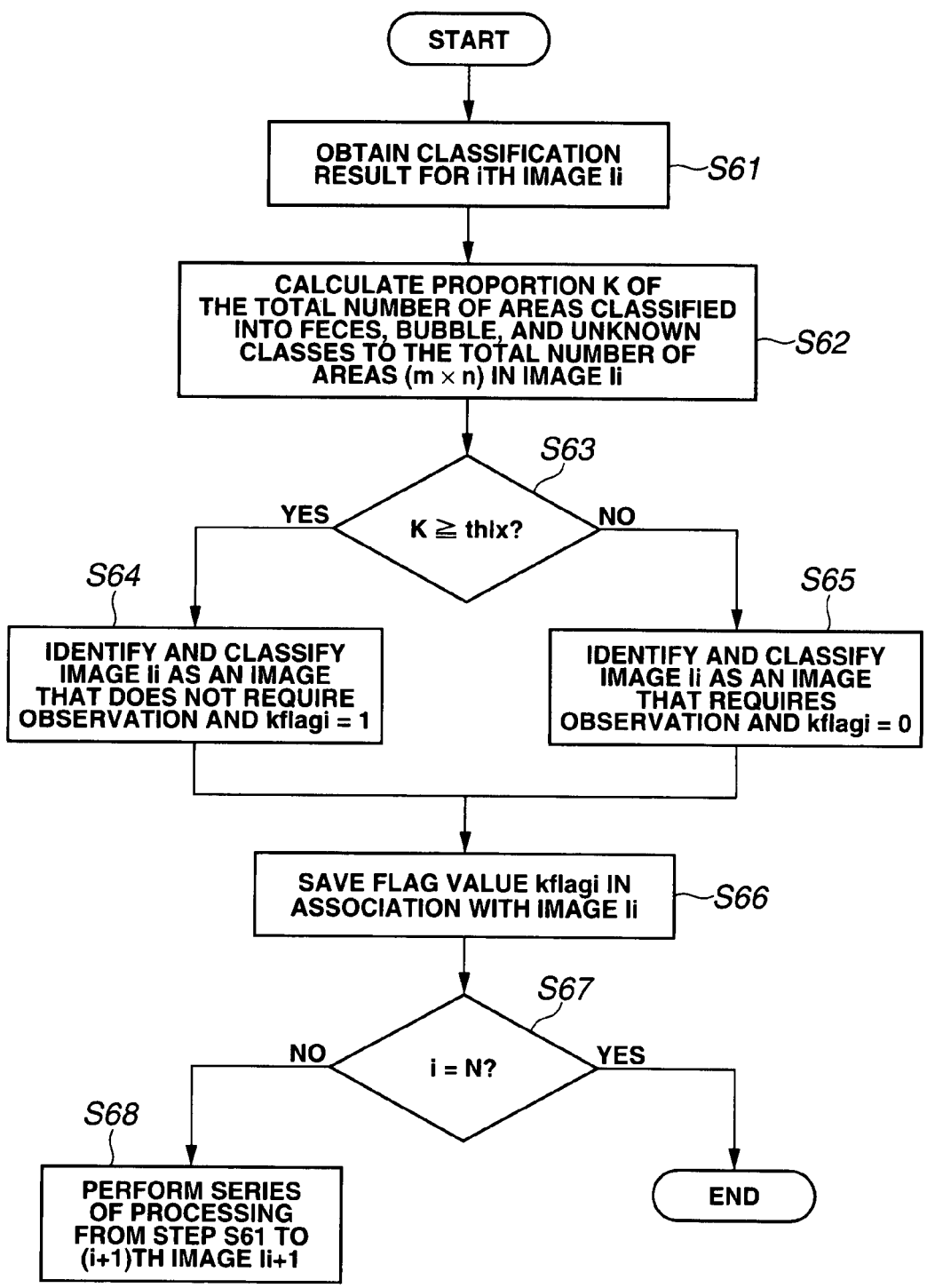
FIG. 24 is a flowchart showing a part of an image processing operation according to a fifth embodiment.
Figure 25:
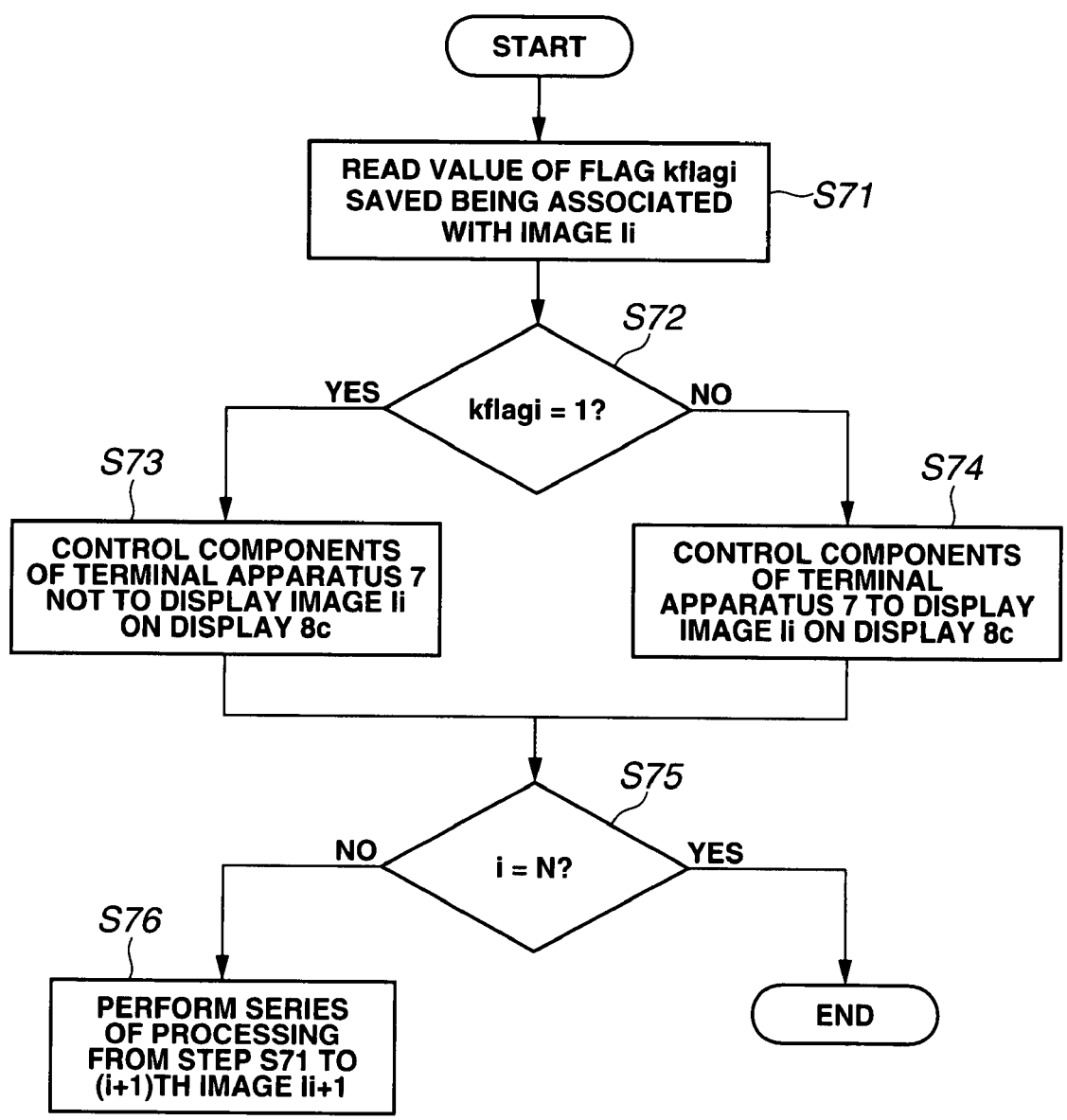
FIG. 25 is a flowchart showing a display controlling operation of an image, which is performed after the processing shown in the flowchart of FIG. 24 is performed, as a part of an image processing operation according to the fifth embodiment.

FIGS. 24 and 25 are according to a fifth embodiment of the invention. Detailed description on components that have similar configurations to the first to fourth embodiments will be omitted. The same reference numerals are used to indicate components that are similar to the first to fourth embodiments and description on them is omitted. In addition, a capsule endoscope device 1 of the embodiment has a similar configuration to those of the first to fourth embodiments, and an image processing of the embodiment is also realized as a program that is executed on a personal computer, for example, as a terminal apparatus 7. And the image processing method of the embodiment is implemented as processing at a control unit 9a of a terminal apparatus 9. Furthermore, in this embodiment, the control unit 9a uses image processing to be discussed below to a series of images that are input to the terminal apparatus 7 in advance.

FIG. 24 is a flowchart illustrating a portion of image processing operations of the embodiment. FIG. 25 is a flowchart showing an operation of controlling image display that follows the processing shown in the flowchart of FIG. 24 as a portion of the image processing operation of the embodiment.

Before performing the image processing method of the embodiment, the control unit 9a first obtains a classification result for the ith input image Ii ($I1 \leq Ii \leq IN$) among a total of N ($1 \leq N$) images (step S61 in FIG. 24). In this embodiment, the control unit 9a can obtain the classification result for the image Ii by using either the processing from steps S1 to S4 shown in FIG. 11 or the processing from steps S21 through S30 shown in FIG. 21. The classification result obtained by the control unit 9a by way of the processing for obtaining a classification result for the image Ii is assumed to be classification of each area of an image into one of five classes including gastric mucosa, villus, feces, bubble and unknown classes. If it detects that one area contains pixels of extreme darkness or halation more than a predetermined threshold during the processing for obtaining the classification result for the image Ii, the control unit 9a may classify the area into one of the feces, bubble, and unknown classes.

The control unit 9a calculates a proportion K of the total number of areas that have been classified into the feces, bubble and unknown classes to the total number of areas (m×n) in the image Ii based on the result of classification obtained at step S61 of FIG. 24 (step S62 in FIG. 24). Then, the control unit 9a compares the proportion K with a threshold value thlx (e.g., 0.7 in this embodiment) to determine whether the image Ii is an image that does not require observation. In this determination, if classification results for the unknown class are not included in classification results obtained by the control unit 9a, the control unit 9a may calculate a proportion K1 of the total number of areas classified into the feces and bubble classes to the total number of areas (m×n) in the image Ii and then compares K1 with the threshold value thlx. Alternatively, when making such determination, the control unit 9a may calculate a proportion K2 of the total number of areas classified into the gastric mucosa and villus classes to the total number of areas (m×n) in the image Ii, and then compare the proportion K2 with a threshold value thly (e.g., 0.3). The threshold values thlx and thly are not limited to fixed values but may be set by the user to desired values by operating the terminal apparatus 7, for example. This allows the user to select the degree to which an image captured biological mucosa surface to observe. The user can accordingly have the control unit 9a implement the image processing method of the embodiment so that the user can employ the method in a way appropriate for his application, e.g., the user can place emphasis on efficiency of observation when conducting a screening test for finding a lesion or view many images more specifically when conducting a thorough examination.

When it subsequently determines that the value of proportion K in the image Ii is equal to or larger than the threshold value thlx (step S63 in FIG. 24), the control unit 9a identifies the image Ii as an image that does not require observation and sets a flag value kflagi as the reference value to 1, for example (step S64 in FIG. 24).

If it determines that the proportion K in the image Ii is smaller than the threshold value thlx (step S63 in FIG. 24), the control unit 9a determines that the image Ii is not an image that does not require observation and sets the flag value kflagi to 0, for example (step S65 in FIG. 24).

The control unit 9a saves the flag value kflagi determined through such processing in association with the image Ii (step S66 in FIG. 24).

Then, the control unit 9a determines whether classification through such processing described above has been done for all images I1 to IN (step S67 in FIG. 24), and if not all the images have been classified, the control unit 9a performs the series of processing starting from step S61 of FIG. 24 for the (i+1)th image Ii+1 (step S68 in FIG. 24). On the other hand, if classification through the processing described above has been done for all the images I1 to IN, the control unit 9a terminates processing for the series of images that have been input to the terminal apparatus 7 in advance.

Assuming that the user observes the series of images I1 to IN that have been classified by way of processing mentioned above starting from the image I1 (i.e., the image with image number i=1) in sequence, the control unit 9a reads the value of flag kflagi that has been saved being associated with the image Ii (step S71 in FIG. 25). The control unit 9a then determines whether the image Ii is an image that does not require observation based on the value of flag kflagi.

If the value of flag kflagi associated with the image Ii is 1 (step S72 in FIG. 25), the control unit 9a gives display control on components of the terminal apparatus 7 not to display the image Ii on a display 8c (step S73 in FIG. 25).

On the other hand, if the value of flag kflagi associated with the image Ii is not 1, that is, if kflagi is 0 (step S72 in FIG. 25), the control unit 9a gives display control on the components of the terminal apparatus 7 to display the image Ii on the display 8c (step S74 in FIG. 25).

The control unit 9a then determines whether the display control described above has been done for all images Ii to IN (step S75 in FIG. 25), and if the control has not been done for all the images, it increments the image number i by 1 and performs the series of processing from step S71 of FIG. 25 to the next image Ii+1 (step S76 in FIG. 25). Further, if the display control has been done for all the images I1 to IN, the control unit 9a determines that the user has finished observation of the images I1 through IN in sequence and completes the display control.

The image processing method described above is not limited to application to a case the user observes the series of images I1 to IN sequentially from the image I1, but may also be used when the user selects and observes a desired image from the images I1 to IN. In the image processing method, the control unit 9a may control the components of the terminal apparatus 7 not to store images that are classified as images that do not require observation, or to delete images stored in a storage unit not shown after they are classified as images not requiring observation.

As has been thus described, according to the image processing method of the embodiment, it is possible to identify and classify images of gastric mucosa and villi as a biological mucosa surface and images of feces and bubbles as foreign matters or a non-biological mucosa surface on a per-image basis and display only images that require observation on the display 8c. The user thus can observe inside of a body cavity excluding images that do not capture a biological mucosa surface well, which can improve efficiency of observation that uses the capsule endoscope device 1.

Sixth Embodiment

FIGS. 26 to 31 are according to a sixth embodiment of the invention. Detailed description on components that have the same configuration as those of the first to fifth embodiments will be omitted. The same reference numerals are used to indicate components that are similar to those of the first to fifth embodiments and description on them is omitted. A capsule endoscope device 1 of the embodiment has a similar configuration as those of the first to fifth embodiments and an image processing method of the embodiment is also realized as a program that is executed on a personal computer, for example, as the terminal apparatus 7. And the image processing method of the embodiment is implemented as processing at a control unit 9a of a terminal main body 9.

Figure 26:
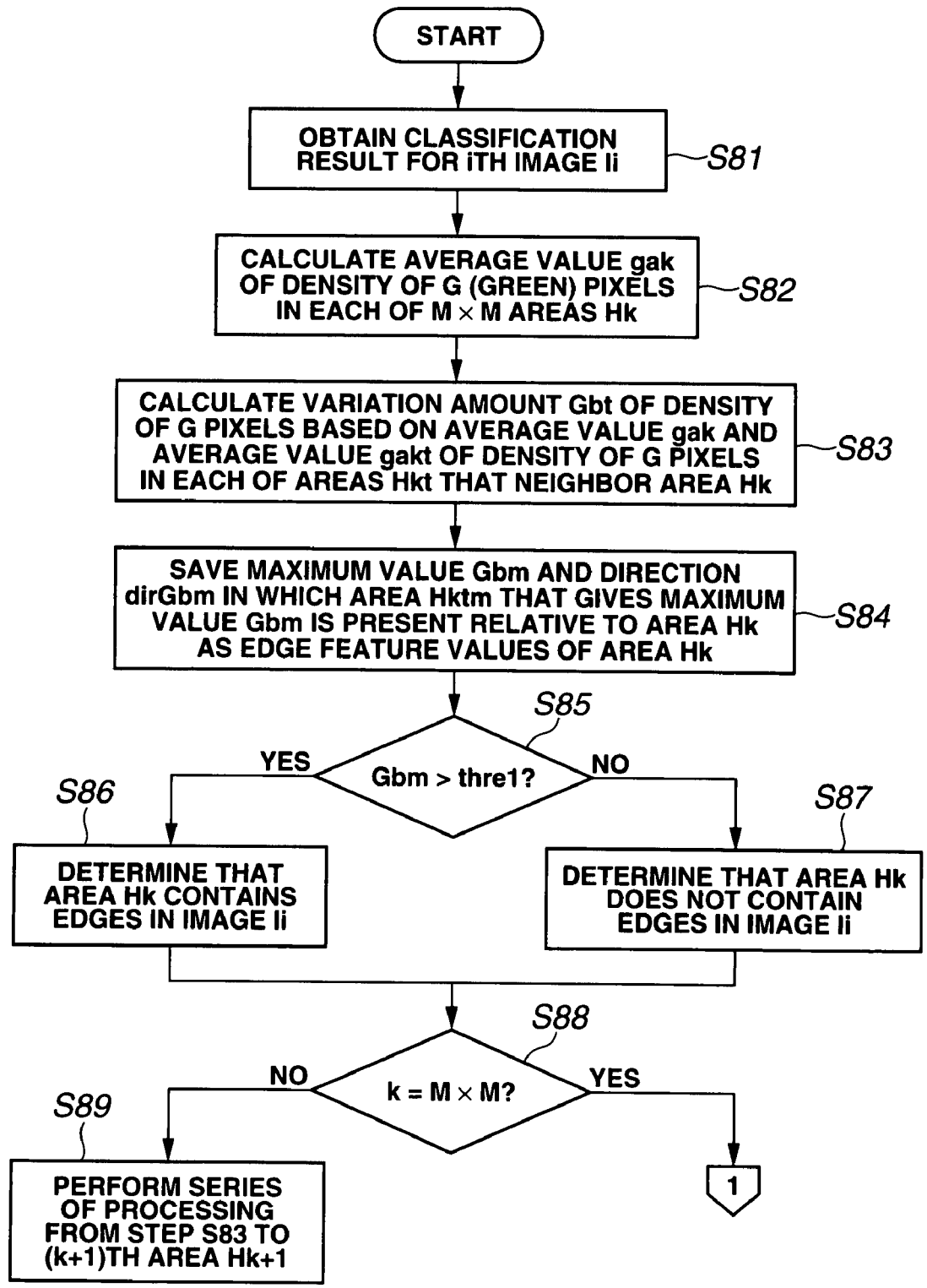
FIG. 26 is a flowchart showing a part of an image processing operation according to a sixth embodiment.
Figure 27:
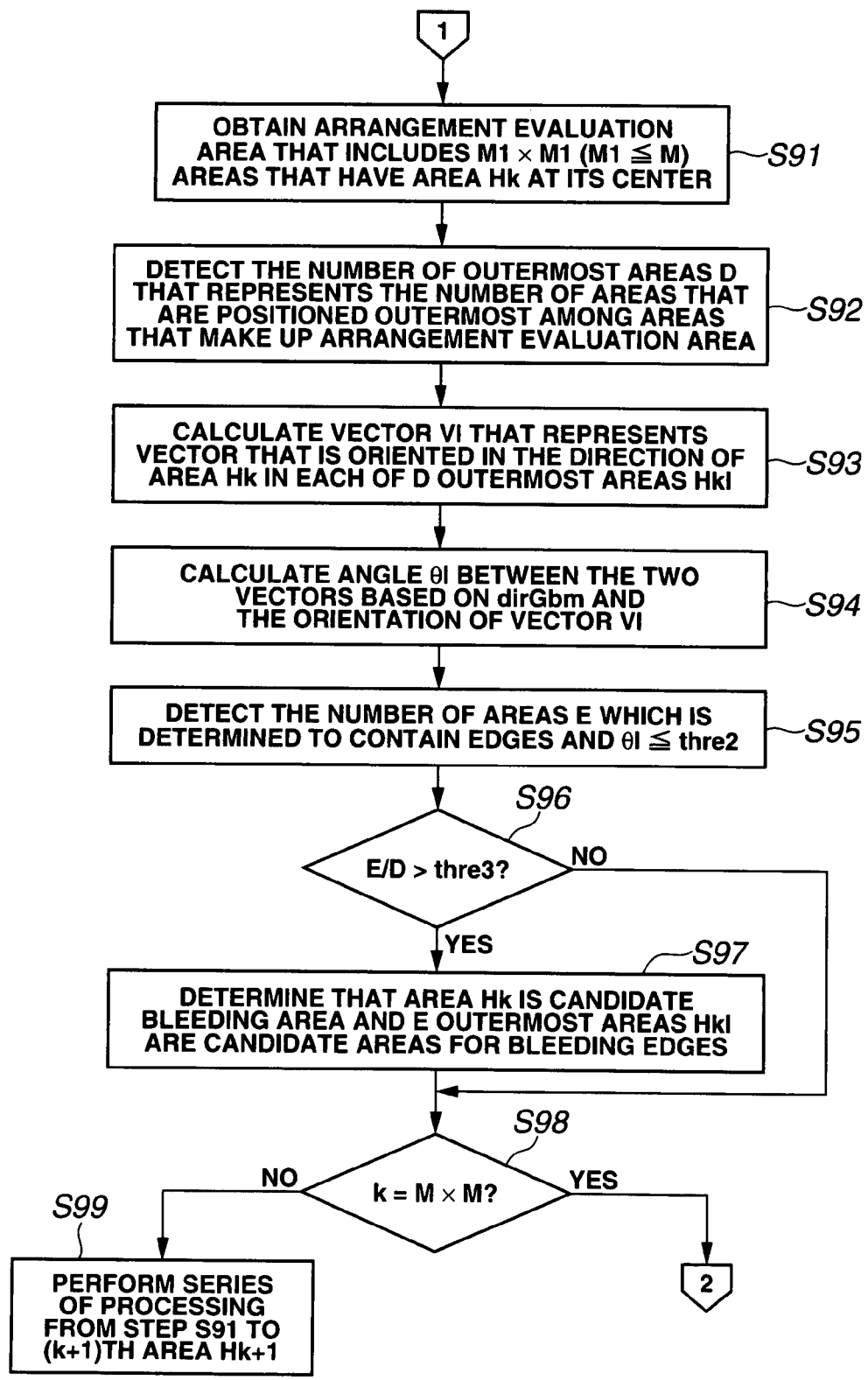
FIG. 27 is a flowchart showing a part of an image processing operation according to the sixth embodiment, which is performed following the processing of FIG. 26.
Figure 28:
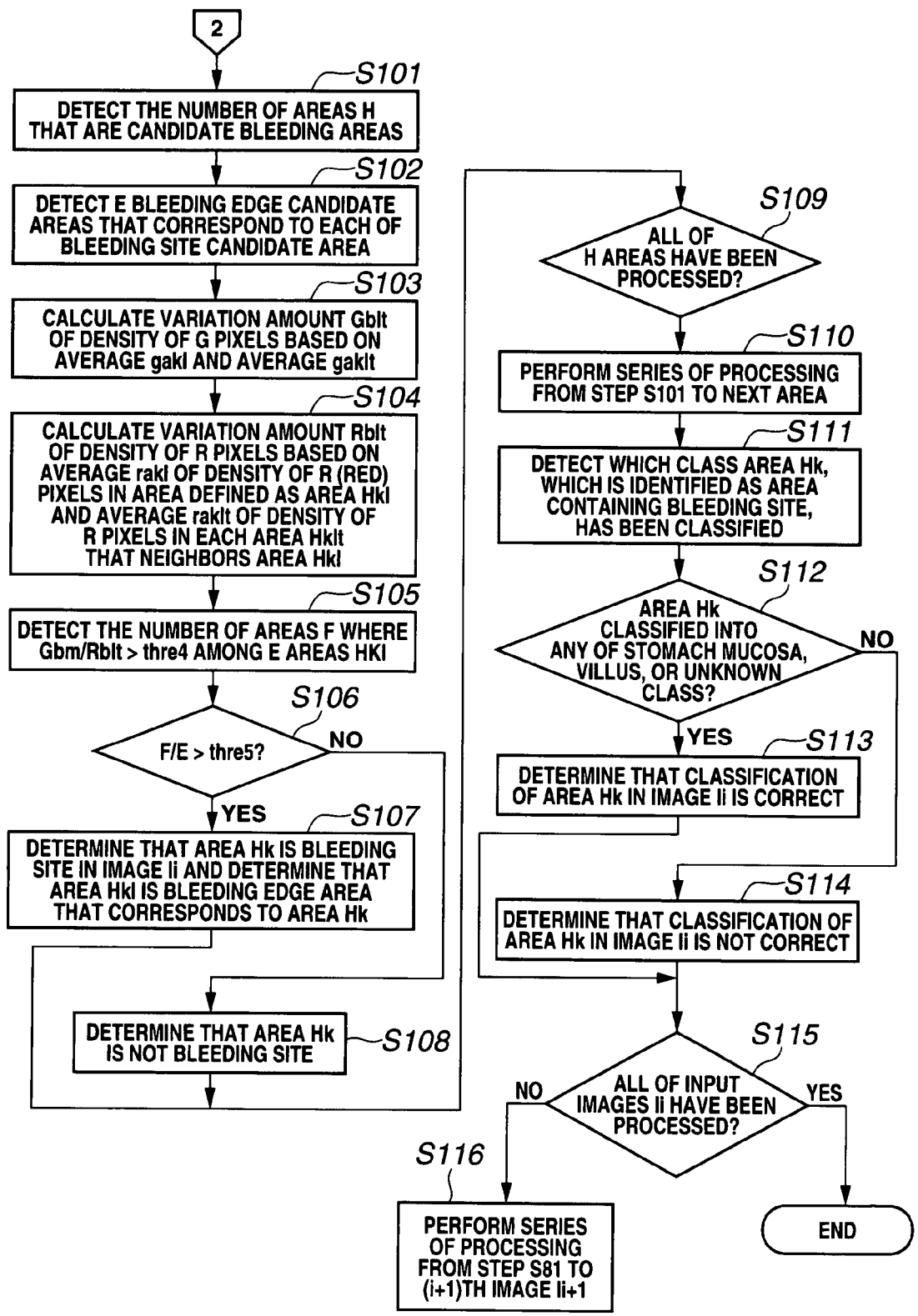
FIG. 28 is a flowchart showing a part of an image processing operation according to the embodiment of FIG. 6, which is performed following the processing of FIG. 27.
Figure 29A:
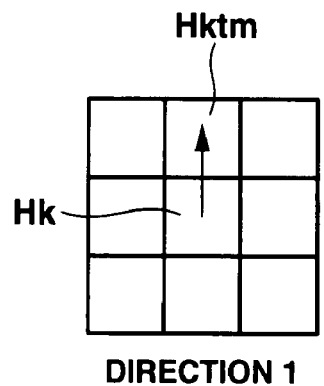
FIG. 29A is a diagram showing one of eight directions, each of which becomes a baseline when an edge feature value (edge characteristic vector) is decided, in the image processing operation according to the sixth embodiment.
Figure 29B:
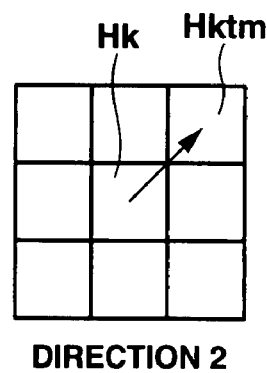
FIG. 29B is a diagram showing a direction different from that in FIG. 29A of eight directions, each of which becomes a baseline when an edge feature value is decided in the image processing operation according to the sixth embodiment.
Figure 29C:
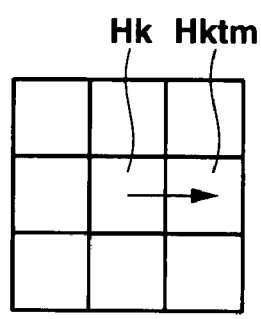
FIG. 29C is a diagram showing a direction different from those in FIG. 29A and FIG. 29B of eight directions, each of which becomes a baseline when an edge feature value is decided in the image processing operation according to the sixth embodiment.
Figure 29D:
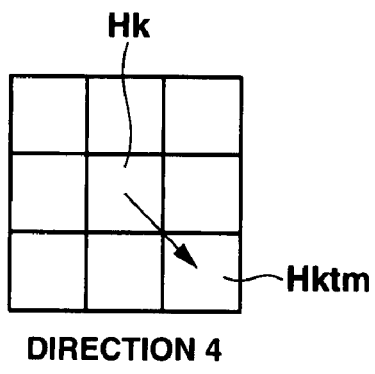
FIG. 29D is a diagram showing a direction different from those in FIG. 29A to FIG. 29C of eight directions, each of which becomes a baseline when an edge feature value is decided in the image processing operation according to the sixth embodiment.
Figure 29E:
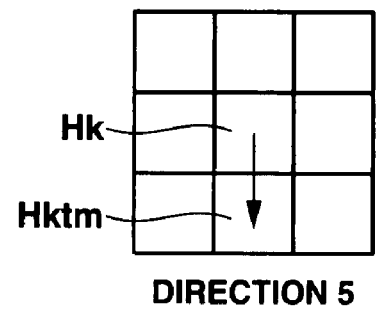
FIG. 29E is a diagram showing a direction different from those in FIG. 29A to FIG. 29D of eight directions, each of which becomes a baseline when an edge feature value is decided in the image processing operation according to the sixth embodiment.
Figure 29F:
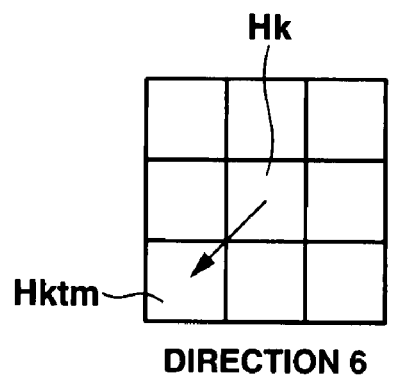
FIG. 29F is a diagram showing a direction different from those in FIG. 29A to FIG. 29E of eight directions, each of which becomes a baseline when an edge feature value is decided in the image processing operation according to the sixth embodiment.
Figure 29G:
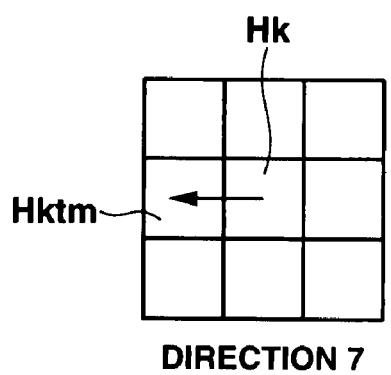
FIG. 29G is a diagram showing a direction different from those in FIG. 29A to FIG. 29F of eight directions, each of which becomes a baseline when an edge feature value is decided in the image processing operation according to the sixth embodiment.
Figure 29H:
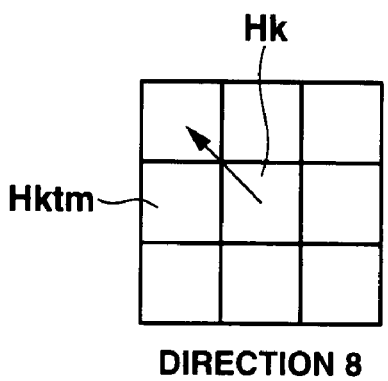
FIG. 29H is a diagram showing a direction different from those in FIG. 29A to FIG. 29G of eight directions, each of which becomes a baseline when an edge feature value is decided in the image processing operation according to the sixth embodiment.
Figure 30:
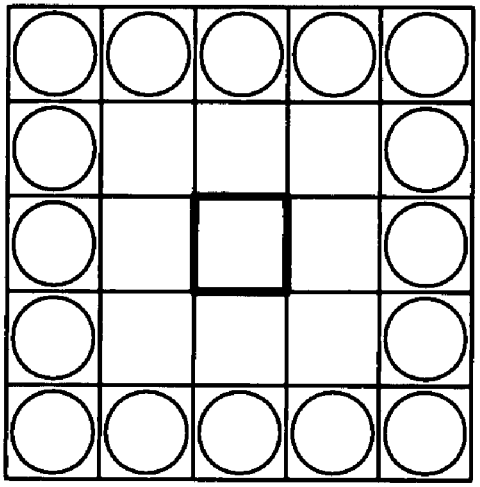
FIG. 30 is a diagram showing physical relationship between a center area and an outermost circumference area, which are set in the image processing operation according to the sixth embodiment.
Figure 31:
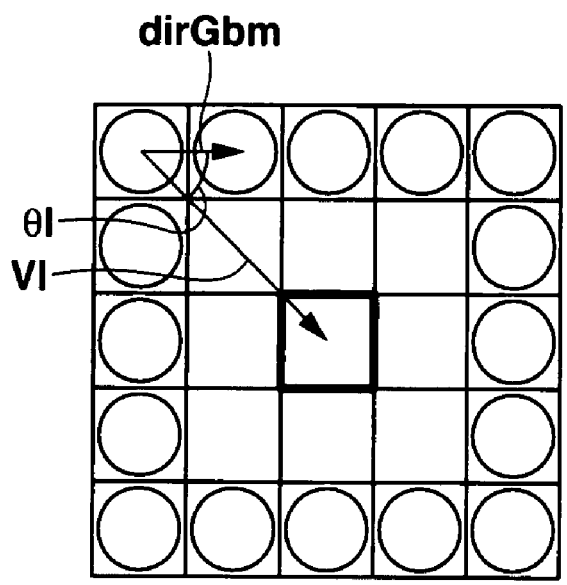
FIG. 31 is a diagram showing an angle formed by a direction of the edge feature vector and a direction of the vector V1, which is set in the image processing operation according to the sixth embodiment.

FIG. 26 is a flowchart illustrating a portion of image processing operations of the embodiment. FIG. 27 is a flowchart illustrating a part of the image processing operations in this embodiment that follows the processing in FIG. 26. FIG. 28 is a flowchart illustrating a part of the image processing operations in this embodiment that follows the processing in FIG. 27. FIG. 29A shows one of eight directions that serve as indices for determining an edge feature value (also denoted as an "edge feature vector") in the image processing operations of the embodiment. FIG. 29B shows one of the eight directions as indices for determining an edge feature value in the image processing operations of the embodiment that is different from the one shown in FIG. 29A. FIG. 29C shows one of the eight directions as indices for determining an edge feature value in the image processing operations of the embodiment that is different from the ones shown in FIGS. 29A and 29B. FIG. 29D shows one of the eight directions as indices for determining an edge feature value in the image processing operations of the embodiment that is different from the ones shown in FIGS. 29A to 29C. FIG. 29E shows one of the eight directions as indices for determining an edge feature value in the image processing operations of the embodiment that is different from the ones shown in FIGS. 29A to 29D. FIG. 29F shows one of the eight directions as indices for determining an edge feature value in the image processing operations of the embodiment that is different from the ones shown in FIGS. 29A to 29E. FIG. 29G shows one of the eight directions as indices for determining an edge feature value in the image processing operations of the embodiment that is different from the ones shown in FIGS. 29A to 29F. FIG. 29H shows one of the eight directions as indices for determining an edge feature value in the image processing operations of the embodiment that is different from the ones shown in FIGS. 29A to 29G. FIG. 30 shows positional relationship between a center area and outermost areas that are defined in the image processing operations of the embodiment. FIG. 31 shows an angle formed between the directions of an edge feature vector and of a vector Vl that are set in the image processing operations of the embodiment.

Before performing the image processing method of the embodiment, the control unit 9a first inputs an image signal that is based on an image of inside of a body cavity captured by a capsule endoscope 3 and obtains a classification result for the ith image Ii inputted (step S81 in FIG. 26). The control unit 9a in this embodiment may obtain the classification result for the image Ii by using either the processing from steps S1 to S4 shown in FIG. 11 or the processing from steps S21 to S30 shown in FIG. 21. The classification result obtained by the control unit 9a through the processing for obtaining a classification result for the image Ii is classification of each area of an image into one of five classes including gastric mucosa, villus, feces, bubble, and unknown classes. In addition, in this embodiment, the control unit 9a divides the input ith image Ii into M×M areas Hk ($1 \leq k \leq M \times M$) in processing at step S81 of FIG. 26. In other words, the control unit 9a obtains a classification result that classifies each of the M×M areas Hk into one of the five classes, i.e., gastric mucosa, villus, feces, bubble, and unknown, as the classification result for the image Ii.

After obtaining the classification result for the image Ii, the control unit 9a calculates an average value gak of density value of G (green) pixels in each of the M×M areas Hk (step S82 in FIG. 26). Then, the control unit 9a calculates a variation amount Gbt of density value of G pixels based on the average value gak of density value of G pixels in area Hk and an average value gakt of density value of G pixels in each area Hkt ($t \leq 8$) that neighbors the area Hk according to Formula (14) below (step S83 in FIG. 26).

$$Gbt = \log(gakt) - \log(gak) \quad (14)$$

The control unit 9a sets the largest value of Gbt in each area Hkt determined with Formula (14) described above as a maximum value Gbm and also sets a direction in which an area Hktm among areas Hkt that gives the maximum value Gbm exists with respect to the area Hk as dirGbm, and then saves the two values as edge feature values for the area Hk (step S84 in FIG. 26). It is assumed that the direction in which the area Hktm giving the maximum value Gbm of variation amount of density value of G pixels exists relative to the area Hk is determined as one of the eight directions 1 through 8 shown in FIGS. 29A to 29H.

Then, the control unit 9a, which serves as an edge detection unit, compares the maximum value Gbm with a threshold value thre1 (step S85 in FIG. 26), and if the maximum value Gbm is larger than the threshold value thre1, it determines that the area Hk contains edges of the image Ii (step S86 in FIG. 26), or if the maximum value Gbm is equal to or smaller than the threshold value thre1, it determines that the area Hk does not contain edges of the image Ii (step S87 in FIG. 26). In this embodiment, the threshold value thre1 may be 0.3, for example. The control unit 9a repeats the processing shown from steps S83 to S87 in FIG. 26 using Formula (14) described above for all of the (M×M) areas Hk while incrementing the area number k by 1, thereby identifying areas that contains edges in the image Ii (steps S88 and S89 in FIG. 26).

The control unit 9a may apply processing such as inverse γ correction or shading correction as preprocessing to the image Ii at a state prior to the processing for detecting edges in the image Ii described above.

After identifying areas that contains edges in the image Ii through the above described processing for all of the (M×M) areas Hk, the control unit 9a obtains a positioning evaluation area that includes M1×M1 ($M1 \leq M$) areas with area Hk as its center area (step S91 in FIG. 27). Subsequently, the control unit 9a detects the number of outermost areas D, which is the number of areas positioned outermost among the areas that constitute the positioning evaluation area (step S92 in FIG. 27). The control unit 9a also calculates the vector Vl that is a vector that has the direction of area Hk, in each of D outermost areas Hkl of the positioning evaluation area (step S93 in FIG. 27). The positional relationship between area Hk and outermost area Hkl may be one shown in FIG. 30, for example.

Based on dirGmb that represents a direction of edge feature vector of each area defined as outermost area Hkl and the direction of vector Vl, the control unit 9a calculates an angle θl formed between the two vectors such as shown in FIG. 31 (step S94 in FIG. 27). The control unit 9a then determines the number of areas E that are determined to be areas containing edges and for which $θl \leq thre2$ among the D outermost areas Hkl in the processing from steps S81 to S89 in FIG. 26 (step S95 in FIG. 27). In this embodiment, the threshold value thre2 may be 45°, for example.

The control unit 9a calculates a value of E/D, and if the value of E/D is larger than a threshold value thre3 (step S96 in FIG. 27), it determines that area Hk is a bleeding site candidate area in which a bleeding site may exist in the image Ii (step S97 in FIG. 27). When the value of E/D is larger than the threshold value thre3 (step S96 in FIG. 27), the control unit 9a determines that the E outermost areas Hkl that have been determined to be areas containing edges in the processing from steps S81 to S89 in FIG. 26 and for which $θl \leq thre2$ is satisfied are bleeding site edge candidate areas which may contain edges of the bleeding sites (step S97 in FIG. 27). In this embodiment, the threshold value thre3 may be 0.7, for example.

The control unit 9a repeats the processing shown at steps S91 to S97 in FIG. 27 that uses Formula (14) described above for all of the (M×M) areas Hk while incrementing the area number k by 1 to thereby identify candidate areas in which bleeding sites exist and candidate areas in which edges of the bleeding sites exist in the image Ii (steps S98 and S99 in FIG. 27).

By performing the above described processing to all of the (M×M) areas Hk, the control unit 9a identifies bleeding site candidate areas and bleeding site edge candidate areas in the image Ii and then detects the number of bleeding site candidate areas H (step S101 in FIG. 28). Thereafter, the control unit 9a detects E bleeding site edge candidate areas that correspond to individual bleeding site candidate areas (step S102 in FIG. 28).

The control unit 9a calculates a variation amount Gblt of density values of G pixels according to Formula (15) below based on an average value gakl of density values of G pixels contained in an area defined as area Hkl as well as an average value gaklt of density values of G pixels in each area Hklt (t≦8) that neighbors the area Hkl in the outermost area Hkl as a bleeding site edge candidate area that corresponds to area Hk as a bleeding site candidate area (step S103 in FIG. 28).

$$Gblt=\log(gaklt)-\log(gakl) \quad (15)$$

The control unit 9a also calculates an average value rakl of density values of R (red) pixels in an area defined as area Hkl and an average value raklt of density values of R pixels in each area Hklt (t≦8) that neighbors the area Hkl, in an outermost area Hkl as a bleeding site edge candidate area that corresponds to area Hk as a bleeding site candidate area. The control unit 9a then calculates a variation amount Rblt of density values of R pixels based on the average values rakl and raklt according to Formula (16) below (step S104 in FIG. 28).

$$Rblt=\log(raklt)-\log(rakl) \quad (16)$$

The control unit 9a calculates a value of Gbm/Rblt as a color edge feature value based on the maximum value Gbm of the area defined as the area Hkl and the variation amount Rblt in the direction of dirGbm. Thereafter, the control unit 9a detects the number of areas F for which Gbm/Rblt>thre4 is satisfied among E areas Hkl (step S105 in FIG. 28). In this embodiment, the threshold value thre4 may be 1.0, for example. In this embodiment, the value used as color edge feature value in processing performed by the control unit 9a is not limited to the value of Gbm/Rblt. The control unit 9a may use a value of Gbm/Bblt as color edge feature value based on a variation amount Bblt of density values of B pixels that is calculated in a similar manner to the variation amount Rblt for the processing described above.

Then, the control unit 9a as a bleeding site determination unit calculates a value of F/E, if the value of F/E is larger than a threshold value thre5 (step S106 in FIG. 28), it determines that the area Hk is a bleeding site in the image Ii and that the area Hkl is a bleeding site edge area that corresponds to the area Hk (step S107 in FIG. 28). On the other hand, if the value of F/E is equal to or below the threshold value thre5 (step S106 in FIG. 28), the control unit 9a determines that the area Hk is not a bleeding site (step S108 in FIG. 28). In this embodiment, the threshold value thre5 may be 0.7, for example. Then, the control unit 9a repeats the processing shown at steps S101 to S108 in FIG. 28 for all the H areas Hk detected as bleeding site candidate areas to identify areas that contains bleeding sites and areas that contains bleeding site edges (steps S109 and S110 in FIG. 28).

After identifying the areas that contains bleeding sites in the image Ii, the control unit 9a makes reference to classification results for the image Ii that have been obtained in the processing at step S81 in FIG. 26 to detect a class into which the area Hk identified as an area containing a bleeding site has been classified (step S111 in FIG. 28). If it detects that the area Hk identified as an area containing a bleeding site has been classified into any of the gastric mucosa class that is included in a class relating to biological mucosa, the villus class included in the class relating to biological mucosa, and the unknown class (step S112 in FIG. 28), the control unit 9a which serves as a classification result determination unit determines that the classification result of the area Hk in the image Ii is correct (step S113 in FIG. 28). Or if it determines that the area Hk identified as an area containing a bleeding site has been classified into the feces class that is included in a class relating to non-biological mucosa or the bubble class included in the class relating to non-biological mucosa (step S112 in FIG. 28), the control unit 9a determines that the classification result of the area Hk in the image Ii is not correct (step S114 in FIG. 28). When it detects that the area Hk identified as an area in which a bleeding site exists has been classified into the unknown class, the control unit 9a may not determine whether the classification result of the area Hk is correct or not, but may identify the area Hk differently, e.g., as "an area in which a lesion site may be captured."

Thereafter, the control unit 9a determines the previous processing has been done for all input images Ii (step S115 in FIG. 28), and if the processing has not been done for all the images, the control unit 9a performs the series of processing from step S71 of FIG. 25 to the next image Ii+1 (step S116 in FIG. 28). Or if the processing has been done for all the input images Ii, the control unit 9a terminates the processing.

As has been thus described, the image processing method of the embodiment can provide an effect of improved efficiency of observation that uses the capsule endoscope device 1 as in the second embodiment.

When the image processing method of the embodiment is employed, 7 the control unit 9a of the terminal apparatus identifies areas Hk in image Ii in which a bleeding site exists and then determines whether the classification results of areas Hk in image Ii it obtained beforehand are correct or not. Thus, by using the image processing method of the embodiment, the control unit 9a of the terminal apparatus 7 can prevent misdetection of a bleeding site such as a bleeding site as a lesion site existing in an area which captures a foreign matter like feces or non-biological mucosa, and it consequently can obtain more reliable results of lesion site detection than with conventional methods.

Seventh Embodiment

Figure 32:
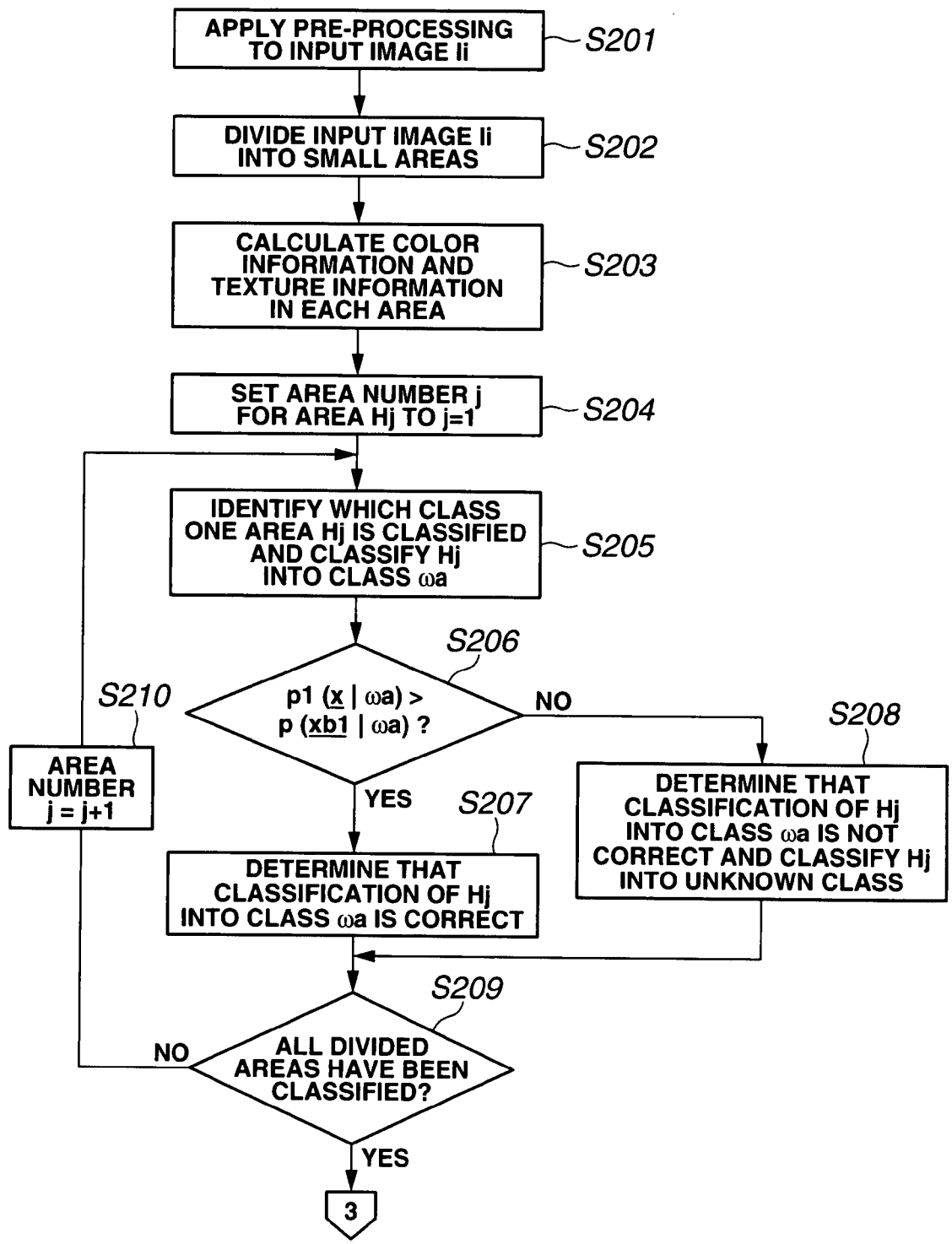
FIG. 32 is a flowchart showing a part of the image processing operation according to a seventh embodiment.
Figure 33:
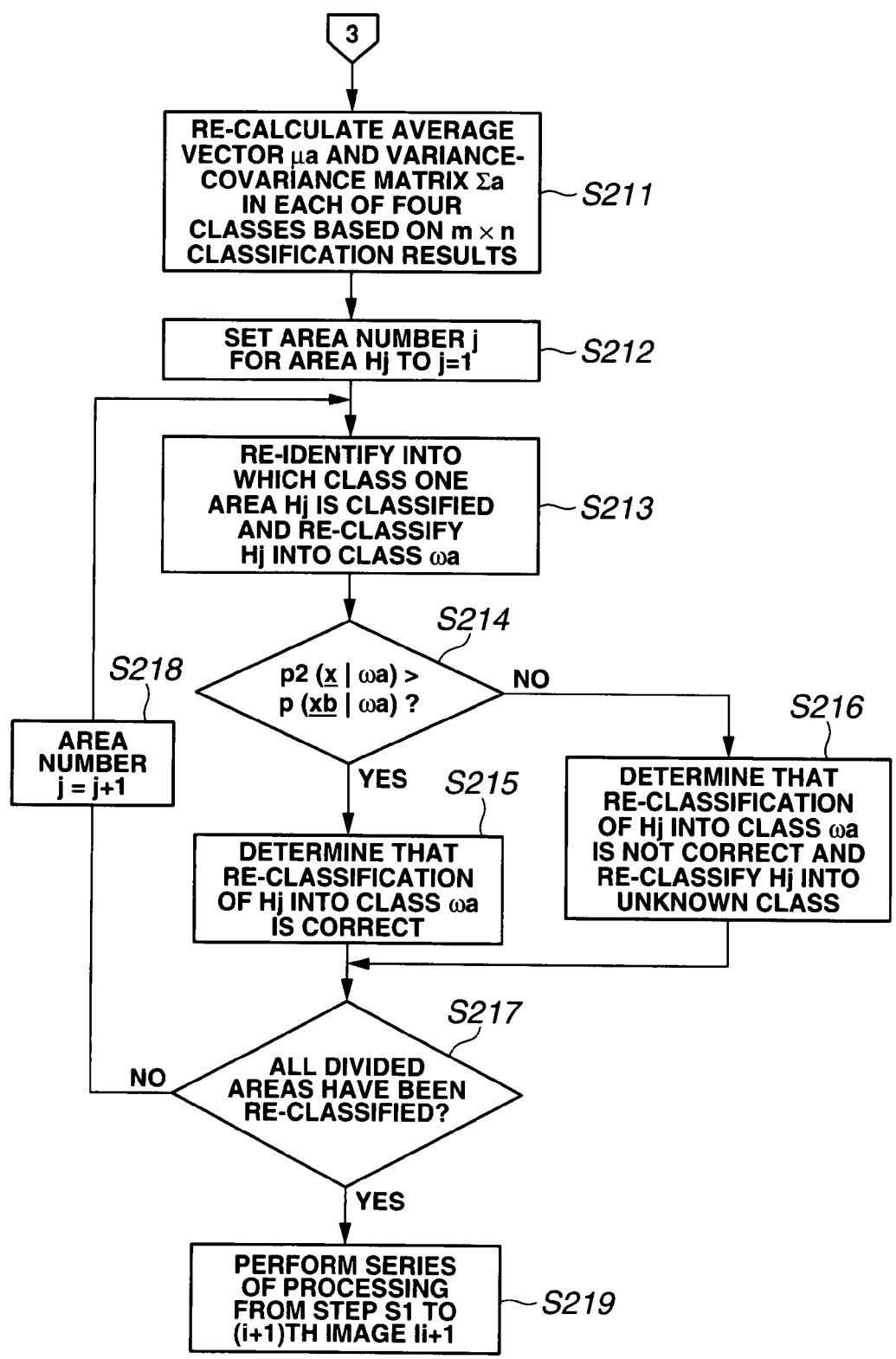
FIG. 33 is a flowchart showing a part of the image processing operation according to the seventh embodiment, which is performed following the processing of FIG. 32.
Figure 34:
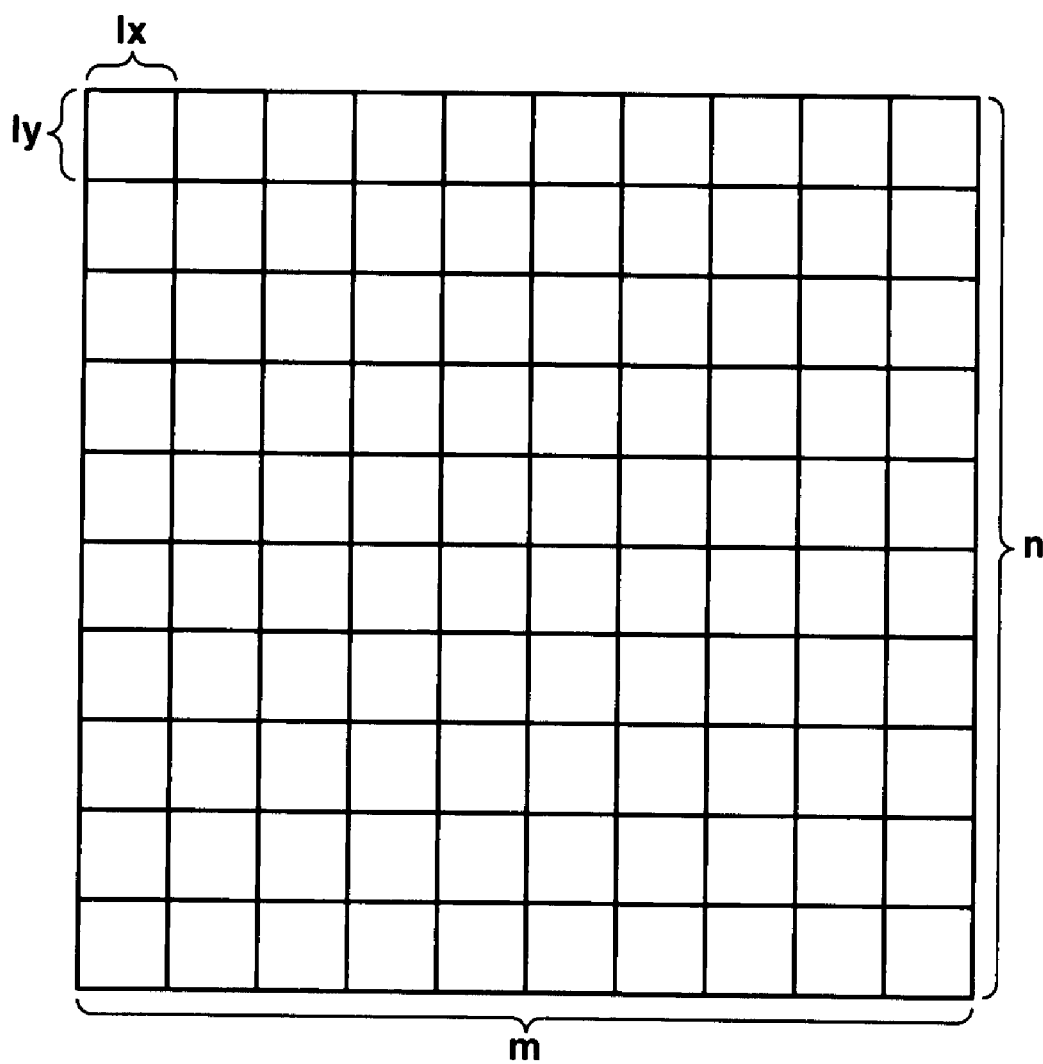
FIG. 34 is a diagram showing an example when the inputted image is divided into (m×n) areas in the image processing operation according to the seventh embodiment.

FIGS. 32 to 34 are according to a seventh embodiment of the present invention. Detailed description of components that have similar configurations to those of first to sixth embodiments is omitted. The same reference numerals are used to indicate components similar to those of first to sixth embodiments and description on them is omitted. A capsule endoscope device 1 of the embodiment has a similar configuration to those of the first to sixth embodiments and the image processing method of the embodiment is also realized as a program that is executed on a personal computer, for example, as a terminal apparatus 7. And an image processing method of the embodiment is implemented as processing at a control unit 9a of a terminal main body 9.

FIG. 32 is a flowchart illustrating a part of image processing operations of the embodiment. FIG. 33 is a flowchart that shows a part of the image processing operations according to the embodiment that follows the processing of FIG. 32. FIG. 34 shows an example of division of an inputted image into (m×n) areas in the image processing operations of the embodiment.

The control unit 9a first inputs an image signal that is based on an image of inside of a body cavity captured by a capsule endoscope 3, applies noise removal by way of media filtering and inverse γ correction, for example, as preprocessing to each of Ri, Gi, and Bi planes that constitute the inputted ith image Ii, and also detects halation pixels and dark pixels through processing based on threshold values in order to exclude them from subsequent processing (step S201 in FIG. 32). The processing based on the threshold values may determine that a pixel is a dark pixel if density values of rik, gik and bik are all no more than 10 and is a halation pixel if all of the density values of rik, gik and bik are no less than 230, for example.

The control unit 9a subsequently divides each of the Ri, Gi, and Bi planes into small areas (step S202 in FIG. 32). In this embodiment, as shown in FIG. 34, the control unit 9a divides each of the Ri, Gi, and Bi planes into rectangle areas each of which contains lx pixels in an x-axis direction×ly pixels in a y-axis direction ($1 \leq lx$, $1 \leq ly$), and there are (m×n) areas (m=ISX/lx and n=ISY/ly). When m or n cannot be an integer, the control unit 9a handles an outermost area that has a size of a decimal fraction as an area that has a decimal fraction number of pixels or excludes it from subsequent processing.

The control unit 9a calculates as feature values color information that reflects difference in color on an image of the object and texture information that reflects difference in structure on the image of the object in the divided areas (step S203 in FIG. 32). In the following description, one of the areas divided by the control unit 9a will be denoted as Hj ($1 \leq j \leq m \times n$).

The color information calculated by the control unit 9a in this embodiment is values represented as two feature values including an average value of gik/rik (hereinafter denoted as "$\mu gj$") and an average value of bik/rik (hereinafter "$\mu bj$") that are based on a ratio of RGB values of each pixel contained in one area Hj. The values $\mu gj$ and $\mu bj$ each assume a value between 0 and 1. The values $\mu gj$ and $\mu bj$ similarly assume small values in an area that exhibits a relatively reddish color such as gastric mucosa, for example. On the other hand, the values $\mu gj$ and $\mu bj$ similarly assume large values in an area that exhibits relatively a whitish color such as the small intestine, for example. The values $\mu gj$ and $\mu bj$ assume values of the relation $\mu gj > \mu bj$ in an area that exhibits a relatively yellow color such as feces, for example.

The texture information calculated by the control unit 9a in this embodiment reflects difference in structure in an image of an object as mentioned above. Structures in an image of an object are represented as minute structures of villi on mucosa surface and an irregular pattern of feces, for example. Specifically, the texture information calculated by the control unit 9a is coefficients of variation for RGB values represented as three feature values, CVrj, CVgj, and CVbj, which are obtained by dividing standard deviations of RGB value σrj, σgj, and σbj for each pixel contained in one area Hj by average values of RGB values mrj, mgj, and mbj for each pixel contained in one area Hj. Formulas for calculating the coefficients of variation CVrj, CVgj, and CVbj are represented as Formulas (17), (18), and (19) below:

$$CVrj = \sigma rj / mrj \qquad (17)$$

$$CVgj = \sigma gj / mgj \qquad (18)$$

$$CVbj = \sigma bj / mbj \qquad (19)$$

The coefficients of variation CVrj, CVgj, and CVbj calculated with Formulas (17), (18) and (19) described above make it possible to numerically represent degree of pixel variation due to a texture structure without being effected by variation in amount of illumination light supplied to the object. In an area that has a relatively flat structure in an image such as gastric mucosa image-captured during normal observation in which enlarged observation is not carried out, the values CVrj, CVgj, and CVbj similarly assume small values because such an area does not have a distinct texture structure. On the other hand, in an area that contains relatively many edges in a structure of an image such as villi of small intestine, for example, the values CVrj, CVgj, and CVbj similarly assume large values.

The control unit 9a then calculates five feature values that include the color and texture information, i.e., $\mu gj$, $\mu bj$, CVrj, CVgj, and CVbj, in each of (m×n) areas Hj based on RGB values of each pixel excluding halation pixels and dark pixels. In this embodiment, if the proportion of the total number of halation pixels and dark pixels exceeds 50%, for example, of (lx×ly) pixels contained in one area Hj, control for excluding the area Hj from subsequent processing may be provided.

Then, the control unit 9a sets the area number j for one area Hj to j=1 in order to perform processing to be discussed below (step S204 in FIG. 32). The control unit 9a uses a statistical classifier based on Bayes' theorem to identify one of the four classes, gastric mucosa, villus, feces, and bubble, to which the area Hj belongs, and classifies the area Hj based on the identification results.

Specifically, denoting a prior probability that one class ωa (a=1, 2, . . . , C; C representing the number of classes) occurs in identification and classification into the four classes as P(ωa); a feature vector determined from the five feature values in one area Hj as x; a probability density function based on the probability of occurrence of the feature vector x from all the classes as p(x); and a conditional probability density (multivariate normal probability density) function based on the occurrence probability of the feature vector x from one class ωa as p(x|ωa), a formula for calculating a posterior probability P(ωa|x) that the feature vector x that has occurred belongs to one class ωa is represented as Formula (20) below:

$$P(\omega a | x) = p(x | \omega a) P(\omega a) / p(x) \qquad (20)$$

The conditional probability density function p(x|ωa) and the probability density function p(x) are represented as Formulas (21) and (22) below:

$$p(x|\omega a) = (1/((2\pi)^{d/2} |\Sigma a|^{1/2})) \exp[(-\tfrac{1}{2})(x-\mu a)^t \Sigma a^{-1}(x-\mu a)] \qquad (21)$$

$$p(x) = \sum_{a=1}^{C} p(x | \omega a) P(\omega a) \qquad (22)$$

In Formulas (21) and (22) described above, d represents the number of dimensions that is equal to the number of feature values of x, and $\mu a$ and $\Sigma a$ represent an average vector of the feature vector x in class ωa and a variance-covariance matrix in one class ωa, respectively. $(x-\mu a)^t$ represents a transposed matrix of $(x-\mu a)$, $|\Sigma a|$ represents a determinant of $\Sigma a$, and $\Sigma a^{-1}$ represents an inverse matrix of $\Sigma a$. For the sake of brevity, it is also assumed that the prior probability P(ωa) is an equal value in all the classes and that the probability density function p(x) is represented by Formula (22) as a function that is common in all the classes.

The average vector $\mu a$ and the variance-covariance matrix $\Sigma a$ that are used as references of classification together with the statistical classifier based on Bayes' theorem are factors that constitute the population parameter in one class ωa, and they are calculated for each class from the feature vector x that is determined for each area of an image based on a plurality of images that constitute training data for the four classes including gastric mucosa, villus, feces, and bubble classes, e.g., images such as ones shown in FIGS. 14, 15, 16 and 17 for describing the first embodiment, at a stage prior to input of the first image I1 to the terminal apparatus 7, and then stored in the terminal apparatus 7 as initial values. At this point, the control unit 9a may estimate the population parameter by adding feature vectors for each class in image Ii to feature vectors in training data for each class.

The average vector μa is a vector that is formed of average values of the five feature values of the feature vector x and that has the same number of dimensions as the feature vector x. That is, denoting the feature vector x as x=(x1, x2, x3, x4, x5), the average vector μa is represented as μa=(μx1, μx2, μx3, μx4, μx5) using μx1, μx2, μx3, μx4, and μx5 that are average values of the five feature values of the feature vector x. The variance-covariance matrix Σa is a matrix that indicates variation and spread of distribution of the feature vector x that belongs to one class ωa, being represented as a d×d matrix for the number of dimensions d that is equal to the number of feature values of the feature vector x.

The control unit 9a calculates a posterior probability P(ω1|x) that the feature vector x that has occurred belongs to a class ω1, a posterior probability P(ω2|x) that the feature vector x that has occurred belongs to a class ω2, a posterior probability P(ω3|x) that the feature vector x that has occurred belongs to a class ω3, and a posterior probability P(ω4|x) that the feature vector x that has occurred belongs to a class ω4, using Formulas (20) to (22) described above that are based on Bayes' theorem. The control unit 9a then identifies that the feature vector x belongs to the class ωa that gives the largest posterior probability P1(ωa|x) among the four posterior probabilities and classifies the area Hj in which the feature vector x has occurred to the class ωa based on the identification results (step S205 in FIG. 32). And the control unit 9a also calculates a value of probability density function p1(x|ωa) that gives the largest posterior probability P1(ωa|x).

Then, in order to determine whether classification of the area Hj into the class ωa in the preceding processing is correct or not, the control unit 9a performs processing that is based on the distance from an average value, that is, a threshold value for the value of probability density function p1(x|ωa) that gives the largest posterior probability P1(ωa|x).

Specifically, the control unit 9a first determines a threshold vector xb1 that contains the sum of an average value μx1 of a feature value x1, for example, among the average values of the five feature values of the average vector μa, and the product of standard deviation σx1 of the feature value x1 and a multiplication coefficient α as a predetermined constant. This threshold vector xb1 can be represented as Formula (23) below, for example, and the multiplication coefficient α is 1.5 in this embodiment.

$$xb1=(\mu x1+\alpha \times \sigma x1, \mu x2, \mu x3, \mu x4, \mu x5) \quad (23)$$

Once the threshold vector xb1 is determined with Formula (23) described above, the control unit 9a substitutes the threshold vector xb1 into x in Formulas (20), (21) and (22) described above to calculate the value of probability density function p (xb1|ωa) as a threshold value for class ωa into which the area Hj has been classified.

If it detects that p1(x|ωa) is larger than p(xb1|ωa) (step S206 in FIG. 32), the control unit 9a determines that the classification of the area Hj into the class ωa at step S205 in FIG. 32 is correct (step S207 in FIG. 32).

If it detects that p1(x|ωa) is equal to or below p(xb1|ωa) (step S206 in FIG. 32), the control unit 9a determines that the classification of the area Hj into the class ωa at step S205 in FIG. 32 is not correct and classifies the area Hj into the unknown class (step S208 of FIG. 32).

If the classification has not been completed for all of the (m×n) areas (step S209 in FIG. 32), the control unit 9a increments the area number j by 1 (step S210 in FIG. 32), and performs the processing shown at steps S205 to S209 in FIG. 32 to the next area. Or if the classification has been completed for all the m×n areas (step S209 in FIG. 32), the control unit 9a re-calculates the average vector μa and the variance-covariance matrix Σa as reference of classification in each of the four classes based on the m×n classification results in the image Ii and the feature values of each of the m×n areas (step S211 in FIG. 33). When re-calculating the average vector μa and the variance-covariance matrix Σa, the control unit 9a may calculate them for only two feature values constituting the color information rather than calculating them for all the five feature values based on the color information and the texture information.

The control unit 9a then sets the area number j for one area Hj to j=1 in order to perform processing to be discussed below (step S212 in FIG. 33).

By using Formulas (20) to (22) described above into which the average vector μa and the variance-covariance matrix Σa determined in the processing shown at step S211 in FIG. 33 are substituted, the control unit 9a re-calculates the posterior probability P(ω1|x) that the feature vector x that has occurred belongs to the class ω1, the posterior probability P(ω2|x) that the feature vector x that has occurred belongs to the class ω2, the posterior probability P(ω3|x) that the feature vector x that has occurred belongs to the class ω3, and the posterior probability P(ω4|x) that the feature vector x that has occurred belongs to the class ω4. The control unit 9a then identifies that the feature vector x belongs to the class ωa that gives the largest posterior probability P2(ωa|x) among the four posterior probabilities and re-classifies the area Hj in which the feature vector x has occurred into the class ωa based on the identification results (step S213 in FIG. 33). And the control unit 9a also calculates a value of probability density function p2(x|ωa) that gives the largest posterior probability P2(ωa|x).

Then, in order to determine whether the re-classification of the area Hj into the class ωa in the preceding processing is correct or not, the control unit 9a performs processing that is based on a threshold value for the value of probability density function p2(x|ωa) that gives the largest posterior probability P2(ωa|x).

That is, as mentioned above, the control unit 9a determines a threshold vector xb2 that contains the sum of the average value μx1 of the feature value x1, for example, among the average values of the five feature values of the average vector μa that have been calculated in the processing shown at step S211 of FIG. 33, and the product of standard deviation σx1 of the feature value x1 and the multiplication coefficient α as a predetermined constant. Once the threshold vector xb2 is determined, the control unit 9a substitutes the threshold vector xb2 into x in Formulas (20), (21) and (22) described above to calculate a value of probability density function p(xb2|ωa) as a threshold value for the class ωa into which the area Hj has been re-classified.

If it detects that p2(x|ωa) is larger than p(xb2|ωa) (step S214 in FIG. 33), the control unit 9a determines that the re-classification of the area Hj into the class ωa is correct (step S215 in FIG. 33).

Or if it detects that p2(x|ωa) is equal to or smaller than p(xb2|ωa) (step S214 in FIG. 33), the control unit 9a determines that the re-classification of the area Hj into the class ωa is not correct and re-classifies the area Hj into the unknown class (step S216 of FIG. 33).

If classification has not been completed for all of the (m×n) areas (step S217 in FIG. 33), the control unit 9a increments the area number j by 1 (step S218 in FIG. 33), and performs the processing shown at steps S213 to S217 in FIG. 33 to the next area. If the classification has been completed for all the m×n areas (step S217 in FIG. 32), the control unit 9a performs the processing starting from step S201 of FIG. 32 to the (i+1)th image Ii+1 (step 219 in FIG. 33).

The average vector μa and the variance-covariance matrix Σa determined in the processing shown at step S211 in FIG. 33 may be used in the processing shown at step S205 of FIG. 32 for the (i+1)th image Ii+1. In this case, image classification can be carried out more accurately by dynamically changing the population parameter that is used for identification and classification of images among images that are temporally successive.

In general, in an image of biological mucosa surface, differences based on the color information are more obvious than differences based on the texture information. For that reason, the processing performed by the control unit 9a at step S211 in FIG. 33 is not limited to re-calculation of the average vector μa and the variance-covariance matrix Σa for both the color information and the texture information, but the control unit 9a may re-calculate μa and the variance-covariance matrix Σa for only one of the color information and the texture information, for example.

The control unit 9a of the terminal apparatus 7 can determine whether the image Ii is an image of biological mucosa surface such as gastric mucosa and villi or not by further performing processing that uses the classification results for the image Ii shown at steps S201 to S218 of FIGS. 32 and 33 as described above.

Specifically, after counting areas classified into each class in the classification results for the image Ii shown at steps S201 to S218 of FIGS. 32 and 33, the control unit 9a calculates the proportion of the number of areas A that have been classified into the gastric mucosa or villus class to the total number of areas (m×n), for example. If A/(m×n) is equal to or larger than a predetermined threshold value (e.g., 0.8), the control unit 9a determines that the image Ii is an image of biological mucosa surface. Consequently, the control unit 9a can extract images that are ensured to be images of biological mucosa surface.

The description above referred to a case that defines a five-dimensional multivariate normal probability density for determining the feature vector x using all the five feature values which are based on the color information and the texture information at a time. However, the image processing method of the embodiment can classify images more accurately by using the feature values for the color information and the texture information separately to determine two kinds of feature vectors xc and xt, and defining two multivariate normal probability densities per class.

Specifically, the control unit 9a first calculates a conditional probability density function pc(xc|ωa) for the two feature values μgj and μbj that constitute the color information and a conditional probability density function pt(xt|ωa) for the three feature values, CVrj, CVgj, and CVbj, that constitute the texture information. xc is a two-dimensional vector represented as xc=(μgj, μbj) and xt is a three-dimensional vector represented as xt=(CVrj, CVgj, CVbj).

The control unit 9a uses these two conditional probability density functions pc(xc|ωa) and pt (xt|ωa) to calculate posterior probabilities Pc(ωa|xc) and Pt(ωa|xt) according to Formula (21), then calculates a final posterior probability P(ωa|x) with Formula (24) below:

$$P(\omega a|x)=Pc(\omega a|xc) \times Pt(\omega a|xt) \quad (24)$$

Threshold values for determining correctness of classification into the class ωa are set asp(xcb|ωa) and p(xtb|ωa), for example, based on average vectors μc and μt and standard deviations σc1 and σt1 for the feature values of the color information and the texture information, respectively. If p1(xc|ωa)>p(xcb|ωa) and p1(xt|ωa)>p(xtb|ωa), the control unit 9a determines that the classification result is correct, so that it classifies the area Hj which has the feature vectors xc and xt into one of the gastric mucosa, villus, feces, and bubble classes, otherwise, into the unknown class.

While the description above assumes that the prior probability P(ωa) is equal in all the classes, this is not limited to this. The prior probability P(ωa) may be set to values appropriate for various applications, e.g., it may be set to be high for the villus or feces class based on allocation of time taken for capturing images of various sites by the capsule endoscope 3, or may be set higher for the gastric mucosa and villus classes than the feces and bubble classes that do not require observation on the basis of risk of misclassifying sites image-captured by the capsule endoscope 3.

The statistical classifier used by the control unit 9a in the image classification is not limited to one based on Bayes' theorem as described above: it may be based on a linear discriminant function, for example.

As has been thus described, according to the embodiment, it is possible to identify and classify images of gastric mucosa and villi as a biological mucosa surface and images of feces and bubbles as foreign matters or a non-biological mucosa surface for each small area. Thus, the user can easily exclude an image that does not capture a biological mucosa surface well, e.g., an image many of whose small areas are occupied by foreign matters, as an image that does not require observation, which can improve efficiency of observation with the capsule endoscope device 1.

Also as described above, according to the embodiment, the population parameter for the statistical classifier can be calculated as a value optimal for images input to the terminal apparatus 7. Thus, even when feature values vary due to difference of color and minute structures of a biological mucosa surface among individuals or variations in features of components that constitute the capsule endoscope 3, the capsules endoscope device 1 used in the embodiment can classify areas of images input to the terminal apparatus 7 highly precisely.

Furthermore, according to the embodiment, it is possible to enhance accuracy of lesion site detection by further performing processing that uses an image processing method for classifying images of normal mucosa and ones of legion sites based on feature values contained in each area that has been classified as an image of biological mucosa surface.

Furthermore, according to the embodiment, it is possible to detect that an image captures villi or feces and classify the image as such. The control unit 9a can therefore identify what organ is image captured in the image by performing the processing that uses a reference of classification, e.g., the image is an image of large intestine if feces has a large proportion in the image, based on the result of classification.

Eighth Embodiment

FIGS. 35 through 40 are according to an eighth embodiment of the invention. Description on components that have similar configurations to those of the first to seventh embodiments will be omitted. The same reference numerals are used to indicate components similar to those in the first to seventh embodiments and description on them is omitted. In addition, a capsule endoscope device 1 of the embodiment has a similar configuration to those of the first to seventh embodiments and an image processing method of the embodiment is also realized as a program that is executed on a personal computer, for example, as a terminal apparatus 7. And the image processing method of the embodiment is implemented as processing at a control unit 9a of a terminal main body 9.

Figure 35:
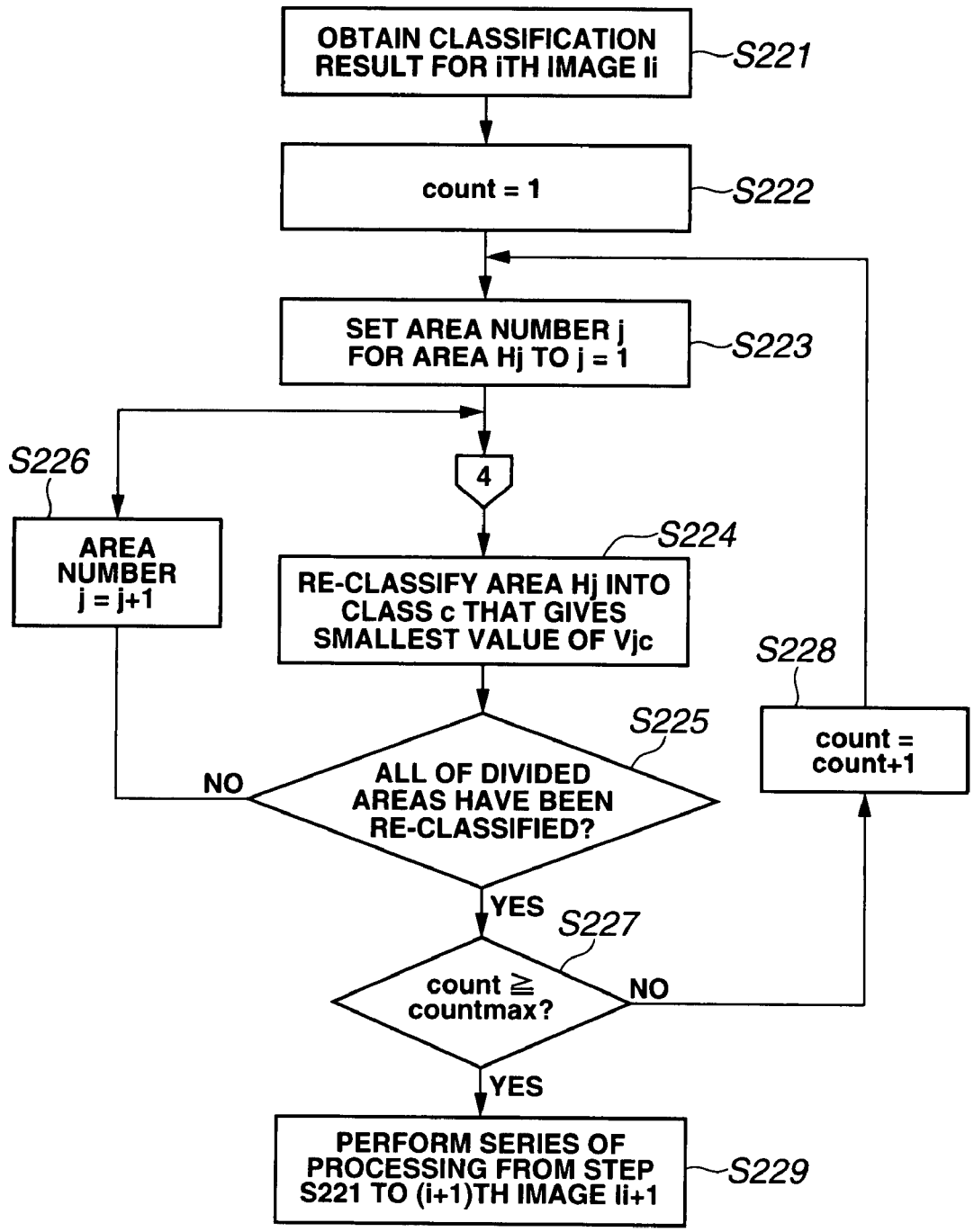
FIG. 35 is a flowchart showing an image processing operation in the image processing apparatus of an eighth embodiment.
Figures 36, 37:
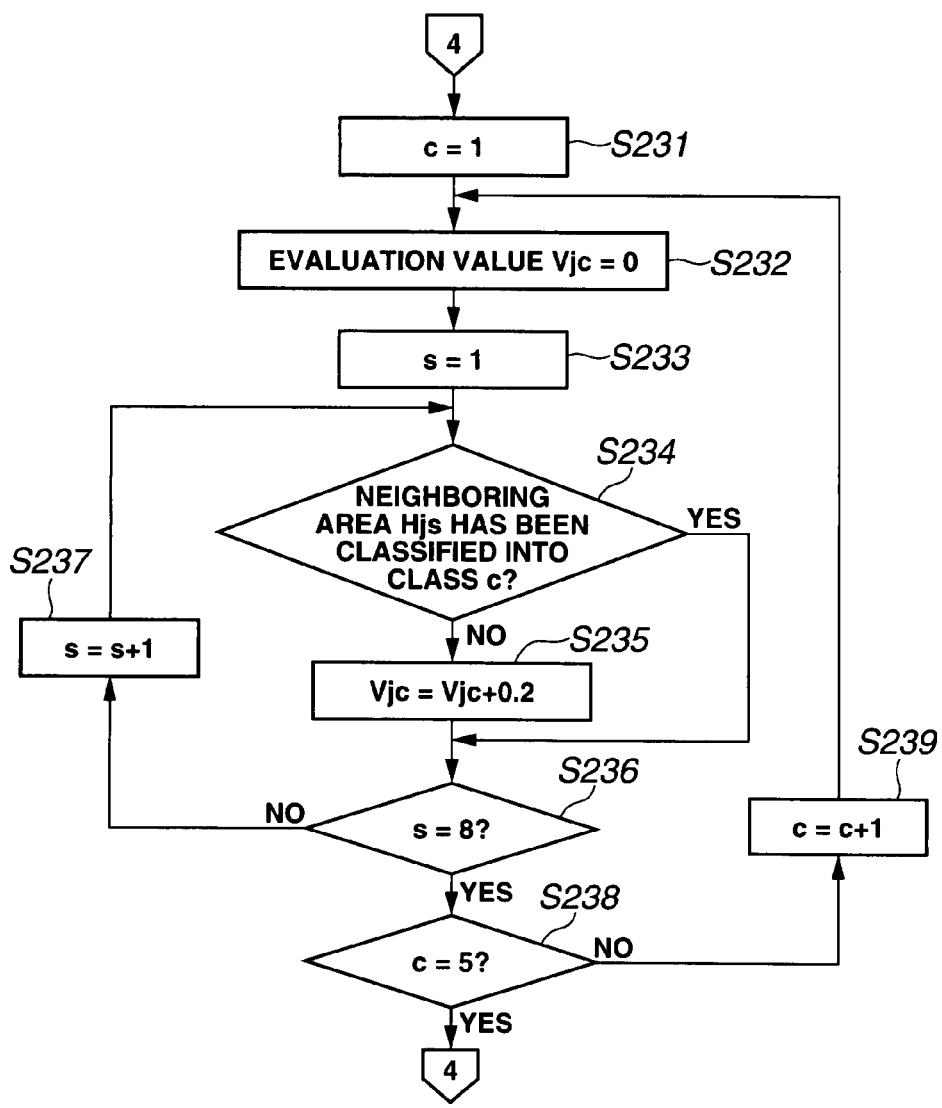
FIG. 36 is a flowchart showing an image processing operation in the image processing apparatus of the eighth embodiment.
FIG. 37 is a diagram showing an example when a proximity area in one area is decided in the image processing operation of the eighth embodiment.
Figure 38:
FIG. 38 is schematic diagram showing an example of an image of a view inside a body cavity which is captured by the capsule endoscope, which is used in the image processing operation of the eighth embodiment.
Figure 39:
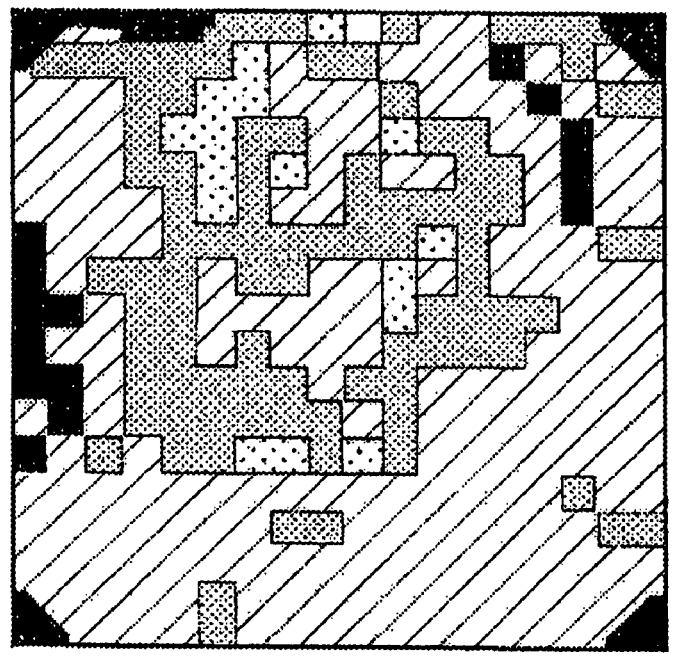
FIG. 39 is a diagram showing an example of the classification result of the image shown FIG. 38.
Figure 40:
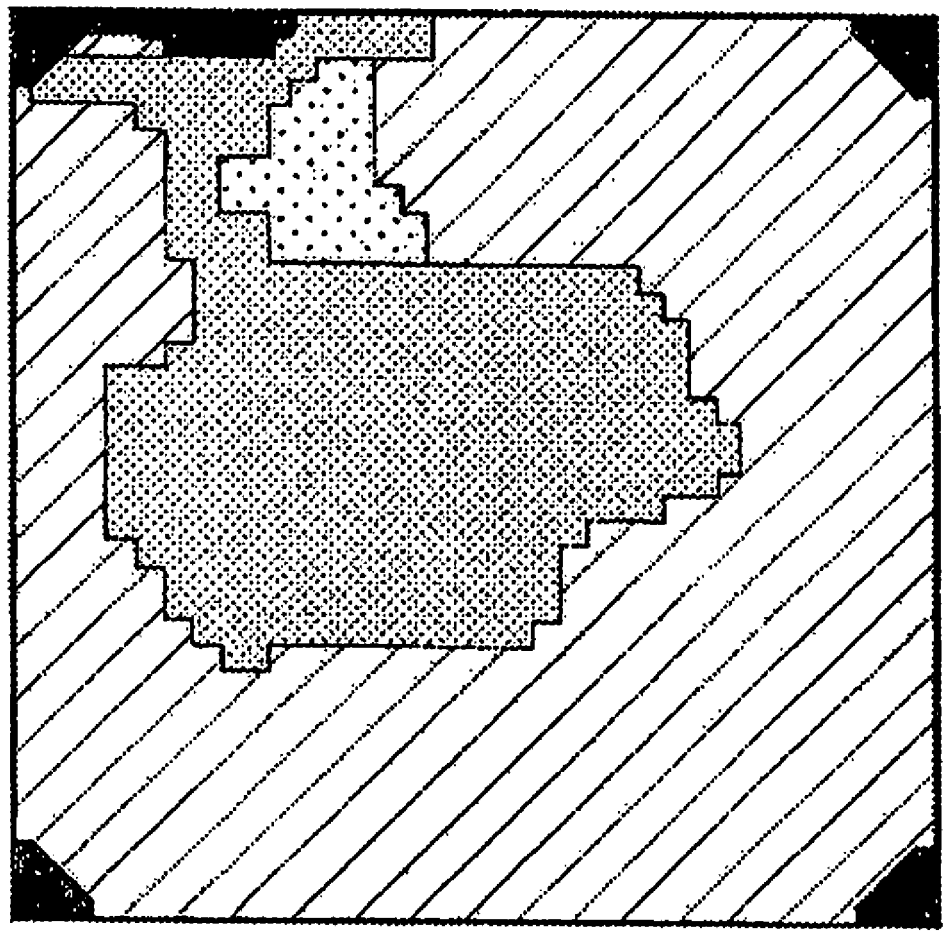
FIG. 40 is a diagram showing re-classification result after the image processing operation of the eighth embodiment is performed based on the classification result shown in FIG. 39.

FIG. 35 is a flowchart illustrating image processing operations on an image processing apparatus of the embodiment. FIG. 36 is a flowchart showing image processing operations on the image processing apparatus of the embodiment. FIG. 37 shows an example of determination of neighboring areas of one area in the image processing operations of the embodiment. FIG. 38 schematically illustrates an example of an image of inside of a body cavity captured by a capsule endoscope that is used in the image processing operations of the embodiment. FIG. 39 shows an example of a classification result for the image shown in FIG. 38. FIG. 40 shows a re-classification result after the image processing operations of the embodiment are carried out based on the classification result of FIG. 39.

Before performing the image processing operations of the embodiment, the control unit 9a first inputs an image signal that is based on an image of inside of a body cavity captured by the capsule endoscope 3 and performs the processing from step S201 to step S218, which has been described above in the seventh embodiment and shown in FIGS. 32 and 33, to the ith input image Ii to obtain classification results for the image Ii (step S221 in FIG. 35).

Then, the control unit 9a sets a value of count (1≦count) that indicates the number of area merge iterations to count=1 (step S222 in FIG. 35). A value of countmax that indicates the maximum number of area merge iterations is set by the user. The control unit 9a then performs area merge, which will be discussed in detail below, a number of times indicated by the value of countmax set by the user. The embodiment assumes that the value of countmax is 5 for the following description.

The control unit 9a sets the area number j for one area Hj to j=1 (step S223 in FIG. 35) and then calculates an evaluation value for evaluating classification of the area Hj into a class c (c=1, 2, 3, 4, or 5). The five classes 1 to 5 correspond to any one of gastric mucosa, villus, feces, bubble, and unknown classes one to one.

Specifically, the control unit 9a first sets the class c as a candidate for classifying the area Hj to c=1 (step S231 in FIG. 36). Then, the control unit 9a sets an evaluation value Vjc to Vjc=0 that is derived from a cost function based on classification results for neighboring areas of the area Hj, which will be described below (step S232 in FIG. 36). The control unit 9a sets an area s (s=1, 2, 3, 4, 5, 6, 7 or 8) that represents eight neighboring areas of the area Hj such as shown in FIG. 37 to s=1 (step S233 in FIG. 36). The eight neighboring areas of the area Hj that are represented as eight areas 1 to 8 correspond to any one of rectangle areas 1 to 8 shown in FIG. 37 one to one. Each of the neighboring areas of the area Hj will be denoted as Hjs. When eight neighboring areas cannot be set for one area Hj because the area Hj is on the edge of an image or some areas have been excluded from processing as they are dark pixels or halation pixels, the control unit 9a performs processing discussed below to only areas that can be set as neighboring areas of the area Hj.

The control unit 9a determines from the classification results for the image Ii whether the neighboring area Hjs has been classified into the class c (step S234 in FIG. 36). If it detects that the neighboring area Hjs has not been classified into the class c, the control unit 9a, which serves as an evaluation value calculation unit, uses a cost function represented as Formula (25) below to add 0.2 to the evaluation value Vjc (step S235 in FIG. 36).

$$Vjc = Vjc + 0.2 \qquad (25)$$

Subsequently, the control unit 9a repeats the processing shown at steps S234 and S235 of FIG. 36 using Formula (25) described above for all neighboring the areas Hjs of area Hj while incrementing the area number s by 1 so as to calculate an evaluation value for the class c (steps S236 and S237 in FIG. 36).

After it determines the evaluation value for the class c (step S236 in FIG. 36), the control unit 9a repeats the series of processing shown at steps S232 to S237 in FIG. 36 while incrementing the class number c by 1 to calculate evaluation values for all the classes 1 to 5 (steps S238 and S239 in FIG. 36).

The control unit 9a, which serves as an area classification unit, compares values of Vjc, that is, Vj1, Vj2, Vj3, Vj4, and Vj5, with each other, and re-classifies the area Hj into the class c that gives the smallest value of Vjc (step S224 in FIG. 35). When there are a plurality of classes c that give the smallest Vjc, the control unit 9a may select a class that has the smallest c.

If the classification has not completed for all the m×n areas at a predetermined value of count (step S225 in FIG. 35), the control unit 9a increments the area number j by 1 (step S226 in FIG. 35) and repeats the series of processing including the processing shown at steps S223 and S224 of FIG. 35 and steps S231 to S239 of FIG. 36 to the next area.

If the classification has been completed for all the m×n areas and the value of count is smaller than the value of countmax (step S227 in FIG. 35), the control unit 9a increments the value of count by 1 (step S228 in FIG. 35) and then repeats the series of the processing including processing shown at steps S222 to S227 of FIG. 35 and steps S231 to S239 of FIG. 36 to the Image Ii. Or if the classification has been completed for all the m×n areas and the value of count is equal to or larger than the value of countmax (step S227 in FIG. 35), the control unit 9a then performs the series of processing starting from step S221 of FIG. 35 to the (i+1)th image Ii+1 (step S229 in FIG. 35).

An example of processing done by the control unit 9a of the terminal apparatus 7 using the image processing operations of the embodiment is shown in FIGS. 38, 39 and 40. FIG. 38 schematically illustrates an image that represents the image Ii in the image processing operations of the embodiment described above. When the image Ii such as the one shown in Fig. 38 is input to the terminal apparatus 7, the control unit 9a of the terminal apparatus 7 obtains a classification result shown in FIG. 39 through the processing shown at step S221 in FIG. 35. Then, by further repeating the area merge shown at step S222 and subsequent steps of FIG. 35 a number of times that is set as the value of countmax (5 in this embodiment) based on the classification result shown in FIG. 39, the control unit 9a obtains a re-classification result shown in FIG. 40.

As has been thus described, when the processing using the image processing method of the embodiment is implemented by the control unit 9a, the user can be provided with an effect of improved efficiency of observation that uses the capsule endoscope device 1 as in the seventh embodiment. In addition, when the image processing method of the embodiment is employed, the control unit 9a of the terminal apparatus 7 can classify areas of an image further accurately while reducing occurrence of misclassified areas because it re-classifies a certain area of an image input to the terminal apparatus 7 based on classification results for areas that neighbor that area.

Ninth Embodiment

FIGS. 41 through 47 are according to a ninth embodiment of the invention. Description on components that have similar configurations to those of the first to eighth embodiments will be omitted. The same reference numerals are used to indicate components similar to those in the first to eighth embodiments and description on them is omitted. In addition, a capsule endoscope device 1 of the embodiment has a similar configuration to those of the first to eighth embodiments and the image processing method of the embodiment is also realized as a program that is executed on a personal computer, for example, as a terminal apparatus 7. And the image processing method of the embodiment is implemented as processing at a control unit 9a of a terminal main body 9.

Figure 41:
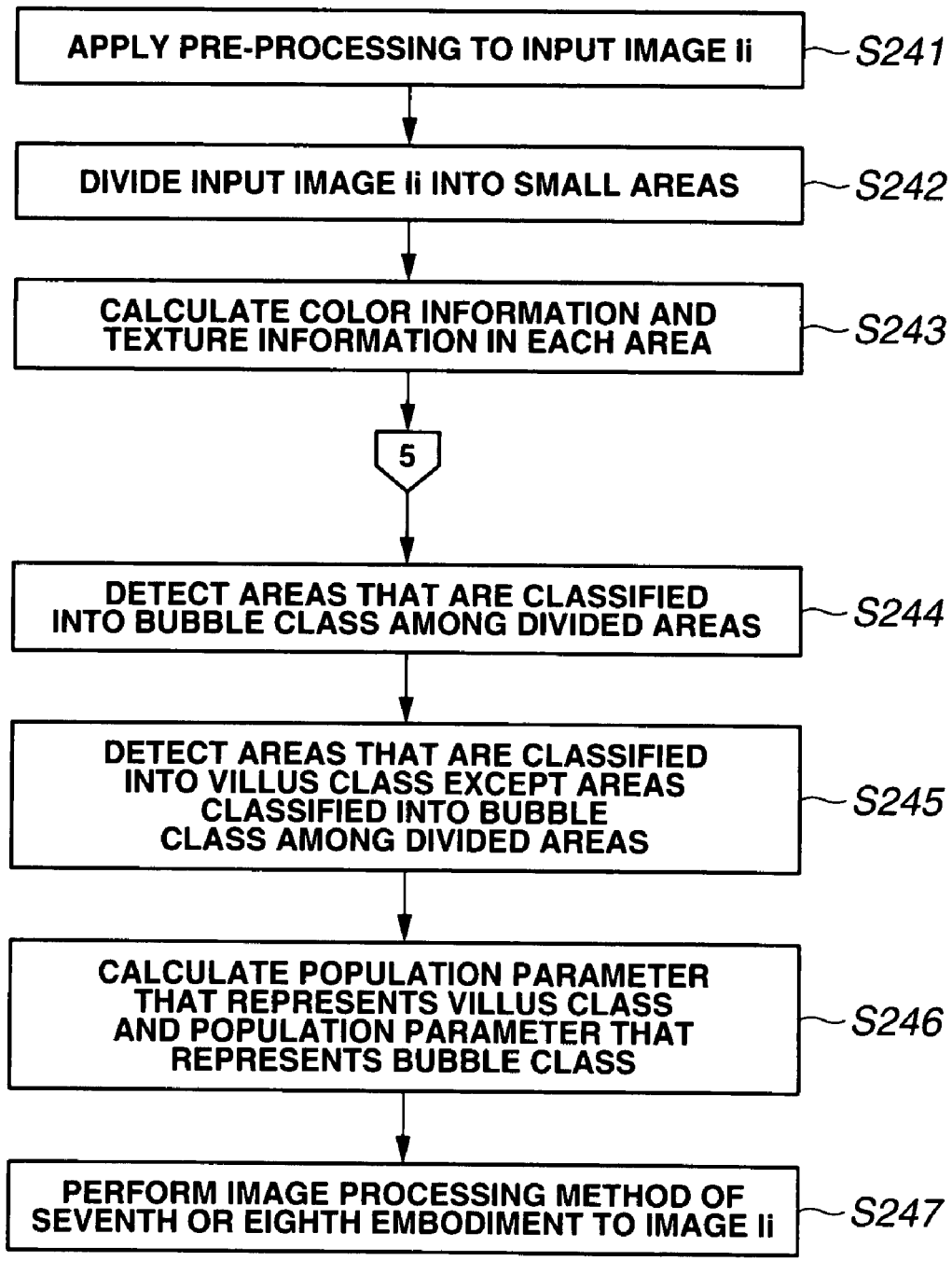
FIG. 41 is a flowchart showing an image processing operation of a ninth embodiment.
Figure 42:
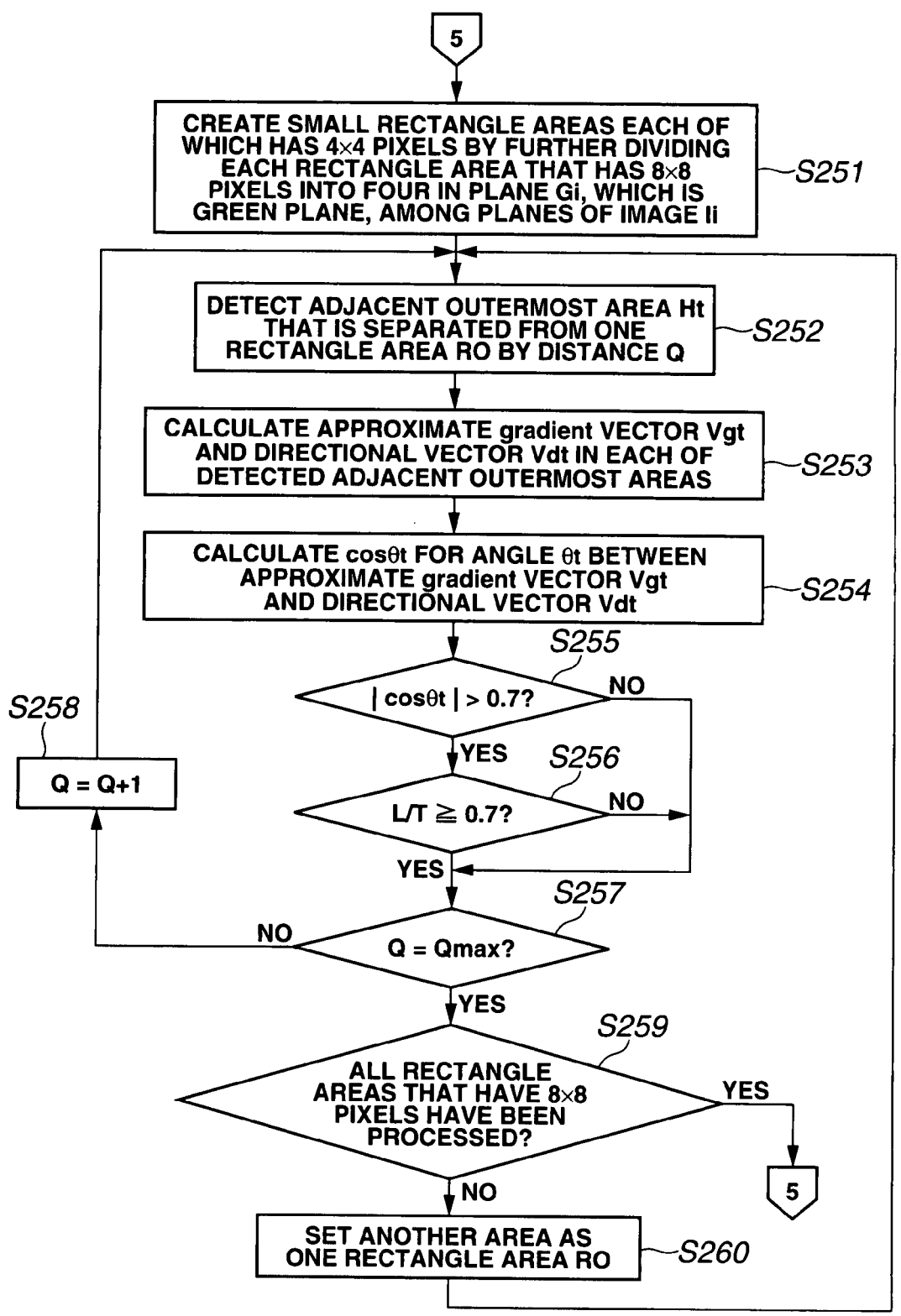
FIG. 42 is a flowchart showing an image processing operation of the ninth embodiment.
Figures 43, 44:
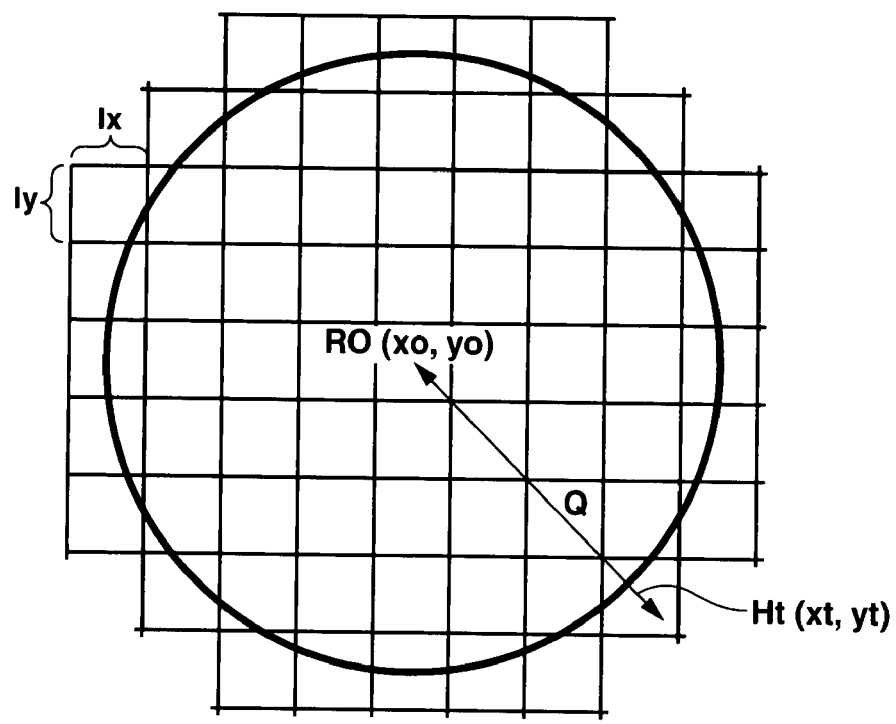
FIG. 43 is a diagram showing an example of an arrangement of numbers virtually given to each of small rectangular areas having the number of 4×4 pixels in the image processing operation in the ninth embodiment.
FIG. 44 is a diagram showing positional relationship between a rectangular area RO and a close circumference area Ht in the image processing operation in the ninth embodiment.
Figure 45:
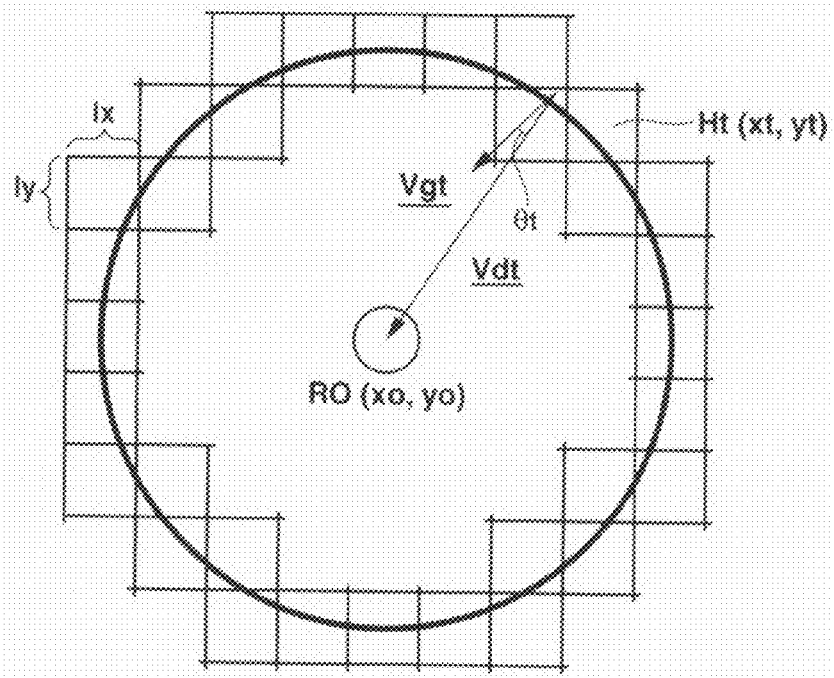
FIG. 45 is a diagram showing an example of the angle θt formed by an approximate gradient vector Vgt and a direction vector Vdt in the image processing operation in the ninth embodiment.
Figure 46:
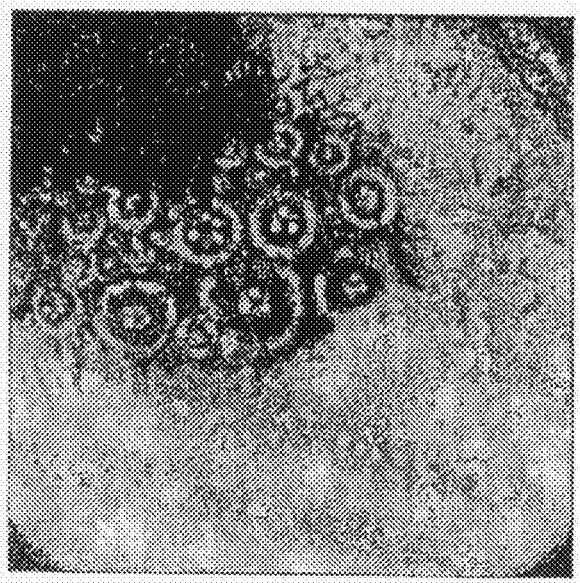
FIG. 46 is a schematic diagram showing an example of an image of a view inside a body cavity captured by the capsule endoscope used in the ninth embodiment.
Figure 47:
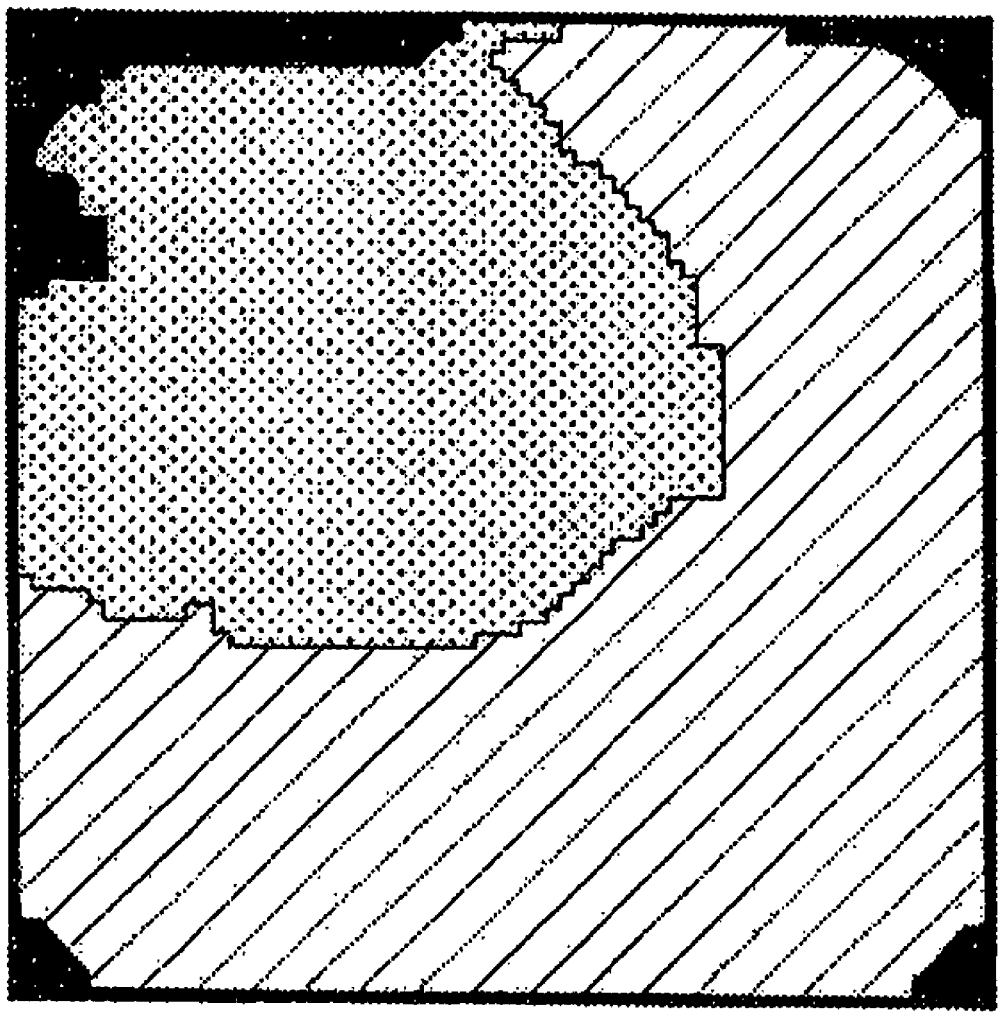
FIG. 47 is a diagram sowing an example of a classification result of the image shown in FIG. 46.

FIG. 41 is a flowchart illustrating image processing operations in the embodiment. FIG. 42 is a flowchart illustrating the image processing operations in the embodiment. FIG. 43 shows an example of an arrangement of numbers that are virtually assigned to small rectangle areas each of which contains 4×4 pixels in the image processing operations in the embodiment. FIG. 44 shows positional relationship of adjacent outer area Ht relative to one rectangle area RO in the image processing operations in the embodiment. FIG. 45 shows an example of an angle θt that is formed between an approximate gradient vector Vgt and a directional vector Vdt in the image processing operations in the embodiment. FIG. 46 schematically shows an example of an image of inside of a body cavity captured by a capsule endoscope used in the embodiment. FIG. 47 shows an example of a classification result for the image shown in FIG. 46.

The control unit 9a of the terminal apparatus 7 first performs processing similar to the processing from steps S201 to S203 of FIG. 32 described above. That is, the control unit 9a inputs an image signal that is based on an image of inside of a body cavity captured by the capsule endoscope 3, applies preprocessing to the ith input image Ii (step S241 in FIG. 41), divides the image Ii into m×n small areas (step S242 in FIG. 41), and then calculates color information and texture information as feature values in each of the small areas (step S243 in FIG. 41). The control unit 9a then identifies areas among the small areas that are classified into a class predefined as a class that has structurally obvious features, e.g., bubble class, by performing image processing to be discussed below (step S244 in FIG. 41). In this embodiment, the control unit 9a divides the image Ii into the m×n small areas so that each of the areas has a size of lx=ly=8, that is, is a rectangle area that includes 8×8 pixels.

Specifically, the control unit 9a further divides each rectangle area of 8×8 pixels in four in plane Gi, which is a green plane, out of planes of the image Ii so that it creates small rectangle areas each of which has 4×4 pixels (step S251 in FIG. 42). The control unit 9a calculates an average value ga of density values of G (green) pixels in each of the small rectangle areas that has 4×4 pixels and then virtually assigns numbers that have an arrangement such as shown in FIG. 43 to the individual small rectangle areas of 4×4 pixels. Then, the control unit 9a sets a direction represented by the segment connecting between areas 1 and 7 or areas 2 and 8 as a vertical direction in the image, a direction represented by the segment that connects between areas 3 and 4 or areas 5 and 6 as a horizontal direction in the image, a direction represented by the segment that connects between the areas 2 and 5 or the areas 4 and 7 as a left diagonal direction in the image, and a direction represented by the segment that connects between the areas 1 and 6 or the areas 3 and 8 as a right diagonal direction in the image. Thereafter, the control unit 9a calculates the logarithmic difference of the average value ga of G pixel density values between the areas. The control unit 9a subsequently determines that an arrangement of pixels that represents an approximately circular edge exists in the direction on the image where combination of areas that has the largest logarithmic difference exists, and temporarily saves the largest logarithmic difference and the direction in the image that gives the largest value.

The control unit 9a, which serves as an area of interest setting unit and an adjacent outer area detection unit, virtually sets the position of one area RO, which serves as an area of interest, as an area in which the center of the approximate circle exists as coordinates (xo, yo) as shown in FIG. 44 among the rectangle areas each containing 8×8 pixels. Then, it detects an adjacent outer area Ht (t=1, 2, 3, . . . , T) that is represented by coordinates (xt, yt) as an area that is away from (xo, yo) by a distance Q (Q=1, 2, 3, . . . ), that is, an area in which at least a portion of the edge of the approximate circle centered at RO may exist, according to Formula (26) below (step S252 in FIG. 42):

$$[((xo-xt)^2+(yo-yt)^2)^{1/2}]=Q \tag{26}$$

In Formula (26) described above, [ ] represents Gaussian symbols.

After detecting all the coordinates (xt, yt) that meet Formula (26) described above, the control unit 9a, which serves as a vector calculation unit, calculates the approximate gradient vector Vgt in each of detected adjacent outer areas and the directional vector Vdt that connects between the coordinates (xt, yt) and the coordinates (xo, yo) (step S253 in FIG. 42).

The approximate gradient vector Vgt in each adjacent outer area Ht is a vector that has the largest logarithmic difference of the average value ga of G pixel density values saved in the control unit 9a as its magnitude and has the direction in the image that gives the largest value as its direction.

When it calculates the approximate gradient vector Vgt and the directional vector Vdt in each adjacent outer area Ht, the control unit 9a determines whether |Vgt|, i.e., the magnitude of Vgt, is equal to or larger than a threshold value (0.4 in this embodiment). If it detects that the value of |Vgt| is equal to or larger than the threshold value, the control unit 9a calculates a value of cos θt according to Formula (27) below for an angle θt that is formed between the approximate gradient vector Vgt and the directional vector Vdt shown in FIG. 45 based on the inner product formula (step S254 in FIG. 42).

$$\cos \theta t = Vgt \cdot Vdt / |Vgt||Vdt| \tag{27}$$

If it detects that the value of |cos θt| is greater than 0.7 based on the calculation of cos θt using Formula (27) described above (step S255 in FIG. 42), the control unit 9a, which serves as an edge determination unit, determines that a radial gradient vector centered at one rectangle area RO exists in the adjacent outer area Ht, that is, at least a portion of edges of the approximate circle centered at area RO exists in it, and also extracts that rectangle area RO.

When the radial gradient vector centered at rectangle area RO exists in L areas out of T adjacent outer areas, if a value of L/T is at or above 0.7 (step S256 in FIG. 42) the control unit 9a, which serves as an area extraction unit, determines that the center of a bubble that has an approximately circular shape exists in the extracted rectangle area RO based on the value of L/T. Then, the control unit 9a varies the value of distance Q up to a value of Qmax which is preset by the user and performs the processing described above at individual values of distance Q (steps S257 and S258 in FIG. 42). The control unit 9a also sets one rectangle area RO sequentially for all the rectangle areas each of which has 8×8 pixels, and performs the processing described above for each area RO it sets (steps S259 and S260 in FIG. 42). Through such processing, the control unit 9a detects areas that are classified into the bubble class in accordance with various sizes of bubbles that exist in various areas of the image Ii.

Then, in order to detect areas that are classified into the villus class among areas other than ones classified into the bubble class (step S245 in FIG. 41), the control unit 9a performs processing similar to the processing at steps S205 to S210 in FIG. 32.

That is, as mentioned above, the control unit 9a calculates a posterior probability P(ω1|x) that a feature vector x that has occurred belongs to a class ω1, a posterior probability P(ω2|x) that the feature vector x that has occurred belongs to a class ω2, a posterior probability P(ω3|x) that the feature vector x that has occurred belongs to a class ω3, and a posterior probability P(ω4|x) that the feature vector x that has occurred belongs to a class ω4, using Formulas (20) to (22) described above that contains an average vector μa and a variance-covariance matrix Σa that are calculated in advance for each class based on training data. The control unit 9a then identifies that the feature vector x belongs to a class ωa that gives the largest posterior probability P1(ωa|x) among the four posterior probabilities and classifies the area Hj in which the feature vector x has occurred to the class ωa based on the identification results. Assuming that the villus class is the class ω1 (a=1), the control unit 9a detects areas that have been classified into the class ω1 in the preceding processing among the m×n areas and calculates a probability density function p1(x|ω1) that gives the largest posterior probability P1(ω1|x) in each of the detected areas.

Then, in order to determine the classification of the areas into the class ω1 is correct or not, the control unit 9a further performs processing that is based on a threshold value for the value of probability density function p1(x|ω1) which gives the larges posterior probability P1(ω1|x).

Specifically, as described earlier, the control unit 9a determines a threshold vector xb1 that contains the sum of an average value μx1 of a feature value x1, for example, among the average values of the five feature values of an average vector μ1 that are calculated in advance based on teaching data, and the product of standard deviation σx1 of the feature value x1 and a multiplication coefficient α as a predetermined constant. For reliable classification into the villus class, the value of multiplication coefficient α is set to 0.8 in this processing as a value serving as the threshold value for p1(x|ω1). Once the threshold vector xb1 is determined, the control unit 9a substitutes the threshold vector xb1 into x in Formulas (20), (21) and (22) described above to calculate a probability density function p(xb1|ω1).

For an area the value of for which p1(x|ω1) is larger than the value of p(xb1|ω1), the control unit 9a determines that its classification into the villus class is correct, and for an area for which the value of p1(x|ω1) is equal to or smaller than the value of p(xb1|ω1), determines that its classification into the villus class is not correct and classifies the area into the unknown class.

By performing such processing to the m×n areas, the control unit 9a detects areas that are classified into the villus class among areas other than ones classified into the bubble class. Then, based on the detection results in the preceding processing, the control unit 9a calculates the average vector μ1 and a variance-covariance matrix Σ1 that are population parameters constituting the villus class from the five feature values contained in each area classified into the villus class (step S246 in FIG. 41). Assuming that the bubble class is ω2 (a=2), the control unit 9a calculates an average vector μ2 and a variance-covariance matrix Σ2 that are population parameters constituting the bubble class from the five feature values contained in each area classified into the bubble class based on the detection result from the previous processing (step S246 in FIG. 41). The control unit 9a then uses the average vector μ1 and the variance-covariance matrix Σ1 that are population parameters constituting the villus class as well as the average vector μ2 and the variance-covariance matrix Σ2 that are population parameters constituting the bubble class to perform the image processing which has been described in the seventh or eighth embodiment of the invention to the image Ii like one shown in FIG. 46, thereby obtaining a final classification result shown in FIG. 47 (step S247 in FIG. 41).

The detections of areas to be classified into the bubble class in this embodiment is not limited to the one illustrated above but may also be carried out in a following manner.

The control unit 9a detects the adjacent outer area Ht represented by the coordinates (xt, yt) according to Formula (28) below for a bubble that has a distorted edge and therefore elliptical shape.

$$Q-\beta \leq [((xo-xt)^2+(yo-yt)^2)^{1/2}] \leq Q+\beta \qquad (28)$$

In Formula (28) described above, β is an integer equal to or greater than 1 and [ ] represents Gaussian symbols.

After detecting all coordinates (xt, yt) that meet Formula (28) described above, the control unit 9a calculates the approximate gradient vector Vgt and the directional vector Vdt that connects between each coordinates (xt, yt) and the coordinates (xo, yo) in each of the detected adjacent outer areas. The control unit 9a then determines whether |Vgt|, i.e., the magnitude of Vgt, is equal to or larger than a threshold value (0.4 in this embodiment). If it detects that the value of |Vgt| is equal to or larger than the threshold value, the control unit 9a calculates the value of cos θt according to Formula (27) described above for the angle θt that is formed between the approximate gradient vector Vgt and the directional vector Vdt based on the inner product formula.

If it detects that the value of |cos θt| is greater than 0.7 based on the calculation of cos θt using Formula (27) described above, the control unit 9a determines that a radial gradient vector centered at one rectangle area RO exists in the adjacent outer area Ht. The control unit 9a further sets the adjacent outer area in which it determines that the radial gradient vector exists as Ht1, binarizes other adjacent outer areas as Ht0, and then applies thinning to the areas that have been detected as Ht1. Thereafter, the control unit 9s counts the number of areas that remain to be Ht1 after the thinning. If the number of such areas is L1, the control unit 9a calculates a value of L1/T from the number of areas L1 and the number of adjacent outer areas T that has been detected with Formula (26). If the value of L1/T is equal to or greater than a threshold value (e.g., 0.7), the control unit 9a determines that the center of the approximately circular bubble that has a distorted edge shape exists in the area RO based on the value of L1/T.

In the processing described above, the control unit 9a may also detect adjacent outer areas that have the radial gradient vector in the range from distances (Q−β) to (Q+β) while varying the direction in steps of an angle φ between 0° and 360° with the area RO as the center. In this case, the control unit 9a sets the number of direction S in which it determines that an adjacent outer area having the radial gradient vector exists and sets the number of adjacent outer areas T to [360/φ], then calculates a value of S/T. And based on the value of S/T, the control unit 9a determines that the center of a bubble exists in the area RO if the value of S/T is equal to or larger than a threshold value (e.g., 0.7).

The vector used by the control unit 9a for detecting areas to be classified into the bubble class in this embodiment is not limited to the approximate gradient vector but may be an average gradient vector, for example.

As has been thus described, this embodiment provides an effect of improved efficiency of observation that uses the capsule endoscope device 1 as in the seventh embodiment and also can classify areas of an image input to the terminal apparatus 7 into the bubble class efficiently even when the classification by the feature values including the color information and the texture information is difficult.

In addition, according to the embodiment, by calculating population parameters in advance based on images input to the terminal apparatus 7 for bubble and villus classes that have structurally obvious features, the classification of areas into the bubble and villus classes can be carried out further accurately.

Although the seventh to ninth embodiments of the invention use images captured by the capsule endoscope 3 as objects of image processing, similar effects of processing can be also provided when the image processing method is applied to images captured by an endoscope that has a configuration different from the capsule endoscope 3, for example.

While the seventh to ninth embodiments of the invention use the five values based on the color information and the texture information as values constituting the feature values, the values constituting the feature values can be changed or added as appropriate for the user's application and the like.

The seventh to ninth embodiments of the invention can determine whether a result of lesion site detection has been obtained from a biological mucosa surface or not when used in combination with image processing for detecting a lesion site such as bleeding or redness, thereby enhancing accuracy of lesion site detection.

The present invention is not limited to the embodiments illustrated above and it goes without saying that various modifications or applications are possible without departing from the scope of the invention.

The present application is filed for claiming a priority over Japanese Patent Applications No. 2005-115960 and No. 2005-115961 filed in Japan on Apr. 13, 2005 and contents disclosed by the applications are cited in the specification, claims and drawings of the present application.

The invention claimed is:

1. An image processing apparatus comprising;
an image inputting unit configured to input a medical image having a plurality of color signals;
a determining unit configured to determine whether a biological mucosa is sufficiently captured in the inputted medical image or not; and
a controlling unit configured to control at least either displaying or storing of the medical image based on the determination result in the determining unit;
an image dividing unit configured to divide the medical image into a plurality of areas;
a feature value calculating unit configured to calculate one or more feature values in each of the plurality of areas of the medical image;
an area classifying unit configured to identify which class of the plurality of classes each of the plurality of areas belongs to based on the feature value and classify each of the plurality of areas by the identification result;
a classification determining value calculating unit configured to calculate a proportion of a group of areas classified in a predetermined class among the plurality of classes in the plurality of areas based on the classification result by the area classifying unit; and
an image classifying unit configured to classify the image having the group of areas classified into the predetermined class based on the proportion calculated by the classification determining value calculating unit and a predetermined threshold relating to the proportion;
wherein the determining unit determines that the medical image is an image in which a biological mucosa is not sufficiently captured if the proportion is a predetermined threshold or less, and determines that the medical image is an image in which a biological mucosa is sufficiently captured if the proportion is larger than the predetermined threshold, based on the classification result by the image classifying unit.

2. The image processing apparatus according to claim 1, wherein the controlling unit controls not to display the medical image which is determined that the biological mucosa is not sufficiently captured by the determining unit.

3. The image processing apparatus according to claim 2, wherein the controlling unit controls not to store the medical image which is determined that the biological mucosa is not sufficiently captured by the determining unit.

4. The image processing apparatus according to claim 3, further including an image deleting unit configured to delete the medical image which is determined that the biological mucosa is not sufficiently captured by the determining unit.

5. The image processing apparatus according to claim 2, further including an image deleting unit configured to delete the medical image which is determined that the biological mucosa is not sufficiently captured by the determining unit.

6. The image processing apparatus according to claim 1, wherein the controlling unit controls not to store the medical image which is determined that the biological mucosa is not sufficiently captured by the determining unit.

7. The image processing apparatus according to claim 6, further including an image deleting unit configured to delete the medical image which is determined that the biological mucosa is not sufficiently captured by the determining unit.

8. The image processing apparatus according to claim 1, further including an image deleting unit configured to delete the medical image which is determined that the biological mucosa is not sufficiently captured by the determining unit.

9. The image processing apparatus according to claim 1, wherein the feature value has at least either the feature value relating to a color or the feature value relating to a texture.

10. The image processing apparatus according to claim 1, wherein the area determining unit determines, if an area is classified into a class relating to a biological mucosa, that the area is the area in which a biological mucosa is captured based on the classification result of the area classifying unit.

11. The image processing apparatus according to claim 10, wherein the detection result determining unit determines that the detection result of the detection unit is correct, if the area which is suspected to have a lesion is the area in which a biological mucosa is captured based on the detection result of the detecting unit and the determination result of the area determining unit.

12. The image processing apparatus according to claim 1, wherein the feature value has at least either a feature value relating to a color or a feature value relating to a texture.

13. The image processing apparatus according to claim 1, wherein the plurality of classes has at least a gastric mucosa class, a villi class, and a feces class.

14. The image processing apparatus according to claim 13, wherein, if the predetermined class is the gastric mucosa class, the identifying unit determines that the organ whose image is captured in the medical image is the gaster.

15. The image processing apparatus according to claim 13, wherein, if the predetermined class is the villi class, the identifying unit determines that the organ whose image is captured in the medical image is the small intestine.

16. The image processing apparatus according to claim 13, wherein, if the predetermined class is the feces class, the identifying unit determines that the organ whose image is captured in the medical image is the large intestine.

17. The image processing apparatus according to 1, wherein the feature value has at least either the feature value relating to a color or the feature value relating to a texture.

18. An image processing apparatus including:
an image inputting unit configured to input a plurality of medical images including a plurality of color signals;
an area setting unit configured to set a plurality of areas for the inputted medical images;
a detecting unit configured to detect an area which is suspected to have a lesion from the plurality of areas;
an area determining unit configured to determine whether the plurality of areas set by the area setting unit are areas in each of which a biological mucosa is captured or not; and
a detection result determining unit configured to determine whether a detection result by the detecting unit is right or wrong based on the determination result in the area determining unit;
a feature value calculating unit configured to calculate one or more feature values in each of the plurality of areas of the medical image;
an area classifying unit configured to classify the plurality of areas into any of a plurality of classes including a class relating to a biological mucosa and a class relating to a non-biological mucosa based on the feature value;
an edge detecting unit configured to detect an area having an edge in the plurality of areas based on a density value of a green component of the medical image;
a bleeding site determining unit configured to determine whether an area having the edge is an area including a bleeding site or not based on a density value of a red component of the image; and
a classification result determining unit configured to determine whether the classification result of the area classifying unit is right or wrong based on the determination result of the bleeding site determining unit
wherein the detecting unit detects an area including the bleeding site as an area which is suspected to have a lesion.

19. An image processing apparatus including:
an image inputting unit configured to input a plurality of medical images captured serially in time order;
an image dividing unit configured to divide the medical image into a plurality of areas;
a feature value calculating unit configured to calculate one or more feature values in each of the plurality of areas of the medical image;
an area classifying unit configured to identify which class of the plurality of classes each of the plurality of areas belongs to based on the feature value and classify each of the plurality of areas by the identification result;
a classification determination value calculating unit configured to calculate a proportion of a group of areas classified in a predetermined class among the plurality of classes in the plurality of areas based on the classification result by the area classifying unit;
an image classifying unit configured to classify the image having the group of areas classified into the predetermined class based on the proportion calculated by the classification determination value calculating unit and the predetermined threshold relating to the proportion;
an identifying unit configured to identify an organ whose image is captured in the medical image based on a classification result by the image classifying unit; and
an identification result displaying unit configured to display an identification result by the identifying unit.

20. An image processing apparatus including:
an image signal inputting unit configured to input an image signal based on an image captured by a medical appliance having an image capturing function;
an image dividing unit configured to divide an image captured by the medical appliance into a plurality of areas based on the image signals inputted by the image signal inputting unit;
a feature value calculating unit configured to calculate one or more feature values in each of the plurality of areas divided by the image dividing unit;
a first area classifying unit configured to classify the plurality of areas into any of the plurality of classes based on the feature value calculated by the feature value calculating unit and a predetermined first classifying criterion;
a classifying criterion setting unit configured to set a second classifying criterion based on the feature value and the classification result by the first area classifying unit; and
a second area classifying unit configured to classify the plurality of areas into any of the plurality of classes based on the feature value and the second classifying criterion,
wherein the first area classifying unit classifies each of the plurality of areas into any of the plurality of classes by using a statistical discriminator which uses a parameter for determining the first classifying criterion, and the second area classifying unit classifies each of the plurality of areas into any of the plurality of classes by using a statistical discriminator which uses a parameter for determining the second classifying criterion.

21. The image processing apparatus according to claim 20, wherein the feature value has at least either the feature value relating to a color or the feature value relating to a texture.

22. The image processing apparatus according to claim 20, further including:
an evaluated value calculating unit configured to evaluate the classification result by the second area classifying unit of one area among the plurality of areas by calculating an evaluated value based on the classification result by the second area classifying unit of the area placed near the one area; and
a third area classifying unit configured to classify the one area into any of the plurality of classes based on the evaluated value in the evaluated value calculating unit.

23. The image processing apparatus according to claim 22, wherein the feature value has at least either the feature value relating to a color or the feature value relating to a texture.

24. An image processing apparatus including:
an image signal inputting unit configured to input an image signal based on an image captured by a medical appliance having an image capturing function;
an image dividing unit configured to divide an image captured by the medical appliance into a plurality of areas based on the image signal inputted by the image signal inputting unit;
a feature value calculating unit configured to calculate one or more feature values in each of the plurality of areas divided by the image dividing unit;
a notice area setting unit configured to set one area among the plurality of areas as a notice area;

a close circumference area detecting unit configured to detect a close circumference area which is an area at a predetermined distance from the notice area;

an approximately round shape detecting unit configured to detect the presence of at least a part of a contour part of the approximately round shape based on the feature value in the close circumference area; and an area extracting unit configured to extract the notice area, if the approximately round shape is detected by the approximately round shape detecting unit.

25. The image processing apparatus according to claim 24, wherein the feature value has at least either the feature value relating to a color or the feature value relating to a texture.

26. The image processing apparatus according to claim 25, wherein the approximately round shape is a bubble.

27. The image processing apparatus according to claim 24, wherein the approximately round shape detecting unit detects an approximately round shape if it is determined that a proportion of an area in which at least a part of the contour part of the approximately round shape is a predetermined threshold or more in the close circumference area, and the area extracting unit extracts the notice area as an area in which a center part of the approximately round shape is present.

28. The image processing apparatus according to claim 27, wherein the approximately round shape is a bubble.

29. An image processing method including:
an image inputting step for inputting an image captured by a medical appliance having an image capturing function;
an area dividing step for dividing the image into a plurality of areas;
a feature value calculating step for calculating one or more feature values from each of the plurality of areas; and
an area classifying step for classifying each of the plurality of areas into either an area in which a surface of a biological mucosa is captured or an area in which a non-biological mucosa is captured based on the feature value;
a determining step for determining whether a surface of a biological mucosa is captured in the image or not based on the classification result of each of the plurality of areas at the area classifying step;
a classification determining value calculating step for calculating a proportion of a group of areas classified in a predetermined class among a plurality of different classes including a class relating to a biological mucosa and a class relating to a non-biological mucosa in the plurality of areas based on the classified result by the area classifying step; and
an image classifying step for classifying the image having the group of areas classified into the predetermined class based on the proportion calculated at the classification determining value calculating step and a predetermined threshold relating to the proportion;
wherein the determining step determines that the image is an image in which a biological mucosa is not sufficiently captured if the proportion is a determined threshold or less, and determines that the image is an image which a biological mucosa is sufficiently captured if the proportion is larger than the predetermined threshold, based on the classification result at the image classifying step.

30. The image processing method according to claim 29, wherein the feature value has at least either the feature value relating to a color or the feature value relating to a texture.

31. An image processing method including:
an image inputting step for inputting an image captured by a medical appliance having an image capturing function;
an area dividing step for dividing the image into a plurality of areas;
a feature value calculating step for calculating one or more feature values from each of the plurality of areas;
an area classifying step for classifying each area of the plurality of areas into any one of a plurality of different classes based on the feature value;
a determining step for determining whether a surface of a biological mucosa is captured in the image or not based on the classification result of each of the plurality of areas at the area classifying step;
a classification determining value calculating step for calculating a proportion of a group of areas classified in a predetermined class among the plurality of different classes in the plurality of areas based on the classified result at the area classifying step; and
an image classifying step for classifying the image having the group of areas classified into the predetermined class based on the proportion calculated at the classification determining value calculating step and a predetermined threshold relating to the proportion;
wherein the area classifying step classifies each area of the plurality of areas into any of the plurality of classes including one or more classes relating to a biological mucosa, one or more classes relating to a non-biological mucosa and one or more classes relating to neither the biological mucosa nor the non-biological mucosa,
and the determining step determines that the image is an image in which a biological mucosa is not sufficiently captured if the proportion is a predetermined threshold or less, and determines that the image is an image in which a biological mucosa is sufficiently captured if the proportion is larger than the predetermined threshold, based on the classification result at the image classifying step.

32. The image processing method to claim 31, wherein the feature value has at least either the feature value relating to a color or the feature value relating to a texture.

33. An image processing method including:
an image inputting step for inputting an image captured by a medical appliance having an image capturing function;
an area dividing step for dividing the image into a plurality of areas;
a feature value calculating step for calculating one or more feature values from each of the plurality of areas;
an area classifying step for classifying each area of the plurality of areas into any one class among a plurality of different classes based on the feature value;
an excluded class setting step for setting combinations of excluded classes which are not permitted to be mixed on the image in the plurality of different classes; and
a preferential class setting step for setting which class is to be preferred among the combinations of the excluded classes;
wherein if an area classified into any class of the combinations of the excluded classes set at the excluded class setting step is present, the area classifying step classifies the area into a class set at the preferential class setting step.

34. The image processing method according to claim 33, further including:
a classification determining value calculating step for calculating a proportion of a group of areas classified in one class among the classes included in the combinations of the excluded classes in the plurality of areas based on the classification result by the area classifying step;

wherein the preferential class setting step sets which class among the combinations of excluded classes is to be preferred by comparing the proportion calculated at the classification determining value calculating step and a predetermined threshold relating to the proportion.

35. The image processing method according to claim 34, further including a determining step for determining whether a surface of a biological mucosa is captured in the image or not based on the classification result of each of the plurality of areas at the area classifying step.

36. The image processing method according to claim 35, further including:
a classification determining value calculating step for calculating a proportion of a group of areas classified in a predetermined class among the plurality of different classes in the plurality of areas based on classification result at the area classifying step; and
an image classifying step for classifying the image having the group of areas classified into the predetermined class based on the proportion calculated at the classification determining value calculating step and a predetermined threshold relating to the proportion;
wherein the determining step determines that the image is an image in which a biological mucosa is not sufficiently captured if the proportion is a predetermined threshold or less, and determines that the image is an image in which a biological mucosa is sufficiently captured if the proportion is more than the predetermined threshold, based on the classification result at the image classifying step.

37. The image processing method to claim 33, wherein the feature value has at least either the feature value relating to a color or the feature value relating to a texture.

38. An image processing method including:
an image inputting step for inputting an image captured by a medical appliance having an image capturing function;
an area dividing step for dividing the image into a plurality of areas;
a feature value calculating step for calculating one or more feature values in each of the plurality of areas;
an area classifying step for identifying which class of a plurality of classes each of the plurality of areas belongs to based on the feature value and classifying each of the plurality of areas by the identification result;
a classification determining value calculating step for calculating a proportion of a group of areas classified into a predetermined class among the plurality of classes in the plurality of classes in the plurality of areas based on the classification result at the area classifying step;
an image classifying step for classifying the image having the group of areas classified into the predetermined class based on the proportion calculated at the classification determining value calculating step and a predetermined threshold relating to the proportion; and
an image-captured organ estimating step for estimating an organ captured in the image based on the classification result at the image classifying step.

39. The image processing method according to claim 38, wherein the plurality of classes has at least a gastric mucosa class, a villi class, and a feces class.

40. The image processing method according to claim 39, wherein, if the predetermined class is the gastric mucosa class, the identifying unit determines that the organ whose image is captured in the image is the gaster.

41. The image processing method according to claim 39, wherein, if the predetermined class is the villi class, the identifying unit determines that the organ whose image is captured in the image is the small intestine.

42. The image processing method according to claim 39, wherein, if the predetermined class is the feces class, the identifying unit determines that the organ whose image is captured in the image is the large intestine.

43. The image processing method according to claim 38, wherein the feature value has at least either the feature value relating to a color or the feature value relating to a texture.

44. An image processing method including:
an image dividing step for dividing the image captured by the medical appliance into a plurality of areas based on the image signal inputted at the image signals inputting unit configured to input an image signal according to an image captured by the medical appliance having an image capturing function;
a feature value calculating step for calculating one or more feature values in each of a plurality of areas divided at the image dividing step;
a first area classifying step for classifying each of the plurality of areas into any of a plurality of classes based on the feature value calculated at the feature value calculating step and a predetermined first classifying criterion;
a classifying criterion setting step for setting a second classifying criterion based on the feature value and the classification result at the first area classifying step; and
a second area classifying step for classifying each of the plurality of areas into any of the plurality of classes based on the feature value and the second classifying criterion;
wherein the first area classifying step classifies each of the plurality of areas into any of the plurality of classes by using a statistical discriminator which uses a parameter for determining the first classifying criterion, and the second area classifying step classifies each of the plurality of areas into any of the plurality of classes by using a statistical discriminator which uses a parameter for determining the second classifying criterion.

45. The image processing method according to claim 44, wherein the feature value has at least either the feature value relating to a color or the feature value relating to a texture.

46. The image processing method according to claim 44, further including:
an evaluated value calculating step for evaluating the classification result at the second area classifying step of one area among the plurality of areas by calculating an evaluated value based on the classification result at the second area classifying step of the area placed near the one area; and
a third area classifying step for classifying the one area into any of the plurality of classes based on the evaluated value at the evaluated value calculating step.

47. The image processing method according to claim 46, wherein the feature value has at least either the feature value relating to a color or the feature value relating to a texture.

48. An image processing method including:
an image dividing step for dividing the image captured by the medical appliance into a plurality of areas based on the image signal inputted at the image signals inputting unit configured to input an image signal according to an image captured by the medical appliance having an image capturing function;
a feature value calculating step for calculating one or more feature values in each of the plurality of areas divided at the image dividing step;

a notice area setting step for setting an area among the plurality of areas as a notice area;

a close circumference area detecting step for detecting a close circumference area which is an area at a predetermined distance from the notice area;

an approximately round shape detecting step for detecting a presence of at least a part of a contour part of the approximately round shape based on the feature value in the close circumference area; and an area extracting step for extracting the notice area, if the approximately round shape is detected at the approximately round shape detecting step.

49. The image processing method according to claim 48, wherein the feature value has at least either the feature value relating to a color or the feature value relating to a texture.

50. The image processing method according to claim 48, wherein the approximately round shape detecting step detects an approximately round shape if it is determined that a proportion of an area in which at least a part of the contour part of the approximately round shape is a predetermined threshold or more in the close circumference area, and the area extracting step extracts the notice area as an area in which a center part of the approximately round shape exists.

51. The image processing method according to claim 50, wherein the approximately round shape is a bubble.

52. The image processing method according to claim 48, wherein the approximately round shape is a bubble.

53. An image processing method including:
inputting an image captured by a medical appliance;
dividing the image into a plurality of areas;
calculating one or more feature values from each of the plurality of areas; and
classifying each of the plurality of areas into either an area in which a surface of a biological mucosa is captured or an area in which a non-biological mucosa is captured based on the feature value;
determining whether a surface of a biological mucosa is captured in the image or not based on the classification result of each of the plurality of areas;
calculating a proportion of a group of areas classified into a predetermined class among the plurality of different classes including a class relating to a biological mucosa and a class relating to a non-biological mucosa in the plurality of areas based on the classification result of each of the plurality of areas; and
classifying the image having the group of areas classified into the predetermined class based on the proportion and a predetermined threshold relating to the proportion;
wherein it is determined that the image is an image in which a biological mucosa is not sufficiently captured if the proportion is a predetermined threshold or less, and it is determined that the image is an image in which a biological mucosa is sufficiently captured if the proportion is larger than the predetermined threshold, based on the classification result of the image.

54. An image processing method including:
inputting an image captured by a medical appliance;
dividing the image into a plurality of areas;
calculating one or more feature values from each of the plurality of areas; and
classifying each area of the plurality of areas into any one class among a plurality of different classes including one or more classes relating to a biological mucosa, one or more classes relating to a non-biological mucosa, and one or more classes relating to neither the biological mucosa nor the non-biological mucosa, based on the feature value;
determining whether a surface of a biological mucosa is captured in the image or not based on the classification result of each of the plurality of areas;
calculating a proportion of a group of areas classified into a predetermined class among the plurality of different classes including a classes in the plurality of areas based on the classification result of each of the plurality of areas; and
classifying the image having the group of areas classified into the predetermined class based on the proportion and a predetermined threshold relating to the proportion;
wherein it is determined that the image is an image in which a biological mucosa is not sufficiently captured if the proportion is a predetermined threshold or less, and it is determined that the image is an image in which a biological mucosa is sufficiently captured if the proportion is larger than the predetermined threshold, based on the classification result of the image.

55. An image processing method including:
inputting an image captured by a medical appliance;
dividing the image into a plurality of areas;
calculating one or more feature values from each of the plurality of areas;
classifying each area of the plurality of areas into any one class among a plurality of different classes based on the feature value;
setting combinations of excluded classes which are not permitted to be mixed on the image in the plurality of different classes;
setting one class to be preferentially classified among the combinations of the excluded classes; and
classifying the area into the one class, if an area classified into any class of the combinations of the excluded classes is present.

56. An image processing method including:
inputting an image captured by a medical appliance;
dividing the image into a plurality of areas;
calculating one or more feature values in each of the plurality of areas;
identifying which class of a plurality of classes each of the plurality of areas belongs to based on the feature value and classifying each of the plurality of areas by the identification result;
calculating a proportion of a group of areas classified in a predetermined class among the plurality of classes in the plurality of areas based on the classification result of each of the plurality of areas;
classifying the image having the group of areas classified into the predetermined class based on the proportion and a predetermined threshold relating to the proportion; and
estimating an organ whose image is captured by the medical appliance based on the classification result of the image.

57. An image processing method including:
dividing the image captured by the medical appliance into a plurality of areas based on the image signal inputted at an image signal inputting unit configured to input an image signal according to an image captured by a medical appliance;
calculating one or more feature values in each of the plurality of areas;
classifying each of the plurality of areas into any of a plurality of classes based on the feature value and a predetermined first classifying criterion by using a statistical discriminator which uses a parameter for determining the predetermined first classifying criterion;

setting a second classifying criterion based on the feature value and the classification result of the plurality of areas by using a statistical discriminator which uses a parameter for determining the first classifying criterion; and classifying each of the plurality of areas into any of the plurality of classes based on the feature value and the second classifying criterion by using a statistical discriminator which uses a parameter for determining the second classifying criterion.

58. The image processing method according to claim 57, including:

evaluating the classification result of one area classified by using the statistical discriminator which uses the parameter for determining the second classifying criterion among the plurality of areas by calculating an evaluated value based on the classification result of the area placed near the one area classified by using the statistical discriminator which uses the parameter for determining the second classifying criterion; and classifying the one area into any of the plurality of classes based on the evaluated value.

59. An image processing method including:

inputting an image signal according to an image captured by a medical appliance and dividing the image captured by the medical appliance into a plurality of areas based on the image signal;

calculating one or more feature values in each of the plurality of areas;

setting an area among the plurality of areas as a notice area;

detecting a close circumference area which is an area at a predetermined distance from the notice area;

detecting a presence of at least a part of a contour part of the approximately round shape based on the feature value in the close circumference area; and extracting the notice area, if the approximately round shape is detected.

* * * * *